(12) United States Patent
Watson-Straughan et al.

(10) Patent No.: US 6,768,024 B1
(45) Date of Patent: Jul. 27, 2004

(54) TRIAMINE DERIVATIVE MELANOCORTIN RECEPTOR LIGANDS AND METHODS OF USING SAME

(75) Inventors: Karen J. Watson-Straughan, Encinitas, CA (US); Timothy C. Gahman, Encinitas, CA (US); Ming Qi, San Diego, CA (US); Christa Hamashin, San Diego, CA (US); James E. Macdonald, San Diego, CA (US); Michael J. Green, Encinitas, CA (US); Kevin R. Holme, San Diego, CA (US); Michael C. Griffith, San Diego, CA (US)

(73) Assignee: Lion Bioscience AG (DE)

( * ) Notice: Subject to any disclaimer, the term of this patent is extended or adjusted under 35 U.S.C. 154(b) by 0 days.

(21) Appl. No.: 09/632,928

(22) Filed: Aug. 4, 2000

(51) Int. Cl.[7] ............................................. C07C 211/00
(52) U.S. Cl. ..................... 564/367; 564/230; 564/237; 564/229; 546/300; 546/277.4; 544/107; 544/162; 548/340.1; 549/65
(58) Field of Search ................................ 564/230, 237, 564/367, 229; 546/500, 277.4; 544/107, 162; 548/340.1; 549/65

(56) References Cited

U.S. PATENT DOCUMENTS

| | | | |
|---|---|---|---|
| 3,376,344 A | * | 4/1968 | Lane et al |
| 5,010,175 A | | 4/1991 | Rutter et al. |
| 5,508,432 A | | 4/1996 | Sugg et al. |
| 5,534,530 A | | 7/1996 | Frehel et al. |
| 5,646,140 A | | 7/1997 | Sugg et al. |
| 5,656,648 A | | 8/1997 | Boigegrain et al. |
| 5,670,479 A | * | 9/1997 | Abelman et al. |
| 5,731,340 A | | 3/1998 | Bras et al. |
| 5,739,129 A | | 4/1998 | Aquino et al. |
| 5,795,887 A | | 8/1998 | Aquino et al. |
| 5,859,007 A | | 1/1999 | Aquino et al. |

FOREIGN PATENT DOCUMENTS

| | | |
|---|---|---|
| WO | WO 91/19735 | 12/1991 |
| WO | WO 98/34113 | 8/1998 |
| WO | WO 99/21571 | 5/1999 |

OTHER PUBLICATIONS

US 5,889,182, 3/1999, Dezube et al. (withdrawn)
cas online printout of US 5670479, m=197080–83–4.*
U.S. patent application Ser. No. 09/027,108, Dooley et al., filed Feb. 20, 1998.
Catania and Lipton, "α–Melanocyte–Stimulating Hormone peptides in Host responses." Ann. N. Y. Acad. Sci., 680:412–23 (1993).
Catania et al., "The Neuropeptide α–MSH has Specific Receptors on Neutrophils and reduces Chenotaxis In Vitro," *Peptides*, 17:675–79 (1996).

(List continued on next page.)

*Primary Examiner*—Samuel Barts
(74) *Attorney, Agent, or Firm*—Law Office of David Spolter

(57) ABSTRACT

The invention provides triamine derivative melanocortin receptor ligands of the formula:

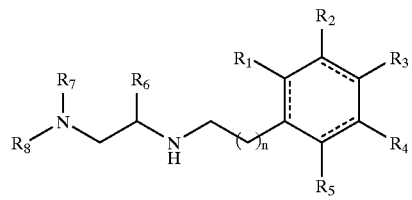

wherein $R_1$ to $R_8$ and n have the meanings provided herein. The invention further provides methods of using the ligands to alter or regulate the activity of a melanocortin receptor.

19 Claims, 5 Drawing Sheets

OTHER PUBLICATIONS

Dorr et al., "Evaluation of melatonin—IT, a Superpotent Cyclic Melanotropic Peptide in a Pilot Phase—I Clinical Study," *Life Sciences*, 50:1777–84 (1996).

Fan et al., "Role of melanocrtinergic neurons in feeding and the *aqouti* obesity syndrome," *Nature*, 385:165–68 (1997).

Hotamisligil and Spiegelman, "Tumor Necrosis Factor α: A Key Component of the Obesity–Diabetes Link," *Diabetes*, 43:1271–78 (1994).

Hotamisligil et al., "Increased Adipose Tissue Expression of Tumor Necrosis Factor–αin Human Obesity and Insulin Recistance," *J. Clin. Invest..*, 95:2409–15 (1995).

Hotamisligil et al., "Reduced Tyrosine Kinase Activity of the Insulin Receptor in Obesity–Diabetes," *J. Clin. Invest.*, 94:1543–49 (1994).

Huszar et al., "Targeted Disruption of the Melanocortin 4 Receptor Results in Obesity in Mice," *Cell*, 88:131–41 (1997).

Kuby, "Immunology," 3$^{rd}$ ed., Chapter 13 (W. H. Freeman & Co.; N. Y. 1997).

Ollmann et al., "Antagonism of Central Melanocortin Receptors in Vitro and in Vivo by Agouti–Related Protein," *Science*, 378:135–37 (1997).

Ostresh, "Solid–Phase Synthesis of Trisubstituted Bicyclic Guanidines via Cyclization of Reduced N–Acylated Dipeptides." *J. Org. Chem.*, 63:8622–23 (1998).

Platzer et al., "Up–regulation of monocytic IL–10 by tumor necrosic factor—α and camp elevating drugs," *International Immunology*, 7:517–23 (1995).

Star et al., "Evidence of autocrine modulation of macrophage nitric oxide synthase by α—melanocyte–stimulating hormone," *Proc. Natl. Acad. Sci. USA*, 92:8016–20 (1995).

Jeffrey B. Tatro, Receptor Biology of the Melanocortins, a family of Meuroimmunodulatory Peptides, *Neuroimmunomodulation*, 3:259–84 (1997).

Xia et al., "Expression of melanocortin 1 receptor in periaqueductal gray matter," *NeuroReport*, 6:2193–96 (1995).

* cited by examiner

TRIAMINE DERIVATIVE MELANOCORTIN RECEPTOR LIGANDS AND METHODS OF USING SAME

FIELD OF THE INVENTION

The present invention relates generally to the fields of medicinal chemistry and molecular pathology and, more specifically, to novel triamine derivatives and their use as melanocortin receptor ligands and as agents for controlling obesity, sexual dysfunction or inflammation.

BACKGROUND INFORMATION

The melanocortin (MC) receptors are a group of cell surface proteins that mediate a variety of physiological effects, including regulation of adrenal gland function such as production of the glucocorticoids cortisol and aldosterone; control of melanocyte growth and pigment production; thermoregulation; immunomodulation; analgesia; obesity; feeding disorders; and sexual dysfunction. Five distinct MC receptors have been cloned and are expressed in a variety of tissues, including melanocytes, adrenal cortex, brain, gut, placenta, skeletal muscle, lung, spleen, thymus, bone marrow, pituitary, gonads and adipose tissue (Tatro, *Neuroimmunomodulation* 3:259–284 (1996)). Three MC receptors, MCR-1, MCR-3 and MCR-4, are expressed in brain tissue (Xia et al., *Neuroreport* 6:2193–2196 (1995)).

A variety of ligands termed melanocortins function as agonists that stimulate the activity of MC receptors. The melanocortins include melanocyte-stimulating hormones (MSH) such as α-MSH, β-MSH and γ-MSH, as well as adrenocorticotropic hormone (ACTH). Individual ligands can bind to multiple MC receptors with differing relative affinities. The variety of ligands and MC receptors with differential tissue-specific expression likely provides the molecular basis for the diverse physiological effects of melanocortins and MC receptors. For example, α-MSH antagonizes the actions of immunological substances such as cytokines and acts to modulate fever, inflammation and immune responses (Catania and Lipton, *Annals N. Y. Acad. Sci.* 680:412–423 (1993)).

More recently, the role of specific MC receptors in some of the physiological effects described above for MC receptors has been elucidated. For example, in MCR-1 is involved in pain and inflammation. MCR-1 mRNA is expressed in neutrophils (Catania et al., *Peptides* 17:675–679 (1996)). The anti-inflammatory agent α-MSH was found to inhibit migration of neutrophils. Thus, the presence of MCR-1 in neutrophils correlates with the anti-inflammatory activity of α-MSH.

An interesting link of MC receptors to regulation of food intake and obesity has recently been described. The brain MC receptor MCR-4 has been shown to function in the regulation of body weight and food intake. Mice in which MCR-4 has been knocked out exhibit weight gain (Huszar et al., *Cell* 88:131–141 (1997)). In addition, injecting synthetic peptides that mimic melanocortins and bind to MCR-4 into the brain of normal and mutant obese mice caused suppressed feeding (Fan et al., *Nature* 385:165–168 (1997)). These results indicate that the brain MC receptor MCR-4 functions in regulating food intake and body weight.

Due to the varied physiological activities of MC receptors, high affinity ligands of MC receptors could be used to exploit the varied physiological responses of MC receptors by functioning as potential therapeutic agents or as lead compounds for the development of therapeutic agents. Furthermore, due to the effect of MC receptors on the activity of various cytokines, high affinity MC receptor ligands could also be used to regulate cytokine activity.

Thus, there exists a need for ligands that bind to MC receptors with high affinity for use in altering MC receptor activity. The present invention satisfies this need and provides related advantages as well.

SUMMARY OF THE INVENTION

The invention provides triamine derivative melanocortin receptor ligands of the formula:

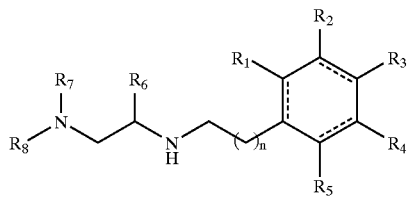

wherein $R_1$ to $R_8$ and n have the meanings provided below. The invention further provides methods of using the ligands to alter or regulate the activity of a melanocortin receptor.

DETAILED DESCRIPTION OF THE INVENTION

Figure 1:
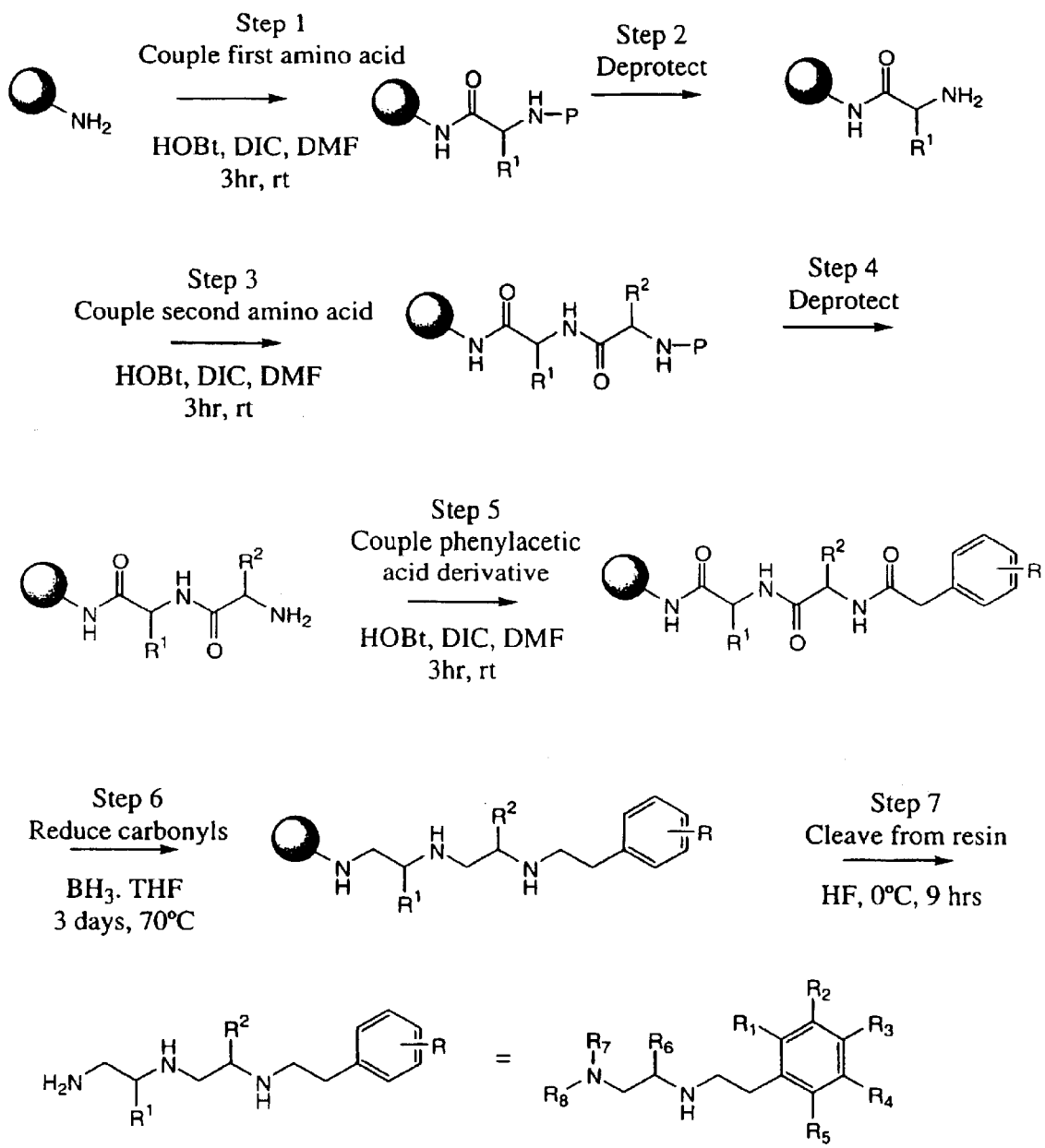
FIG. 1 shows a general reaction scheme for synthesis of triamine derivatives.

The invention provides triamine derivative compounds, as well as combinatorial libraries of such compounds. The invention further provides triamine derivative ligands for MC receptors and methods of using such ligands to alter the activity of a MC receptor. The invention also provides MC receptor triamine derivative ligands that are useful for regulating cytokine activity and treating sexual dysfunction or body weight in a subject.

Specifically, the invention provides compounds and combinatorial libraries of the formula:

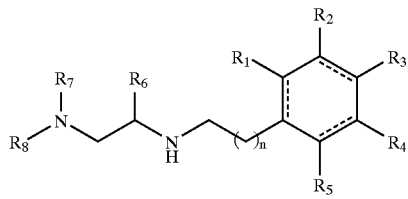

wherein:
the dotted lines indicate that the depicted ring is phenyl or cyclohexyl;

n is 0, 1 or 2;

$R_1$ to $R_5$ are, independently, a hydrogen atom, halo, hydroxy, protected hydroxy, nitro, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_1$ to $C_6$ alkoxy, $C_1$ to $C_6$ substituted alkoxy, phenoxy, substituted phenoxy, $C_1$ to $C_6$ alkylthio, $C_1$ to $C_6$ substituted alkylthio, $C_1$ to $C_6$ alkylsulfonyl, $C_1$ to $C_6$ substituted alkylsulfonyl, phenylthio, substituted phenylthio, phenylsulfonyl, substituted phenylsulfonyl, amino, protected amino, (monosubstituted) amino, protected (monosubstituted) amino or (disubstituted)amino; and when any one of adjacent position pairs $R_1$ and $R_2$, $R_2$ and $R_3$, and $R_3$ and $R_4$ and $R_4$ and $R_5$ together form one of the following groups: phenyl, substituted phenyl, heterocycle and substituted heterocycle, where such group is fused to the phenyl ring depicted in the above formula such that a bicyclic ring results;

$R_6$ is a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_{11}$ to $C_{16}$ naphthylalkyl or $C_{11}$ to $C_{16}$ substituted naphthylalkyl;

where $R_7$ is absent, $R_8$ together with the attached nitrogen depicted in the above formula form a substituted heterocycle or a substituted cyclic $C_3$ to $C_7$ heteroalkylene, wherein at least one of said substitution is the formula -D-E, wherein D may be absent or present and, if present, is $C_1$ to $C_6$ alkylene or $C_1$ to $C_6$ substituted alkylene; and E is amino, protected amino, (monosubstituted)amino, protected (monosubstituted) amino or (disubstituted)amino group; and where $R_7$ is a hydrogen atom, $C_1$ to $C_6$ alkyl or $C_1$ to $C_6$ substituted alkyl, $R_8$ is the formula X—CH—Y, wherein the attached nitrogen depicted in the above formula is attached to the carbon atom of the formula X—CH—Y, and wherein X is a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl, naphthyl or substituted naphthyl, and Y is the formula —(CH$_2$)$_n$—Z, wherein n is 1 to 6 and Z is amino, protected amino, (monosubstituted) amino, protected (monosubstituted)amino or (disubstituted)amino; or a pharmaceutically-acceptable salt thereof.

In another embodiment, where $R_1$ to $R_5$ and $R_7$ are each hydrogen and $R_8$ is the formula X—CH—Y, X is benzyl and Y is —CH$_2$-amino, $R_6$ is not benzyl.

In an additional embodiment, the ring depicted in the above formula is phenyl. In another embodiment, the ring is cyclohexyl.

In a further embodiment, at least one of $R_1$ to $R_5$ is not hydrogen.

The invention also provides compounds and libraries wherein $R_6$ is as described above, provided that $R_6$ is not benzyl.

The invention further provides compounds and libraries wherein $R_1$ to $R_5$ are, independently, a hydrogen atom, halo, hydroxy, protected hydroxy, nitro, $C_1$ to $C_6$ alkyl, $C_1$ to $C_6$ substituted alkyl, phenyl, substituted phenyl, $C_1$ to $C_6$ alkylthio, $C_1$ to $C_6$ substituted alkylthio, Ad $C_1$ to $C_6$ alkylsulfonyl, $C_1$ to $C_6$ substituted alkylsulfonyl, $C_1$ to $C_6$ alkoxy, $C_1$ to $C_6$ substituted alkoxy, phenoxy, substituted phenoxy, amino, (monosubstituted)amino or (disubstituted) amino.

The invention also provides compounds and libraries wherein $R_6$ is $C_1$ to $C_6$ alkyl, $C_1$ to $C_6$ substituted alkyl, $C_7$ to $C_{12}$ phenylalkyl or $C_7$ to $C_{12}$ substituted phenylalkyl.

Also provided are compounds and libraries wherein $R_7$ is absent and $R_8$ together with the attached nitrogen depicted in the above formula form a substituted heterocycle or a substituted cyclic $C_3$ to $C_7$ heteroalkylene, wherein at least one of said substitution is the formula -D-E, wherein D is $C_1$ to $C_6$ alkylene and E is amino, (monosubstituted)amino or (disubstituted)amino.

In another embodiment, $R_7$ is a hydrogen atom and $R_8$ is the formula X—CH—Y, wherein the attached nitrogen depicted in the above formula is attached to the carbon atom of the formula X—CH—Y, and wherein X is $C_1$ to $C_6$ alkyl, $C_1$ to $C_6$ substituted alkyl, $C_7$ to $C_{12}$ phenylalkyl or $C_7$ to $C_{12}$ substituted phenylalkyl and Y is the formula —(CH$_2$)$_m$—Z, wherein m is 1 or 2 and Z is amino, (monosubstituted)amino or (disubstituted)amino.

In an additional embodiment, $R_1$ to $R_5$ are, independently, a hydrogen atom, methyl, isopropyl, hydroxy, ethoxy, methoxy, butoxy, phenoxy, chloro, fluoro, bromo, nitro, trifluoromethyl, phenyl, methylthio, trifluoromethylthio, trifluoromethoxy, methylsulfonyl or dimethylamino.

The invention also provides compounds and libraries wherein $R_2$ and $R_3$ form a phenyl or substituted phenyl that is fused to the phenyl depicted in the above formula.

The invention additionally provides compounds and libraries wherein $R_6$ is benzyl, 4-(iodophenyl)methyl, 4-(chlorophenyl)methyl, 4-(bromophenyl)methyl, 2-(methoxyphenyl)methyl, 3-(methoxyphenyl)methyl, 4-(ethoxyphenyl)methyl, 4-(propoxyphenyl)methyl, 4-(ethylphenyl)methyl, 4-(isopropylphenyl)methyl, 4-(isobutylphenyl)methyl, 4-(trifluoromethylphenyl)methyl, 3,4-(dimethoxyphenyl)methyl, 4-(t-butylphenyl)methyl, 4-(2-(1-piperidyl)ethoxy)phenylmethyl, 4-((3,3-dimethyl)butoxyphenyl)methyl, 4-((3-methyl)butoxyphenyl)methyl, 4-((2-dimethylamino)ethoxyphenyl)methyl, 2-phenethyl, 2-(4-methoxyphenyl)ethyl, 3-indolylmethyl, 4-(biphenyl)methyl, 1-naphthylmethyl, 2-naphthylmethyl, diphenylmethyl, 3,4-dichlorophenylmethyl or 2-methoxyethyl.

In addition, the invention provides compounds and libraries wherein $R_7$ is absent and $R_8$ together with the nitrogen depicted in the above formula is 3-(aminomethyl)-7-hydroxyisoquinolyl, 3-(aminomethyl)isoquinolyl, 2-(aminomethyl)pyrrolidyl, trans-2-aminomethyl-4-hydroxypyrrolidyl, 4-aminomethylthiazolidin-3-yl or 2-(aminomethyl)piperidyl.

The invention further provides compounds and libraries wherein $R_7$ is a hydrogen atom and $R_8$ is the formula X—CH—Y, wherein Y is aminomethyl and X is 3-guanidinopropyl, 2-aminoethyl, 3-(methylamino)propyl, 4-aminobutyl, hydroxymethyl, 4-nitrophenylmethyl, benzyl, 3-(aminomethyl)phenylmethyl, 4-(aminomethyl)phenylmethyl, 4-hydroxyphenylmethyl, 3-pyridylmethyl, 4-pyridylmethyl, 2-thienylmethyl, butyl, 2-(ethylamino)ethyl, 2-(dimethylamino)ethyl, 3-(dimethylamino)propyl, 4-(dimethylamino)butyl, 1-hydroxyethyl, 2-hydroxyethyl, 3-hydroxypropyl, 1-methylethyl, 1,1-dimethylethyl, methoxymethyl, 2-pyridylmethyl, 2-methylsulfonylethyl, thiomethyl, 2-(methylthio)ethyl, 1-methyl-1-thioethyl, ethyl, 4-(2,2,2-trifluoroethylamino)butyl, aminomethyl, methylaminomethyl, dimethylaminomethyl, ethylaminomethyl, butylaminomethyl, 2,2-dimethylpropylaminoethyl, benzylaminoethyl, 2-phenethylaminomethyl, 3-phenylpropylaminomethyl, cyclohexylmethylaminomethyl, 2-cyclohexylethylaminomethyl, 4-hydroxybutylaminomethyl, 5-hydrdxypentylaminomethyl, 2-methoxyaminoethylaminomethyl, 3-methoxypropylaminomethyl, 2-phenoxyethylaminomethyl, 2-(2-methoxy)ethoxyethylaminomethyl, 2-thienylsulfonylaminoiethyl, 4-(methoxy)phenylsufonylaminomethyl, phenylsulfonylaminomethyl, 4-(butoxy)phenylsulfonylaminomethyl, methylsulfonylaminomethyl, 3-(4-morpholinyl)propyl, 3-cyclopropylaminopropyl, 3-(tetrahydofurfurylamino)propyl, 3-(4-hydroxypiperidinyl)propyl, 3-(1,1-dimethyl-2-hydroxyethylamino)propyl, 3-(N-(2-hydroxyethyl)methylamino)propyl, 3-(N-(cyclohexyl)methylamino)propyl, 2-(4-morpholinyl)ethyl, 2-cyclopropylaminoethyl, 2-(tetrahydrofurfurylamino)ethyl, 2-(4-hydroxypiperidinyl)ethyl, 2-(1,1-dimethyl-2-hydroxyethylamino)ethyl, 2-(N-(2-hydroxyethyl)methylamino)ethyl, 2-(N-(cyclohexyl)methylamino)ethyl, 4-ethylaminobutyl, 4-(2-methoxyethylamino)butyl, 3-ethylaminopropyl, 3-(2-methoxyethylamino)propyl, 3-pyridylmethylaminomethyl, 3-(methylamino)propyl, 3-aminopropyl, 3-(butylamino)propyl, 3-(2,2-dimethylpropylamino)propyl, 3-(phenylmethylamino)propyl, 3-(2-phenylethylamino)propyl, 3-(3-phenylpropylamino)propyl, 3-(2-cyclohexylethylamino)propyl, 3-(3-pridylmethylamino)propyl, 3-(3-methoxypropylamino)propyl, 3-(4-hydroxybutylamino)propyl, 3-(5-hydroxypentylamino)ppropyl, 3-(2-phenyoxyethylamino)propyl, 3-(methylamino)propyl, 4-aminobutyl, 4-(butylamino)butyl, 4-(2,2-dimethylpropylamino)butyl, 4-(phenylmethylaminom)butyl, 4-(2-phenylethylamino)butyl, 4-(3-phenylpropylamino)butyl, 4-(cyclohexylmethylamino)butyl, 4-(2-cyclohexylethylamino)butyl, 4-(3-pridylmethylamio)butyl, 4-(3-methoxypropylamino)butyl, 4-(4-hydroxybutylamino)butyl, 4-(5-hydroxypentylamino)butyl, 4-(2-phenyoxyethylamino)butyl or 4-((2-(2-methoxy)ethoxy)ethylamino)butyl.

The invention also provides a method of altering the activity of a melanocortin receptor in a subject, comprising administering to the subject an effective amount of a melanocortin receptor ligand, wherein said melanocortin receptor ligand comprises one of the compounds described above.

The method includes increasing the activity of a melanocortin receptor. The method of the invention also includes decreasing the activity of a melanocortin receptor. Melanocortin receptors whose activity can be increased or decreased include MC-1, MC-2, MC-3, MC-4 and MC-5.

Unless otherwise indicated, in the above formula the stereochemistry of chiral centers associated with the $R^1$ through $R^8$ groups can independently be in the R or S configuration, or a mixture of the two.

As used herein, the term "ene" (such as alkylene) denotes that the "ene" group connects together two separate additional groups.

As used herein, the term "alkyl" (such as $C_1$ to $C_9$ alkyl or $C_1$ to $C_6$ alkyl) denotes such radicals as methyl, ethyl, n-propyl, isopropyl, n-butyl, sec-butyl, tert-butyl, pentyl, tert-amyl, hexyl and the like up to chains of nine carbon atoms. Preferably, the compounds have $C_1$ to $C_8$, more preferably $C_1$ to $C_6$ and even more preferably $C_1$ to $C_3$ carbon chains. Most preferred is methyl.

The term "alkenyl" (such as $C_2$ to $C_9$ alkenyl, $C_2$ to $C_7$ alkenyl or $C_2$ to $C_6$ alkenyl) denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "alkynyl" (such as $C_2$ to $C_9$ alkynyl or $C_2$ to $C_7$ alkynyl) denotes such radicals as ethynyl, propynyl, butynyl, pentynyl, hexynyl, heptynyl, as well as di- and tri-ynes of straight and branched chains.

The terms "substituted alkyl," "substituted alkenyl," and "substituted alkynyl," denote that the above alkyl, alkenyl and alkynyl groups are substituted by one or more, and preferably one or two, halogen, hydroxy, protected hydroxy, oxo, protected oxo, cyclohexyl, naphthyl, amino, protected amino, (monosubstituted) amino, protected (monosubstituted) amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_7$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, cyano, $C_1$ to $C_6$ alkylsulfonylamino, phenylsulfonylamino, $C_1$ to $C_6$ substituted alkylsulfonylamino, substituted phenylsulfonylamino, thio, $C_1$ to $C_4$ alkylthio, $C_1$ to $C_6$ alkylsulfonyl, $C_1$ to $C_6$ substituted alkylsulfonyl, phenylsulfonyl, substituted phenylsulfonyl, heterocyclic sulfonyl or substituted heterocyclic sulfonyl groups. The substituted alkyl groups may be substituted once or more, and preferably once or twice, with the same or with different substituents.

Examples of the above substituted alkyl groups include the nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_6$ alkoxy" as used herein denotes groups such as methoxy, ethoxy, n-propoxy, isopropoxy, n-butoxy, t-butoxy and like groups. Preferred alkoxy groups are methoxy, ethoxy and propoxy. The term "$C_1$ to $C_6$ substituted alkoxy" as used herein denotes a "$C_1$ to $C_6$ alkoxy" that is substituted as described above regarding a "$C_1$ to $C_6$ substituted alkyl." The terms "phenoxy" and "substittuted phenoxy" should be similarly understood.

The term "$C_1$ to $C_7$ acyloxy" denotes herein groups such as formyloxy, acetoxy, propionyloxy, butyryloxy, pentanoyloxy, hexanoyloxy, heptanoyloxy and the like.

Similarly, the term "$C_1$ to $C_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by one or two halogen, hydroxy, protected hydroxy, $C_1$ to $C_6$ alkyl, $C_1$ to $C_7$ alkoxy, oxo, protected oxo, (monosubstituted)amino, (disubstituted)amino, trifluoromethyl, carboxy, protected carboxy, phenyl, substituted phenyl, amino, or protected amino groups.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical, halogen, hydroxy, protected hydroxy, $C_1$ to $C_7$ alkoxy, trifluoromethyl, carboxy, protected carboxy, oxo, protected oxo, (monosubstituted)amino, protected (monosubstituted) amino (disubstituted)amino, phenyl, substituted phenyl, amino, or protected amino.

The term "heterocyclic ring" or "heterocycle" denotes optionally substituted five-membered, six-membered or seven-membered rings that have 1 to 4 heteroatoms, such as oxygen, sulfur and/or nitrogen, in particular nitrogen, either alone or in conjunction with sulfur or oxygen ring atoms. These five-membered, six-membered or seven-membered rings may be saturated, fully saturated or partially unsaturated, with fully saturated rings being preferred. An "aminoalkyl-substituted heterocyclic ring" means any one of the above-described heterocyclic rings is substituted with at least one aminoalkyl group. Preferred heterocyclic rings include morpholino, piperidinyl, piperazinyl, tetrahydrofurano, pyrrolo, tetrahydrothiophen-yl, diazapino, thiomorpholino, thiazapino-S,S-dioxide, thiomorpholino-S, S-dioxide and thiazolidino-S,S-dioxide.

The term "substituted heterocyclic ring" or "substituted heterocycle" means the above-described heterocyclic ring is substituted with, for example, one or more, and preferably one or two, substituents which are the same or different and can be halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl), trifluoromethyl, $C_1$ to $C_6$ alkylsulfonyl, $C_1$ to $C_6$ substituted alkylsulfonyl, phenylsulfonyl, substituted phenylsulfonyl, phenylthio, substituted phenylthio, $C_1$ to $C_6$ alkylthio, $C_1$ to $C_6$ substituted alkylthio, N-(($C_1$ to $C_6$ alkyl)sulfonyl)amino or N-(phenylsulfonyl)amino groups. The term "aminoalkyl-substituted heterocyclic ring" is a heterocyclic ring substituted with at least one aminoalkyl group and the term "substituted aminoalkylsubstituted heterocyclic ring" is an aminoalkylsubstituted heterocyclic ring substituted with one or more of the above identified substituents for a substituted heterocyclic ring.

The abbreviation "Ar" stands for an aryl group. Aryl groups which can be used with present invention include phenyl, substituted phenyl, as defined above, heteroaryl, and substituted heteroaryl. The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, thiazolo and the like.

The term "substituted heteroaryl" means the above-described heteroaryl is substituted with, for example, one or more, and preferably one or two, substituents which are the same or different which can be halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl), trifluoromethyl, $C_1$ to $C_6$ alkylsulfonyl, $C_1$ to $C_6$ substituted alkylsulfonyl, phenylsulfonyl, substituted phenylsulfonyl, phenylthio, substituted phenylthio, $C_1$ to $C_6$ alkylthio, $C_1$ to $C_6$ substituted alkylthio, N-(($C_1$ to $C_6$ alkyl)sulfonyl)amino or N-(phenylsulfonyl)amino groups The terms "$C_7$ to $C_{12}$ phenylalkyl" and "$C_{11}$ to $C_{16}$ substituted naphthylalkyl" denotes a $C_1$ to $C_6$ alkyl group substituted at any position by a phenyl or naphthyl ring, respectively. Examples of such a group include benzyl, 2-phenethyl, 3-phenyl(n-propyl), 4-phenylhexyl, 3-phenyl (n-amyl), 3-phenyl(sec-butyl) and the like. Preferred $C_7$ to $C_{12}$ phenylalkyl groups are benzyl and phenethyl.

The terms "$C_7$ to $C_{12}$ substituted phenylalkyl" and "$C_{11}$ to $C_{16}$ substituted naphthylalkyl" denotes such a group substituted on the $C_1$ to $C_6$ alkyl portion with one or more, and preferably one or two, groups chosen from halogen, hydroxy, protected hydroxy, oxo, protected oxo, amino, protected amino, monosubstituted)amino, protected (monosubstituted)amino, (disubstituted)amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N—($C_1$ to $C_6$ dialkyl) carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl or naphthyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or a phenyl group, substituted or unsubstituted, for a resulting biphenyl group. The substituted alkyl or phenyl or naphthyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxyphenyl)-n-hexyl, 2-(5-cyano-3-methoxyphenyl)-n-pentyl, 3-(2,6- dimethylphenyl)-n-propyl, 4-chloro-3-aminobenzyl, 6-(4-methoxyphenyl)-3-carboxy(n-hexyl), 5-(4-aminomethylphenyl)-3-(aminomethyl)-n-pentyl, 5-phenyl-3-oxo-n-pent-1-yl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di ($C_1$ to $C_6$ alkyl) carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

Phenylthio, phenyl sulfoxide, phenylsulfonyl and phenylsulfonylamino compounds are known in the art and these terms have their art recognized definition. By "substituted phenylthio," "substituted phenyl sulfoxide," "substituted phenylsulfonyl" and "substituted phenylsulfonylamino" is meant that the phenyl can be substituted as described above in relation to "substituted phenyl."

The term "substituted aniline" specifies an aniline group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino and N-(phenylsulfonyl)amino.

Examples of substituted aniline include 2-fluoroanilinyl, 3-fluoroanilinyl, 4-fluoroanilinyl, 2-chloroanilinyl, 3-chloroanilinyl, 4-chloroanilinyl, 2-bromoanilinyl, 3-bromoanilinyl, 4-bromoanilinyl, 2-methoxyanilinyl, 3-methoxyanilinyl, 4-methoxyanilinyl, 2-hydroxyanilinyl, 3-hydroxyanilinyl, 4-hydroxyanilinyl, 2-carboethoxyanilinyl, 3-carboethoxyanilinyl, 4-carboethoxyanilinyl, 2-trifluoromethylanilinyl, 3-trifluoromethylanilinyl, 4-trifluoromethylanilinyl, 2-dimethylaminoanilinyl, 3-dimethylaminoanilinyl, 4-dimethylaminoanilinyl, 2-phenoxyanilinyl, 3-phenoxyanilinyl, 4-phenoxyanilinyl, 3,4-methylenedioxyanilinyl, 2,3-methylenedioxyanilinyl, 2,3-difluoroanilinyl, 2,3-dibromoanilinyl, 3,4-dibromoanilinyl, 2,3-dimethoxyanilinyl, 3,4-dimethoxyanilinyl, 1-amino-5,6,7,8-tetrahydronaphthyl, 2-hydroxy-3-amino-5,6,7,8-tetrahydronaphthyl, 2-aminonaphthyl, 1-amino-4-chloronaphthyl, 1-amino-4-bromonaphthyl, 5-amino-1-hydroxynaphthyl, 1-amino-2-hydroxynaphthyl, 5-aminoindanyl, 1-aminofluorenyl, 2-aminofluorenyl and N-methylanilinyl.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino.

Examples of the term "substituted naphthyl" include a mono or di(halo)naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy) naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy) naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy) naphthyl; a mono-or di(hydroxymethyl)naphthyl or (protected hydroxymethyl)naphthyl such as 1, 2, 3, 4, 5, 6, 7 or 8-(protected hydroxymethyl)naphthyl or 3,4-di (hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2, 3, or 4-(aminomethyl) naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The term "halo" or "halogen" refers to fluoro, chloro, bromo or iodo groups. Preferred halogens are bromo, fluoro and chloro.

The term "heterocyclic sulfonyl" refers to a sulfonyl group attached to a heterocycle. The term "substituted heterocyclic sulfonyl" refers to where the attached heterocycle is substituted as described herein.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl, heterocycle substituted heterocycle, $C_1$ to $C_6$ alkylsulfonyl, $C_1$ to $C_6$ substituted alkylsulfonyl, phenylsulfonyl, substituted phenylsulfonyl, heterocyclic sulfonyl and substituted heterocyclic sulfonyl. The (monosubstituted)amino can additionally have an amino-protecting group as encompassed by the term "protected (monosubstituted)amino."

Examples of the term (monosubstituted)amino include methylamino, ethylamino, cyclohexylamino, cyclohexylmethylamino, cyclohexylethylamino, cyclopentylamino, anilinyl, 2-methoxyanilinyl, benzylamino, 2-hydroxybenzylamino, phenethylamino, 2-methoxyphenethylamino and the like.

The term "(disubstituted)amino" refers to amino groups with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "protected amino" as used herein refers an amino group with a group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(S) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above. In addition, the term "protected carboxamide" means there is an amino-protecting group on the carboxamide nitrogen.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reactions and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, with the hydroxy becoming a "protected hydroxy". In addition, the term "protected hydroxymethyl" means there is a readily cleavable groups bonded to hydroxyl portion of the hydroxymethyl group. Examples of such readily cleavable groups bonded to hydroxyl groups include the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reactions and can be removedat the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The term "$C_1$ to $C_6$ alkylthio" refers to sulfide groups such as methylthio, ethylthio, n-propylthio, isopropylthio, n-butylthio, t-butylthio and like groups.

The term "$C_1$ to $C_6$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_6$ alkylsulfonyl" encompasses groups such as methylsulfonyl, ethylsulfonyl, n-propylsulfonyl, isopropylsulfonyl, n-butylsulfonyl, t-butylsulfonyl and the like. Similarly, the term "$C_1$ to $C_6$ alkylsulfonylamino" encompasses groups such as methylsulfonylamino, ethylsulfonylamino, n-propylsulfonylamino, isopropylsulfonylamino, n-butylsulfonylamino, t-butylsulfonylamino and the like. The terms "$C_1$ to $C_6$ substituted alkylthio," "$C_1$ to $C_6$ substituted alkylsulfoxide," "$C_1$ to $C_6$ substituted alkylsulfonyl" and "$C_1$ to $C_6$ substituted alkylsulfonylamino" refer to such groups with one or more substitutions as described above regarding the term "substituted alkyl." An example of $C_1$ to $C_6$ substituted alkylsulfonyl includes trifluoromethylsulfonyl.

By "substituted phenylthio," "substituted phenyl sulfoxide," "substittued phenoxy" and "substituted phenylsulfonyl" is meant that the phenyl can be substituted as described above in relation to "substituted phenyl."

The terms "cyclic $C_2$ to $C_7$ alkylene," "substituted cyclic $C_2$ to $C_7$ alkylene," "cyclic $C_2$ to $C_7$ heteroalkylene," "substituted cyclic $C_2$ to $C_7$ heteroalkylene," "cyclic $C_3$ to $C_7$ alkylene," "substituted cyclic $C_3$ to $C_7$ alkylene," "cyclic $C_3$ to $C_7$ heteroalkylene," and "substituted cyclic $C_3$ to $C_7$ heteroalkylene," define such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ or $C_3$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_4$ acyl, $C_1$ to $C_7$ alkyl, carbamoyl, $C_1$ to $C_7$ alkoxy, $C_1$ to $C_7$ alkylthio, $C_1$ to $C_4$ alkylsulfoxide, $C_1$ to $C_4$ alkylsulfonyl, halo, amino, protected amino, (monosubstituted) amino, protected (monosubstitued) amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the phenyl is fused to a pyridino, pyrano, pyrrolo, pyridinyl, dihydropyrrolo, or dihydropyridinyl ring. Examples of fused cyclic groups which each contain one oxygen atom and one or two double bonds are when the phenyl ring is fused to a furo, pyrano, dihydrofurano, or dihydropyrano ring. Examples of fused cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), β-Alanine, L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech; RSP; Bachem; or ChemImpex) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration.

As used herein, the phrase "any one of the twenty naturally-occurring amino acids" means any one of the following: Ala, Arg, Asn, Asp, Cys, Gln, Glu, Gly, His, Ile, Leu, Lys, Met, Phe, Pro, Ser, Thr, Trp, Tyr, and Val. As used herein, the language "the D-form of a naturally-occurring amino acid" means the D-isomer of any one of these naturally-occurring amino acids, with the exception of Gly, which does not occur as D or L isomers.

A One or more of the triamine derivatives, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.*, 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the above formula can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more triamine derivatives, even when in a library, can be in the biologically active carbamate form. Such a carbamate form can induce increased blood levels and prolong the efficacy of the corresponding non-carbamate form of the compound. Specific carbamates include methyl, ethyl and isobutyl carbamates.

A library prepared as described in Example I, below, can be useful for screening the library on the resin or alternatively can be cleaved from the resin as discrete compounds and screened in absence of resin. Preferably, the methods described above further comprise the step of cleaving the library from the resin to give discrete compounds.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of melanocortin receptor and related activity assays, such as those detailed below as well as others known in the art. The libraries will generally have at least one active compound and are generally prepared in such that the compounds are in equimolar quantities.

Compounds disclosed in previous work that are not in an intentially created collection are not part of a "combinatorial library" of the invention. In addition, compounds that are in an unintentional or undesired mixture are not part of a "combinatorial library" of the invention.

"Combinatorial chemistry" or "combinatorial synthesis" refers to the parallel synthesis of diverse compounds by sequential addition of reagents which leads to the generation of large chemical libraries having molecular diversity. Combinatorial chemistry, therefore, involves the systematic and repetitive, covalent connection of a set of different "building blocks" of varying structures to yield large arrays of diverse molecular entities.

A combinatorial library of the invention can contain two or more of the above-described compounds. The invention further provides a combinatorial library containing three or more, four or more or five or more of the above-described compounds. In another embodiment of the invention, a combinatorial library can contain ten or more of the above-described compounds. In yet another embodiment of the invention, a combinatorial library can contain fifty or more or 100 or more of the above-described compounds. If desired, a combinatorial library of the invention can contain 100,000 or more, or even 1,000,000 or more, of the above-described compounds.

By way of example, the preparation of the combinatorial libraries can use the "split resin approach." The split resin approach is described by, for example, U.S. Pat. No. 5,010,175 to Rutter, WO PCT 91/19735 to Simon, and Gallop et al., *J. Med. Chem.*, 37:1233–1251 (1994), all of which are incorporated herein by reference.

Triamine derivative compounds of the present invention can be synthesized essentially as described in U.S. patent application Ser. No. 09/018,173, WO 98/34113 and Ostresh et al., *J. Org. Chem.*, 63:8622–23 (1998), each of which is fully incorporated herein by reference. In addition, triamine derivative compounds of the present invention can be synthesized using the methods of synthesis described in Example I below.

The choice of chemical functional groups incorporated into specific positions on triamine derivatives will depend, in part, on the specific physical, chemical or biological characteristics required of the MC receptor ligand. Such characteristics are determined, in part, by the route by which the MC receptor ligand will be administered or the location in a subject to which the MC receptor ligand will be directed.

As used herein, the term "ligand" means a molecule that can selectively bind to a receptor. For example, a MC receptor ligand can selectively bind to a MC receptor. Those skilled in the art know what is meant by the term ligand. The triamine derivatives described herein are MC receptor ligands. A ligand can function as an agonist or antagonist. As used herein, the term "agonist" means that a ligand has the function of mimicking the physiological activity of another molecule. For example, a MC receptor ligand that functions as an agonist mimics the physiological activity of a MC receptor ligand such as MSE, which stimulates MC receptor activity. Similarly, the term "antagonist" means that a ligand has the function of reducing the physiological activity of another molecule, for example, by preventing the activation or inhibiting the activity of a receptor. For example, a MC receptor ligand that functions as an antagonist reduces the physiological activity of a MC receptor. A reduction in MC receptor activity can be due to the antagonist binding to the MC receptor and inhibiting activation or to the antagonist preventing the binding of a ligand that stimulates MC receptor activity.

The invention provides methods for altering the activity of a MC receptor in a subject by administering to the subject an effective amount of a MC receptor ligand, wherein the MC receptor ligand comprises an triamine derivative. The MC receptor ligands can be the triamine derivatives having the structures described above.

Some of the physiological effects of known MC receptor ligands on MC receptor activity are mediated by cytokines, and MC receptor ligands alter cytokine activity. Due to the effect of MC receptor signaling on cytokines, the MC receptor ligands of the invention can function as cytokine regulatory agents by regulating the aberrant or altered expression of one or more cytokines that occurs in various conditions, including, for example, pathologies, immune responses and inflammatory responses. Such conditions are considered together for purposes of the present invention in that they are characterized, in part, by altered or aberrant cytokine activity and, therefore, are amenable to regulation by one or more cytokine regulatory agents such as the MC receptor ligands disclosed herein.

It should be recognized, however, that while the MC receptor ligands of the invention can function as cytokine regulatory agents, no specific mechanism of action is proposed as to how a MC receptor ligand acts to affect a condition. The MC receptor ligands of the invention can be used to treat conditions characterized by altered or aberrant cytokine activity However, the conditions treatable with the MC receptor ligands of the invention are not restricted to those conditions or diseases involving altered cytokine activity. The MC receptor ligands are useful for treating a disease or condition if the MC receptor ligand prevents the disease or improves signs or symptoms of the disease, regardless of the mechanism causing the signs or symptoms of the disease.

The present invention provides a method of reducing a pathologically elevated cytokine activity in a subject by administering to the subject an effective amount of MC receptor ligands such as triamine derivatives. The pathologically elevated cytokine activity can be due, for example, to inflammation, cachexia, or a patho-immunogenic disease.

Aberrant cytokine expression can result in damage to healthy tissue in a subject and, in extreme cases, can lead to severe disability and death Cytokines can be expressed at a site of localized infection or can be expressed systemically, for example, in an immune response or in response to bacterial endotoxin-induced sepsis. Cytokine expression can induce pyrexia (fever) and hyperalgesia (extreme sensitivity to pain) in a subject, as well as macrophage and monocyte activation, which produces or further contributes to an inflammatory response in a subject.

Cytokines are well known in the art and include, but are not limited to the tumor necrosis factors (TNFs), colony stimulating factors (CSFs), interferons (INFs), interleukins (IL-1, IL-2, IL-3, IL-4, IL-5, IL-6, IL-7, IL-8, IL-9, IL-10, IL-11, IL-12, IL-13, IL-14, and IL-15), transforming growth factors (TGFs), oncostatin M (OSM), leukemia inhibiting factor (LIF), platelet activating factor (PAF) and other soluble immunoregulatory peptides that mediate host defense responses, cell regulation and cell differentiation (see, for example, Kuby, *Immunology* 3rd ed. (W. H. Free-man and Co., New York (1997); see Chapter 13, which is incorporated herein by reference).

A MC receptor ligand of the invention, such as a triamine derivative, can function as a cytokine regulatory agent and can be used to decrease the activity of a cytokine. For example, a particular pathological condition can cause an increase in the level or activity of a cytokine. A MC receptor ligand that functions to restrain cytokine activity can be used to lower the level or activity of the elevated cytokine. Such a reduction in cytokine activity can alleviate the symptoms of the pathological condition.

A MC receptor ligand such as one of the triamine derivatives disclosed herein can function as a cytokine regulatory agent and increase the levels of IL-10 in a mammal such as a human. IL-10 can block the activation of some inflammatory cytokines, including TNF, IL-1 and IL-6, while up-regulating cytokines such as IL-12. IL-10 also stimulates the proliferation of mast cells and thymocytes. IL-10 inhibits several monocyte and macrophage functions, including, for example, antigen presentation to T cells by depressing Class II MHC expression; synthesis of IL-1, IL-6, IL-8, CSF, and TNF; and microbicidal activities.

Administration of a MC receptor ligand can increase the plasma levels of IL-10 in mammals and, therefore, can be useful for modulating, for example, immunoresponsiveness in a subject.

The binding of a MC receptor ligand to a MC receptor results in a wide range of physiological responses. MC receptors are G protein-coupled receptors that activate adenylate cylcase and produce cAMP in response to binding of ligands such as MSH. Although many of the physiological effects of MC receptor signaling are mediated by cytokines, MC receptor ligands of the invention are not limited to those that regulate cytokine activity, as discussed above, but can be any MC receptor ligand that functions to alleviate the signs or symptoms of a disease or condition. Therefore, MC receptor ligands are useful for exploiting the various physiological responses mediated by MC receptor signaling.

The diversity of physiological responses to MC receptor signaling can be advantageously used to alter or regulate a physiological pathway that mediates or moderates a pathological condition or disease. The recent elucidation of the role of specific MC receptors in particular physiological pathways supports the use of ligands that activate specific MC receptors to modulate a physiological effect that results in a a given condition or disease. Therefore, MC receptor ligands of the invention, which alter the activity of a MC receptor that mediates or moderates a given condition or disease, are useful for treating that condition or disease.

MC receptor ligands such as triamine derivatives are useful for reducing inflammation. Administration of a triamine derivative can reduce inflammation in response to arachadonic acid administration. Thus compounds of the invention are useful for reducing inflammation.

Nitric oxide (NO) is induced during inflammation by a variety of proinflammatory cytokines. α-MSH was shown to inhibit production of NO through reduction of NO synthase and NO synthase mRNA (Star et al., *Proc. Natl. Acad. Sci. USA* 92:8016–8020 (1995)). Similarly, MC receptor ligands of the invention, such as triamine derivatives, can be used to inhibit NO production, thereby reducing inflammation.

Triamine derivative ligands of the invention that can alter the activity of an MC-3 receptor can be useful for treating sexual dysfunction and other conditions or conditions associated with MC-3 such as inflammation.

Other MC-3-associated conditions that can be treated with the MC-3 receptor ligands include disuse deconditioning;

organ damage such as organ transplantation or ischemic injury; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas's Disease.

The invention further provides a method for treating an MC-3-associated condition in a subject. The term "MC-3-associated condition" includes any condition or condition mediated by MC-3 or can be affected by binding an MC-3 ligand. Such conditions include inflammation and sexual dysfunction.

As used herein, the term "sexual dysfunction" means any condition that inhibits or impairs normal sexual function, including coitus. However, the term need not be limited to physiological conditions, but may include psychogenic conditions or perceived impairment without a formal diagnosis of pathology.

For the treatment of sexual dysfunction compounds of the present invention can be given in a dose range of 0.001 milligram to about 100 milligram per kilogram of body weight, preferably as a single dose orally or as a nasal spray.

In males, sexual dysfunction includes erectile dysfunction. As used herein, the term "erectile dysfunction" or "impotence" means the inability or impaired ability to attain or sustain an erection that would be of satisfactory rigidity for coitus. Sexual dysfunction in males can also include premature ejaculation and priapism, which is a condition of prolonged and sometimes painful erection unrelated to sexual activity, often associated with sickle-cell disease.

In females, sexual dysfunction includes sexual arousal disorder. The term "sexual arousal disorder" means herein a persistent or recurrent failure to attain or maintain the lubrication-swelling response of sexual excitement until completion of sexual activity. Sexual dysfunction in females can also include inhibited orgasm and dyspareunia, which is painful or difficult coitus. Sexual dysfunction can also be manifested as inhibited sexual desire or inhibited lordosis behavior in animals.

Triamine derivative compounds that activate MCR-4 are particularly useful for decreasing body weight. MCR-4 has been shown to function in regulating food intake and weight gain. Targeted disruption of MCR-4 causes mice to develop a maturity onset obesity associated with hyperphagia, hyperinsulinemia and hyperglycemia (Huszar et al., supra). Further evidence for the role of MC receptors in regulating food intake and weight gain involves the function of the agouti-related protein, which is a MCR-4 antagonist. An agouti-related protein functions as a selective antagonist of MCR-3 and MCR-4 and causes obesity in transgenic mice expressing agouti-related protein (Ollman et al., Science 278:135–137 (1997)). Furthermore, agouti analogs were injected into the brains of mice, and those analogs that functioned as MC receptor agonists inhibited feeding while those agouti analogs that functioned as antagonists increased feeding (Fan et al. supra). Thus, a functional role for MC receptors in regulating food intake and weight gain has been established. Therefore, the MC receptor ligands of the invention such as triamine derivatives are useful for treating obesity by decreasing food intake and body weight gain.

As disclosed herein, administration of a triamine derivative to rats resulted in a significant decrease in the rate of body weight gain and a significant decrease in body weight (see Example IX). As used herein, the term "decrease in body weight" is used broadly to mean an actual decrease in body weight or a decrease in the rate of body weight gain over time, as compared to the normal weight gain expected in the period of time. Thus triamine derivatives are particularly effective at reducing body weight and food consumption. These results indicate that a MC receptor ligand can cause a decrease in the rate of body weight gain and a decrease in food consumption.

An association between MC receptor signaling and body energy and metabolism has been reported (Huszar et al., supra). The MC receptor ligand HP 228 has been shown to modulate acute resting oxygen consumption (Omholt et al., *The Pharmacologist*, 39:53 (1997)), which is incorporated herein by reference. Therefore, MC receptor ligands of the invention can also be used for modulating the metabolic rate or acute oxygen consumption in a subject. The modulated metabolic rate can lead to a decrease in body weight. Thus, MC receptor ligands that can modulate the metabolic rate or acute oxygen consumption in a subject are particularly useful for decreasing body weight in a subject. The MC receptor ligands of the invention can be used to treat obesity and can independently or in combination affect body weight by decreasing food consumption or modulating metabolic rate or oxygen consumption.

In addition to MC receptor ligands that function as agonists that stimulate MC receptor activity, the invention also provides MC receptor ligands, such as triamine derivatives, that function as antagonists that inhibit MC receptor activity. MC receptor antagonists can be used, for example, to increase food intake and body weight analogous to that observed with the MC receptor antagonist agouti-related protein and the agouti analogs that function as antagonists (Fan et al., supra). MC receptor ligands that function as antagonists are particularly useful for increasing food intake and body weight in an individual suffering from cachexia, a general weight loss that occurs during chronic disease or emotional disturbance.

MC receptor ligands of the invention can also function as cytokine regulatory agents that are useful for treating diabetes. A link exists between obesity and non-insulin dependent diabetes mellitus (NIDDM) (Hotamisligil and Spiegelman, *Diabetes* 43:1271–1278 (1994a)). Therefore, MC receptor ligands are useful for decreasing the weight of an obese subject to prevent or alleviate the symptoms associated with NIDDM. Increased TNF-α expression has been detected in the adipose tissue of obese individuals and has been suggested to have a role in the appearance of NIDDM in these individuals (Hotamisligil et al., *J. Clin. Invest.* 95:2409–2415 (1995)). However, efforts to neutralize TNF activity using an antibody that binds the TNF receptor did not result in significant weight loss when examined in a rat obesity/diabetes model, the Zucker fa/fa rat model (Hotamisligil et al., *J. Clin Invest.* 94:1543–1549 (1994b)). Therefore, MC receptor ligands of the invention that decrease TNF-α are particularly useful for treating diabetes and associated obesity.

When treating obesity, in conjunction with diabetes or hyperglycemia, or alone, generally satisfactory results are obtained when the compounds of the present invention are administered at a daily dosage of from 0.01 milligrams to about 100 milligrams per kilogram of subject body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus or hyperglycemia, either alone or in combination, as well as when treating other diseases or disorders for which compounds of the present invention are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, for example, the total daily dose will generally be from about 0.07 milligrams to about 350 milligrams. This dosage regimen may be adjusted to provide the optimal therapeutic response.

The α-MSH analog MELANOTAN-II has been shown to cause penile erections in human subjects in pilot phase I clinical studies (Dorr et al., *Life Sciences* 58:1777–1784 (1996)). Therefore, MC receptors ligands of the invention can be used to treat erectile dysfunction in a subject (see Example X).

Other conditions that can be treated with the MC receptor ligands of the invention such as triamine derivatives include, but are not limited to, disuse deconditioning; organ damage such as occurs in response to organ transplantation or ischemic injury such as that which can occur after reperfusion or stroke; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas' Disease. Many of these conditions are characterized by altered or aberrant cytokine activity.

Other conditions that are treatable with melanocortin active compounds, such as the triamine derivatives of the present invention, include hypertension, fever, hypopigmentation, osteoarthritis, cancer, gall bladder disease, male and female sexual disorders, loss of libido, impotence, erectile dysfunction, cognitive and memory deficiencies, substance abuse, pain, sleep apnea, depression, anxiety, compulsion, neuroses, insomnia and other sleep disorders and Alzheimer's disease.

A variety of assays can be used to identify or characterize MC receptor ligands of the invention. For example, the ability of a triamine derivative to compete for binding of a known MC receptor ligand can be used to assess the affinity and specificity of a triamine derivative for one or more MC receptors. Any MC receptor ligand can be used so long as the ligand can be labeled with a detectable moiety. The detectable moiety can be, for example, a radiolabel, fluorescent label or chromophore, or any detectable functional moiety so long as the MC receptor ligand exhibits specific MC receptor binding. A particularly useful detectable MC receptor ligand for identifying and characterizing other MC receptor ligands is $^{125}$I-HP 467, which has the amino acid sequence Ac-Nle-Gln-His-(p(I)-D-Phe)-Arg-(D-Trp)-Gly-NH$_2$ and is described in Dooley et al., "Melanocortin Receptor Ligands and Methods of Using Same," U.S. patent application Ser. No. 09/027,108, filed Feb. 20, 1998, which is incorporated herein by reference. HP 467 is a para-iodinated form of HP 228. Thus MC receptor ligands can be identified using a detectable MC receptor ligand.

Using assay methods such as those described above and in Example II, a melanocortin receptor binding assay, binding kinetics and competition with radiolabeled HP 467 confirmed that triamine derivatives of the invention bind to one or more MC receptors (see Examples II and IV). Furthermore, as shown in Tables 1 to 5 below, the assays revealed that triamine derivatives of the invention exhibited a range of affinities and specificity for various MC receptors:

TABLE 1 selected MC receptor binding compounds

| Compound # | MC-1 IC50 uM | MC-3 IC50 uM | MC4- IC50 uM | MC-5 IC50 uM |
|---|---|---|---|---|
| 6603 #1 | 6.35 | 2.35 | 5.6 | 0.7 |
| 6603 #3 | 2.2 | 0.9 | 1.9 | 0.2 |
| 6603 #6 | 4 | 4.1 | 5.2 | 0.6 |
| 6603 #1.6 | 5.8 | 2.8 | 1.8 | 0.6 |

TABLE 2

Compounds with MC-1 receptor selectivity

| Compound # | MC-1 IC50 uM | MC-3 IC50 uM | MC-4- IC50 uM | MC-5 IC50 uM |
|---|---|---|---|---|
| 6610 #19 | 0.19 | ND | 6.0 | 0.3 |
| 6600 #9 | 0.25 | 14.3 | 19.55 | 0.46 |
| 6601 #10 | 0.33 | 0.8 | 1.8 | 0.7 |

TABLE 3

Compounds with MC-5 receptor selectivity

| Compound # | MC-1 IC50 uM | MC-3 IC50 uM | MC-4- IC50 uM | MC-5 IC50 uM |
|---|---|---|---|---|
| 6610 #4 | 0.3 | 0.6 | No fit | 0.03 |
| 6600 #2 | 0.27 | 1.34 | 1.2 | 0.07 |
| 6600 #8 | 0.42 | 1.09 | No fit | 0.04 |
| 6601 #23 | 0.59 | 1.79 | No fit | 0.06 |

TABLE 4

MC agonistic compounds

| Compound # | MC-1 IC50 uM | MC-3 IC50 uM | MC-4- IC50 uM | MC-5 IC50 uM |
|---|---|---|---|---|
| 6610 #1 | 0.4 | No fit | 0.9 | 0.35 |
| 6600 #3 | 0.6 | No fit | 0.3 | 0.15 |

TABLE 5

Compounds showing selective MC-1 agonism

| Compound # | MC-1 IC50 uM | MC-3 IC50 uM | MC-4- IC50 uM | MC-5 IC50 uM |
|---|---|---|---|---|
| 6610 #19 | 0.24 | Not tested | 4.7 | Not tested |
| 6600 #11 | 0.34 | No fit | 3.2 | No fit |

Tables 4 and 5 show compounds with MC agonism. The results from Tables 4 and 5 were generated as described below in Example III. The compounds listed in these Tables can be used, for example, to effect melanocortin receptor signaling (see Example V).

The invention provides MC receptor ligands that bind to several MC receptors with similar affinity (see Table 1). In addition, the invention also provides MC receptor ligands that show selectivity for one or more MC receptors (see Tables 2, 3 and 5). As used herein, the term "selectivity" means that the affinity of a MC receptor ligand differs between one MC receptor and another by about 10-fold, generally about 20- to 50-fold, and particularly about 100-fold. In some cases, a MC receptor ligand having broad specificity is desired. In other cases, it is desirable to use MC receptor ligands having selectivity for a particular MC receptor. For example, MCR-3 ligands are particularly useful for treating sexual dysfunction, whereas MCR-4 ligands are useful for treating obesity. The binding characteristics and specificity of a given MC receptor ligand can be selected based on the particular disease or physiological effect that is desired to be altered.

The invention also provides ligands with particular affinity for binding the MC-1 receptor (see Table 6 below). The invention further provides ligands with particular affinity for binding the MC-4 receptor (see Table 9 below).

In addition, the invention provides MC-1 agonists (see Table 7 below). Moreover, agonists particular for the MC-4 receptor is also provided (see Table 8 below).

TABLE 6

MC-1 Binders

| Pat R 1 | Pat R 2 | Pat R 3 | Pat R 4 | Pat R 5 | ring | N | Pat R 6 | Pat R 7 | Pat R8 | X | Y |
|---|---|---|---|---|---|---|---|---|---|---|---|
| H | H | H | H | H | phenyl | 2 | (S) 4-chlorophenylmethyl | H | (S) X—CH—Y | 3-guanidinopropyl | aminomethyl |
| H | H | Cl | H | H | phenyl | 1 | (S) 4-methoxyphenylmethyl | H | (S) X—CH—Y | 3-aminopropyl | aminomethyl |
| H | H | Cl | H | H | phenyl | 2 | (S) 3,4-dimethoxyphenylmethyl | H | (S) X—CH—Y | 3-aminoethyl | aminomethyl |
| H | H | OMe | H | H | phenyl | 2 | (S) 4-ethoxyphenylmethyl | H | (S) X—CH—Y | (3-(aminomethyl)phenyl)-methyl | aminomethyl |
| H | H | H | H | H | Cyhex | 0 | (S) 4-chlorophenylmethyl | H | (S) X—CH—Y | 3-guanidinopropyl | aminomethyl |
| H | H | H | H | H | Cyhex | 1 | (S) 4-ethoxyphenylmethyl | H | (S) X—CH—Y | (3-(aminomethyl)phenyl)-methyl | aminomethyl |
| H | H | Cl | H | H | phenyl | 2 | (S) 4-methoxyphenylmethyl | H | (S) X—CH—Y | 3-aminopropyl | aminomethyl |
| H | H | Cl | H | H | phenyl | 0 | (S) 3,4-dimethoxyphenylmethyl | H | (S) X—CH—Y | 3-aminoethyl | aminomethyl |
| H | H | H | H | H | phenyl | 2 | (S) 4-ethoxyphenylmethyl | H | (S) X—CH—Y | (3-(aminomethyl)phenyl)-methyl | aminomethyl |
| H | H | Cl | H | H | phenyl | 0 | (S) 4-ethoxyphenylmethyl | H | (S) X—CH—Y | 3-aminopropyl | aminomethyl |
| H | H | Cl | H | H | Cyhex | 1 | (S) 4-iodophenylmethyl | H | (S) X—CH—Y | 3-guanidinopropyl | aminomethyl |

TABLE 7

MC-1 Agonists

| Pat R 1 | Pat R 2 | Pat R 3 | Pat R 4 | Pat R 5 | Pat R 6 | Pat R 7 | Pat R8 | X | Y | n = |
|---|---|---|---|---|---|---|---|---|---|---|
| H | H | Cl | H | H | (s) 4-iodophenylmethyl | H | (S) X—CH—Y | 3-guanidinopropyl | Aminomethyl | 1 |
| H | H | F | H | H | (s) 4-iodophenylmethyl | H | (S) X—CH—Y | 3-guanidinopropyl | Aminomethyl | 1 |
| H | H | Cl | H | H | (S) (4-ethoxyphenyl)methyl | H | (S) X—CH—Y | 3-guanidinopropyl | Aminomethyl | 1 |
| H | H | Ethoxy | H | H | (R) (4-ethoxyphenyl)methyl | H | (R) X—CH—Y | 3-guanidinopropyl | Aminomethyl | 1 |
| H | H | Cl | H | H | (S) (4-ethoxyphenyl)methyl | H | (S) X—CH—Y | 2-aminoethyl | Aminomethyl | 1 |
| H | H | F | H | H | (S) (4-ethoxyphenyl)methyl | H | (S) X—CH—Y | 3-guanidinopropyl | Aminomethyl | 1 |
| H | H | Cl | H | H | (S) (4-ethoxyphenyl)methyl | H | (S) X—CH—Y | ethylaminomethyl | aminomethyl | 1 |
| H | H | Cl | H | H | (S) (4-ethoxyphenyl)methyl | H | (S) X—CH—Y | butylamiomethyl | aminomethyl | 1 |
| H | H | Cl | H | H | (S) (4-ethoxyphenyl)methyl | H | (S) X—CH—Y | 3-phenylpropylaminomethyl | aminomethyl | 1 |
| H | H | Cl | H | H | (S) (4-ethoxyphenyl)methyl | H | (S) X—CH—Y | 4-hydroxybutylaminomethyl | aminomethyl | 1 |
| H | H | Cl | H | H | (S) (4-ethoxyphenyl)methyl | H | (S) X—CH—Y | 5-hydroxypentylaminomethyl | aminomethyl | 1 |
| H | H | Cl | H | H | (S) (4-ethoxyphenyl)methyl | H | (S) X—CH—Y | 4-(phenylmethylamino)butyl | aminomethyl | 1 |
| H | H | Cl | H | H | (S) (4-ethoxyphenyl)methyl | H | (S) X—CH—Y | 4-(2-phenylethylamino)butyl | aminomethyl | 1 |
| H | H | Cl | H | H | (S) (4-ethoxyphenyl)methyl | H | (S) X—CH—Y | 2-(dimethylamino)ethyl | aminomethyl | 1 |
| H | H | Cl | H | H | (S) (4-ethoxyphenyl)methyl | H | (S) X—CH—Y | 3-(dimethylamino)propyl | aminomethyl | 1 |
| H | H | Cl | H | H | (S) (4-ethoxyphenyl)methyl | H | (S) X—CH—Y | 4-(dimethylamino)butyl | aminomethyl | 1 |

TABLE 8

| | R1 | R2 | R3 | R4 | R5 | R6 | R7 | R8 | X | Y |
|---|---|---|---|---|---|---|---|---|---|---|
| 1 | H | H | Cl | H | H | (S) (4-iodophenyl)methyl | H | (S) X—CH—Y | 3-guanidinopropyl | Aminomethyl |
| 2 | H | H | Cl | H | H | (S) (4-ethoxyphenyl)methyl | H | (S) X—CH—Y | 3-guanidinopropyl | Aminomethyl |
| 3 | H | H | F | H | H | (S) (4-iodophenyl)methyl | H | ($) X—CH—Y | 3-guanidinopropyl | Aminomethyl |
| 4 | H | H | F | H | H | (S) (4-phenylphenyl)methyl | H | (S) X—CH—Y | 3-guanidinopropyl | Aminomethyl |
| 5 | H | H | Cl | H | H | (S) (4-ethoxyphenyl)methyl | H | (S) X—CH—Y | 2-aminoethyl | Aminomethyl |
| 6 | H | H | Cl | H | H | (S) (4-ethoxyphenyl)methyl | H | (S) X—CH—Y | 2-aminoethyl | Aminomethyl |
| 7 | H | H | Cl | H | H | (S) (4-ethoxyphenyl)methyl | H | (S) X—CH—Y | 3-(methylamino)propyl | Aminomethyl |
| 8 | H | H | Cl | H | H | (S) (4-ethoxyphenyl)methyl | H | (S) X—CH—Y | 4-guanidinobutyl | Aminomethyl |
| 9 | H | H | Cl | H | H | (S) (4-ethoxyphenyl)methyl | H | (S) X—CH—Y | hydroxymethyl | Aminomethyl |
| 10 | H | H | Cl | H | H | (S) (4-ethoxyphenyl)methyl | H | (S) X—CH—Y | (3-aminomethyl)phenylmethyl | Aminomethyl |

TABLE 8-continued

| | R1 | R2 | R3 | R4 | R5 | R6 | R7 | R8 | X | | Y |
|---|---|---|---|---|---|---|---|---|---|---|---|
| 11 | H | H | Cl | H | H | (S) (4-iodophenyl)methyl | H | (S) X—CH—Y | 3-(methylamino)propyl | | Aminomethyl |
| 12 | H | H | Cl | H | H | (S) (4-iodophenyl)methyl | H | (S) X—CH—Y | 4-guanidinobutyl | | Aminomethyl |
| 13 | H | H | Cl | H | H | (S) (4-ethoxyphenyl)methyl | H | (S) X—CH—Y | 2-ethylaminoethyl | | Aminomethyl |
| 14 | H | H | Cl | H | H | (S) (4-ethoxyphenyl)methyl | H | (S) X—CH—Y | 2-dimethylaminoethyl | | Aminomethyl |
| 15 | H | H | Cl | H | H | (S) (4-ethoxyphenyl)methyl | H | (R) X—CH—Y | 3-dimethylaminopropyl | | aminomethyl |
| 16 | H | H | Cl | H | H | (S) (4-ethoxyphenyl)methyl | H | (R) X—CH—Y | 3-dimethylaminopropyl | | aminomethyl |
| 17 | H | H | Cl | H | H | (S) (4-ethoxyphenyl)methyl | H | (S) X—CH—Y | 2-((2-hydroxyethyl)methylamino)ethyl | | Aminomethyl |
| 18 | H | H | Cl | H | H | (S) (4-ethoxyphenyl)methyl | H | (S) X—CH—Y | 3-hydroxypropyl | | Aminomethyl |
| 19 | H | H | Cl | H | H | (S) (4-ethoxyphenyl)methyl | absent | (2-S, 4-R) trans-2-aminomethyl-4-hydroxypyrrolidine | | | |
| 20 | H | H | Cl | H | H | (S) (4-ethoxyphenyl)methyl | H | (R) X—CH—Y | methylaminopropyl | | aminomethyl |
| 21 | H | H | Cl | H | H | (S) (4-ethoxyphenyl)methyl | H | (R) X—CH—Y | 3-(ethylamino)propyl | | aminomethyl |
| 22 | H | H | Cl | H | H | (S) (4-ethoxyphenyl)methyl | H | (R) X—CH—Y | 3-(butylamino)propyl | | aminomethyl |
| 23 | H | H | Cl | H | H | (S) (4-ethoxyphenyl)methyl | H | (R) X—CH—Y | 3-(2,2-dimethylpropylamino)propyl | | aminomethyl |
| 24 | H | H | Cl | H | H | (S) (4-ethoxyphenyl)methyl | H | (R) X—CH—Y | 3-(cyclohexylmethylamino)propyl | | aminomethyl |
| 25 | H | H | Cl | H | H | (S) (4-ethoxyphenyl)methyl | H | (R) X—CH—Y | 3-(3-pridylmethylamino)propyl | | aminomethyl |
| 26 | H | H | Cl | H | H | (S) (4-ethoxyphenyl)methyl | H | (R) X—CH—Y | 3-(2-methoxyethylamino)propyl | | aminomethyl |
| 27 | H | H | Cl | H | H | (S) (4-ethoxyphenyl)methyl | H | (R) X—CH—Y | 3-(3-methoxypropylamino)propyl | | aminomethyl |
| 28 | H | H | Cl | H | H | (S) (4-ethoxyphenyl)methyl | H | (R) X—CH—Y | 3-(4-hydroxybutylamino)propyl | | aminomethyl |
| 29 | H | H | Cl | H | H | (S) (4-ethoxyphenyl)methyl | H | (R) X—CH—Y | 3-(5-hydroxypentylamino)propyl | | aminomethyl |
| 30 | H | H | Cl | H | H | (S) (4-ethoxyphenyl)methyl | H | (R) X—CH—Y | 3-(2-phenyoxyethylamino)propyl | | aminomethyl |
| 31 | H | H | Cl | H | H | (S) (4-ethoxyphenyl)methyl | H | (R) X—CH—Y | 4-(ethylamino)butyl | | aminomethyl |
| 32 | H | H | Cl | H | H | (S) (4-ethoxyphenyl)methyl | H | (R) X—CH—Y | 4-(2-methoxyethylamino)butyl | | aminomethyl |
| 33 | H | H | Cl | H | H | (S) (4-ethoxyphenyl)methyl | H | (R) X—CH—Y | 4-(3-methoxypropylamino)butyl | | aminomethyl |
| 34 | H | H | Cl | H | H | (S) (4-ethoxyphenyl)methyl | H | (R) X—CH—Y | 4-(4-hydroxybutylamino)butyl | | aminomethyl |
| 35 | H | H | Cl | H | H | (S) (4-ethoxyphenyl)methyl | H | (R) X—CH—Y | 4-(5-hydroxypentylamino)butyl | | aminomethyl |
| 36 | H | H | Cl | H | H | (S) (4-ethoxyphenyl)methyl | H | (R) X—CH—Y | 4-(((2-(2-methoxy)ethoxy)ethylamino)-butyl | | aminomethyl |
| 37 | H | H | F | H | H | (S) (4-propoxyphenyl)methyl | H | (S) X—CH—Y | 3-guanidinopropyl | | Aminomethyl |
| 38 | H | H | Cl | H | H | (S) (4-t-butylphenyl)methyl | H | (R) X—CH—Y | 2-(methylsulfonyl)ethyl | | aminomethyl |
| 39 | H | H | Cl | H | H | (S) (4-propoxyphenyl)methyl | absent | (2-S, 4-R) trans-2-aminomethyl-4-hydroxypyrrolidine | | | |
| 40 | H | H | Br | H | H | (S) (4-propoxyphenyl)methyl | absent | (2-S, 4-R) trans-2-aminomethyl-4-hydroxypyrrolidine | | | |
| 41 | H | H | Cl | H | H | (S) (4-propoxyphenyl)methyl | H | (R) X—CH—Y | 2-(methylsulfonyl)ethyl | | aminomethyl |
| 42 | H | H | Br | H | H | (S) (4-propoxyphenyl)methyl | H | (R) X—CH—Y | 2-(methylsulfonyl)ethyl | | aminomethyl |
| 43 | H | H | Br | H | H | (S) (4-ethoxyphenyl)methyl | H | (S) X—CH—Y | 2-aminoethyl | | Aminomethyl |
| 44 | H | H | Cl | H | H | (S) (4-propoxyphenyl)methyl | H | (S) X—CH—Y | 2-aminoethyl | | Aminomethyl |
| 45 | H | H | Br | H | H | (S) (4-propoxyphenyl)methyl | H | (S) X—CH—Y | 2-aminoethyl | | Aminomethyl |
| 46 | H | H | Br | H | H | (S) (4-ethoxyphenyl)methyl | H | (R) X—CH—Y | 3-aminopropyl | | aminomethyl |
| 47 | H | H | Cl | H | H | (S) (4-propoxyphenyl)methyl | H | (R) X—CH—Y | 3-aminopropyl | | aminomethyl |
| 48 | H | H | Br | H | H | (S) (4-propoxyphenyl)methyl | H | (R) X—CH—Y | 3-aminopropyl | | aminomethyl |
| 49 | H | H | Br | H | H | (S) (4-ethoxyphenyl)methyl | H | (R) X—CH—Y | 2-(methylsulfonyl)ethyl | | aminomethyl |
| 50 | H | H | Br | H | H | (S) (4-ethoxyphenyl)methyl | absent | (2-S, 4-R) trans-2-aminomethyl-4-hydroxypyrrolidine | | | |
| 51 | H | H | Cl | H | H | (S) (4-ethoxyphenyl)methyl | H | (S) X—CH—Y | 2-(cyclopropylamino)propyl | | Aminomethyl |
| 52 | H | H | Br | H | H | (S) (4-ethoxyphenyl)methyl | H | (S) X—CH—Y | 2-(cyclopropylamino)propyl | | Aminomethyl |
| 53 | H | H | Br | H | H | (S) (4-ethoxyphenyl)methyl | H | (S) X—CH—Y | 2-(3-methoxypropylamino)propyl | | Aminomethyl |
| 54 | H | H | Br | H | H | (S) (4-ethoxyphenul)methyl | H | (S) X—CH—Y | 2-('4-hydroxypiperidin-1-yl)propyl | | Aminomethyl |
| 55 | H | H | Br | H | H | (S) (4-ethoxyphenyl)methyl | H | (S) X—CH—Y | 2-(2-hydroxy-1,1-dimethylethylamino)-propyl | | Aminomethyl |
| 56 | H | H | Br | H | H | (S) (4-propoxyphenyl)methyl | H | (S) X—CH—Y | 2-(cyclopropylamino)propyl | | Aminomethyl |
| 57 | H | H | Br | H | H | (S) (4-propoxyphenyl)methyl | H | (S) X—CH—Y | 2-(tetrahydrofurfurylamino)propyl | | Aminomethyl |
| 58 | H | H | Br | H | H | (S) (4-propoxyphenyl)methyl | H | (S) X—CH—Y | 2-(tetrahydrofurfurylamino)propyl | | Aminomethyl |
| 59 | H | H | Br | H | H | (S) (4-propoxyphenyl)methyl | H | (S) X—CH—Y | 3-(3-methoxypropylamino)propyl | | Aminomethyl |
| 60 | H | H | Br | H | H | (S) (4-propoxyphenyl)methyl | H | (S) X—CH—Y | 2-(2-hydroxy-1,1-dimethylethylamino)-propyl | | Aminomethyl |
| 61 | H | H | Br | H | H | (S) (4-ethoxyphenyl)methyl | H | (S) X—CH—Y | 2-hydroxyethyl | | Aminomethyl |
| 62 | H | H | Br | H | H | (S) (4-propoxyphenyl)methyl | H | (S) X—CH—Y | 2-('4-hydroxypiperidin-1-yl)ethyl | | Aminomethyl |
| 63 | H | H | Br | H | H | (S) (4-propoxyphenyl)methyl | H | (S) X—CH—Y | 2-(2-hydroxy-1,1-dimethylethylamino)-ethyl | | Aminomethyl |
| 64 | H | H | Br | H | H | (S) (4-ethoxyphenyl)methyl | H | (S) X—CH—Y | 4-(-ethylamino)butyl | | Aminomethyl |
| 65 | H | H | Br | H | H | (S) (4-propoxyphenyl)methyl | H | (S) X—CH—Y | 4-(-ethylamino)butyl | | Aminomethyl |
| 66 | H | H | Br | H | H | (S) (4-ethoxyphenyl)methyl | H | (S) X—CH—Y | 4-(2-methoxyethylamino)butyl | | Aminomethyl |
| 67 | H | H | Br | H | H | (S) (4-propoxyphenyl)methyl | H | (S) X—CH—Y | 4-(2-metnoxyethylamino)butyl | | Aminomethyl |
| 68 | H | H | Br | H | H | (S) (4-ethoxyphenyl)methyl | H | (S) X—CH—Y | 3-(ethylamino)propyl | | Aminomethyl |
| 69 | H | H | Br | H | H | (S) (4-propoxyphenyl)methyl | H | (S) X—CH—Y | 3-(ethylamino)propyl | | Aminomethyl |
| 70 | H | H | Rr | H | H | (S) (4-ethoxyphenyl)methyl | H | (S) X—CH—Y | 3-(2-methoxyethylamino)propyl | | Aminomethyl |
| 71 | H | H | Br | H | H | (S) (4-propoxyphenyl)methyl | H | (S) X—CH—Y | 3-(2-methoxyethylamino)propyl | | Aminomethyl |

TABLE 9

MC-4 Binders

| Pat R1 | Pat R2 | Pat R3 | Pat R4 | Pat R5 | n = | Ring | Pat R6 | Pat R7 | Pat R8 | X | Y |
|---|---|---|---|---|---|---|---|---|---|---|---|
| H | H | Cl | H | H | 1 | Ph | (S) (3,4-dimethoxyphenyl)methyl | H | (S) X—CH—Y | 3-pyridylmethyl | Aminomethyl |
| H | H | Br | H | H | 1 | Ph | (S) (4-trifluoromethlphenyl)methyl | H | (S) X—CH—Y | 3-pyridylmethyl | Aminomethyl |

TABLE 9-continued

MC-4 Binders

| Pat R1 | Pat R2 | Pat R3 | Pat R4 | Pat R5 | n = | Ring | Pat R6 | Pat R7 | Pat R8 | X | Y |
|---|---|---|---|---|---|---|---|---|---|---|---|
| H | H | Cl | H | H | 1 | Ph | (S) (4-trifluoromethlphenyl)methyl | H | (S) X—CH—Y | 3-pyridylmethyl | Aminomethyl |
| H | H | Cl | H | H | 1 | Ph | (S) (4-trifluoromethlphenyl)methyl | H | (S) X—CH—Y | 3-pyridylmethyl | Aminomethyl |
| H | H | Me | H | H | 1 | Ph | (S) (4-trifluoromethlphenyl)methyl | H | (S) X—CH—Y | 3-pyridylmethyl | Aminomethyl |
| H | Cl | H | H | H | 1 | Ph | (S) (4-t-butylphenyl)methyl | H | (S) X—CH—Y | 3-pyridylmethyl | Aminomethyl |
| H | H | Br | H | H | 1 | Ph | (S) (4-t-butylphenyl)methyl | H | (S) X—CH—Y | 3-pyridylmethyl | Aminomethyl |
| H | H | Cl | H | H | 1 | Ph | (S) (4-t-butylphenyl)methyl | H | (S) X—CH—Y | 3-pyridylmethyl | Aminomethyl |
| H | H | Cl | H | H | 1 | Ph | (S) (4-t-butylphenyl)methyl | H | (S) X—CH—Y | 3-pyrldylmethyl | Aminomethyl |
| H | H | Me | H | H | 1 | Ph | (S) (4-t-butylphenyl)methyl | H | (S) X—CH—Y | 3-pyridylmethyl | Aminomethyl |
| Cl | H | Cl | H | H | 1 | Ph | (S) (4-ethoxyphenyl)methyl | H | (S) X—CH—Y | 3-pyridylmethyl | Aminomethyl |
| H | H | Br | H | H | 1 | Ph | (S) (4-propoxyphenyl)methyl | H | (S) X—CH—Y | 3-pyridylmethyl | Aminomethyl |
| H | H | Cl | H | H | 1 | Ph | (S) (4-propoxyphenyl)methyl | H | (S) X—CH—Y | 3-pyridylmethyl | Aminomethyl |
| H | H | Br | H | H | 1 | Ph | (S) (4-methoxyphenyl)methyl | H | (S) X—CH—Y | 3-pyridylmethyl | Aminomethyl |
| H | H | Cl | H | H | 1 | Ph | (S) (4-methoxyphenyl)methyl | H | (S) X—CH—Y | 3-pyridylmethyl | Aminomethyl |
| H | H | CF3 | H | H | 1 | Ph | (S) (4-chlorophenyl)methyl | H | (S) X—CH—Y | 3-guanidinopropyl | Aminomethyl |
| H | H | H | H | H | 0 | CyHex | (S) (4-chlorophenyl)methyl | H | (S) X—CH—Y | 3-guanidinopropyl | Aminomethyl |
| H | H | H | H | H | 1 | CyHex | (S) (4-chlorophenyl)methyl | H | (S) X—CH—Y | 3-guanidinopropyl | Aminomethyl |
| H | H | nAmyl | H | H | 1 | Ph | (S) (4-phenylphenyl)methyl | H | (S) X—CH—Y | 3-guanidinopropyl | Aminomethyl |
| H | H | F | H | H | 1 | Ph | (S) (4-((3-phenylpropylamino)phenyl)methyl | H | (S) X—CH—Y | 3-guanidinopropyl | Aminomethyl |
| H | H | CF3 | H | H | 1 | Ph | (S) (4-chlorophenyl)methyl | H | (S) X—CH—Y | (3-aminomethyl)-phenylmethyl | Aminomethyl |
| H | H | OMe | H | H | 2 | Ph | (S) (4-chlorophenyl)methyl | H | (S) X—CH—Y | (3-aminomethyl)-phenylmethyl | Aminomethyl |
| H | H | OEt | H | H | 2 | Ph | (S) (4-chlorophenyl)methyl | H | (S) X—CH—Y | (3-aminomethyl)-phenylmethyl | Aminomethyl |
| H | H | H | H | H | 0 | CyHex | (S) (4-chlorophenyl)methyl | H | (S) X—CH—Y | (3-aminomethyl) phenylmethyl | Aminomethyl |
| H | H | H | H | H | 1 | CyHex | (S) (4-chlorophenyl)methyl | H | (S) X—CH—Y | (3-aminomethyl) phenylmethyl | Aminomethyl |
| H | H | H | H | H | 2 | Ph | (S) (4-chlorophenyl)methyl | H | (S) X—CH—Y | (3-aminomethyl) phenylmethyl | Aminomethyl |
| H | H | CF3 | H | H | 1 | Ph | (S) (4-ethoxyphenyl)methyl | H | (S) X—CH—Y | (3-aminomethyl) phenylmethyl | Aminomethyl |
| H | Cl | Cl | H | H | 1 | Ph | (S) (4-t-butylphenyl)methyl | absent | (2-S, 4-R) trans-2-aminomethyl-4-hydroxypyrrolidine | | |
| H | H | Cl | H | H | 1 | Ph | (S) (4-t-butylphenyl)methyl | absent | (2-S, 4-R) trans-2-aminomethyl-4-hydroxypyrrolidine | | |
| H | Cl | Cl | H | H | 1 | Ph | (S) (3,4-dimethoxyphenyl)methyl | H | (S) X—CH—Y | 3-aminopropyl | Aminomethyl |
| H | Cl | Cl | H | H | 1 | Ph | (S) (4-trifluoromethlphenyl)methyl | H | (S) X—CH—Y | 3-aminopropyl | Aminomethyl |
| H | H | Cl | H | H | 1 | Ph | (S) (4-trifluoromethlphenyl)methyl | H | (S) X—CH—Y | 3-aminopropyl | Aminomethyl |
| H | H | CF3 | H | H | 1 | Ph | (S) (4-chlorophenyl)methyl | H | (S) X—CH—Y | 3-aminopropyl | Aminomethyl |
| H | H | H | H | H | 1 | CyHex | (S) (4-chlorophenyl)methyl | H | (S) X—CH—Y | 3-aminopropyl | Aminomethyl |
| H | H | Cl | H | H | 2 | Ph | (S) (4-t-butylphenyl)methyl | H | (S) X—CH—Y | 3-aminopropyl | Aminomethyl |
| H | Cl | Cl | H | H | 1 | Ph | (S) (4-t-butylphenyl)methyl | H | (S) X—CH—Y | 3-aminopropyl | Aminomethyl |
| H | H | OCF3 | H | H | 1 | Ph | (S) (4-t-butylphenyl)methyl | H | (S) X—CH—Y | 3-aminopropyl | Aminomethyl |
| H | H | Cl | H | H | 1 | Ph | (S) (4-t-butylphenyl)methyl | H | (S) X—CH—Y | 3-aminopropyl | Aminomethyl |
| H | H | Me | H | H | 1 | Ph | (S) (4-t-butylphenyl)methyl | H | (S) X—CH—Y | 3-aminopropyl | Aminomethyl |
| H | H | Br | H | H | 1 | Ph | (S) (4-methoxyphenyl)methyl | H | (S) X—CH—Y | 3-aminopropyl | Aminomethyl |
| H | H | Cl | H | H | 1 | Ph | (S) (4-methoxyphenyl)methyl | H | (S) X—CH—Y | 3-aminopropyl | Aminomethyl |
| H | Cl | Cl | H | H | 1 | Ph | (S) (4-methoxyphenyl)methyl | H | (S) X—CH—Y | 3-aminoprnpyl | Aminomethyl |
| H | H | Br | H | H | 1 | Ph | (S) (4-methoxyphenyl)methyl | H | (S) X—CH—Y | 3-aminopropyl | Aminomethyl |
| H | H | Cl | H | H | 1 | Ph | (S) (4-methoxyphenyl)methyl | H | (S) X—CH—Y | 3-aminopropyl | Aminomethyl |
| H | H | Cl | H | H | 1 | Ph | (S) (4-methoxyphenyl)methyl | H | (S) X—CH—Y | 3-aminopropyl | Aminomethyl |
| H | H | H | H | H | 1 | CyHex | (S) (4-chlorophenyl)methyl | H | (S) X—CH—Y | 4-aminobutyl | Aminomethyl |
| H | H | Cl | H | H | 2 | Ph | (S) (4-trifluoromethlphenyl)methyl | H | (S) X—CH—Y | 2-methylsulfonylethyl | Aminomethyl |
| H | Cl | Cl | H | H | 1 | Ph | (S) (4-trifluoromethlphenyl)methyl | H | (S) X—CH—Y | 2-methylsulfonylethyl | Aminomethyl |
| H | Cl | H | H | H | 1 | Ph | (S) (4-trifluoromethlphenyl)methyl | H | (S) X—CH—Y | 2-methylsulfonylethyl | Aminomethyl |
| H | H | Cl | H | H | 1 | Ph | (S) (4-trifluoromethlphenyl)methyl | H | (S) X—CH—Y | 2-methylsulfonylethyl | Aminomethyl |
| H | H | Me | H | H | 1 | Ph | (S) (4-trifluoromethlphenyl)methyl | H | (S) X—CH—Y | 2-methylsulfonylethyl | Aminomethyl |
| H | H | Cl | H | H | 2 | Ph | (S) (4-t-butylphenyl)methyl | H | (S) X—CH—Y | 2-methylsulfonylethyl | Aminomethyl |
| H | Cl | H | H | H | 1 | Ph | (S) (4-t-butylphenyl)methyl | H | (S) X—CH—Y | 2-methylsulfonylethyl | Aminomethyl |
| H | H | Cl | H | H | 1 | Ph | (S) (4-t-butylphenyl)methyl | H | (S) X—CH—Y | 2-methylsulfonylethyl | Aminomethyl |
| H | H | Cl | H | H | 1 | Ph | (S) (3-phenylphenyl)methyl | H | (S) X—CH—Y | 2-methylsulfonylethyl | Aminomethyl |
| Cl | H | Cl | H | H | 1 | Ph | (S) (4-ethoxyphenyl)methyl | H | (S) X—CH—Y | 2-methylsulfonylethyl | Aminomethyl |
| H | H | Cl | H | H | 2 | Ph | (S) (4-ethoxyphenyl)methyl | H | (S) X—CH—Y | 2-methylsulfonylethyl | Aminomethyl |
| H | H | Cl | H | H | 2 | Ph | (S) (4-methoxyphenyl)methyl | H | (S) X—CH—Y | 2-methylsulfonylethyl | Aminomethyl |
| H | H | Br | H | H | 1 | Ph | (S) (4-methoxyphenyl)methyl | H | (S) X—CH—Y | 2-methylsulfonylethyl | Aminomethyl |
| H | H | Cl | H | H | 1 | Ph | (S) (4-methoxyphenyl)methyl | H | (S) X—CH—Y | 2-methylsulfonylethyl | Aminomethyl |
| H | H | Cl | H | H | 1 | Ph | (S) (4-I-propylphenyl)methyl | H | (S) X—CH—Y | 2-methylsulfonylethyl | Aminomethyl |
| Cl | H | Cl | H | H | 1 | Ph | (S) (4-ethoxyphenyl)methyl | H | (S) X—CH—Y | methoxymethyl | Aminomethyl |
| H | H | Br | H | H | 1 | Ph | (S) (4-methoxyphenyl)methyl | H | (S) X—CH—Y | methoxymethyl | Aminomethyl |
| H | H | Cl | H | H | 1 | Ph | (S) (4-methoxyphenyl)methyl | H | (S) X—CH—Y | methoxymethyl | Aminomethyl |
| H | H | Cl | H | H | 1 | Ph | (S) (4-ethylphenyl)methyl | H | (S) X—CH—Y | methoxymethyl | Aminomethyl |
| H | H | Cl | H | H | 1 | Ph | (S) (4-I-propylphenyl)methyl | H | (S) X—CH—Y | hydroxymethyl | Aminomethyl |
| H | Cl | Cl | H | H | 1 | Ph | (S) (4-trifluoromethlphenyl)methyl | H | (S) X—CH—Y | hydroxymethyl | Aminomethyl |
| H | H | Br | H | H | 1 | Ph | (S) (4-trifluoromethlphenyl)methyl | H | (S) X—CH—Y | hydroxymethyl | Aminomethyl |

TABLE 9-continued

MC-4 Binders

| Pat R1 | Pat R2 | Pat R3 | Pat R4 | Pat R5 | n = | Ring | Pat R6 | Pat R7 | Pat R8 | X | Y |
|---|---|---|---|---|---|---|---|---|---|---|---|
| H | H | Cl | H | H | 1 | Ph | (S) (4-trifluoromethlphenyl)methyl | H | (S) X—CH—Y | hydroxymethyl | Aminomethyl |
| H | H | Me | H | H | 1 | Ph | (S) (4-trifluoromethlphenyl)methyl | H | (S) X—CH—Y | hydroxymethyl | Aminomethyl |
| H | Cl | Cl | H | H | 1 | Ph | (S) (4-t-butylphenyl)methyl | H | (S) X—CH—Y | hydroxymethyl | Aminomethyl |
| H | H | OCF3 | H | H | 1 | Ph | (S) (4-t-butylphenyl)methyl | H | (S) X—CH—Y | hydroxymethyl | Aminomethyl |
| H | H | Br | H | H | 1 | Ph | (S) (4-t-butylphenyl)methyl | H | (S) X—CH—Y | hydroxymethyl | Aminomethyl |
| H | H | Me | H | H | 1 | Ph | (S) (4-t-butylphenyl)methyl | H | (S) X—CH—Y | hydroxymethyl | Aminomethyl |
| H | H | Cl | H | H | 1 | Ph | (S) (4-phenylphenyl)methyl | H | (S) X—CH—Y | hydroxymethyl | Aminomethyl |
| Cl | H | Cl | H | H | 1 | Ph | (S) (4-ethoxyphenyl)methyl | H | (S) X—CH—Y | hydroxymethyl | Aminomethyl |
| H | H | Cl | H | H | 1 | Ph | (S) (4-ethylphenyl)methyl | H | (S) X—CH—Y | hydroxymethyl | Aminomethyl |
| H | H | Cl | H | H | 1 | Ph | (S) (4-I-propylphenyl)methyl | H | (S) X—CH—Y | hydroxymethyl | Aminomethyl |
| H | H | OEt | H | H | 1 | Ph | (S) (4-iodophenyl)methyl | H | (R) X—CH—Y | 3-aminopropyl | Aminomethyl |
| H | H | H | H | H | 0 | CyHex | (S) (4-iodophenyl)methyl | H | (R) X—CH—Y | 3-aminopropyl | Aminomethyl |
| H | H | H | H | H | 0 | CyHex | (S) (4-ethoxyphenyl)methyl | H | (R) X—CH—Y | 3-aminopropyl | Aminomethyl |
| H | H | Br | H | H | 1 | Ph | (S) (4-ethoxyphenyl)methyl | H | (S) X—CH—Y | propylthiomethyl | Aminomethyl |
| H | H | Br | H | H | 1 | Ph | (S) (4-ethoxyphenyl)methyl | H | (S) X—CH—Y | isopropylthiomethyl | Aminomethyl |
| H | H | Cl | H | H | 1 | Ph | (S) (4-ethoxyphenyl)methyl | H | (S) X—CH—Y | isopropylthiomethyl | Aminomethyl |
| H | H | H | H | H | 1 | CyHex | (S) (4-4-iodophenyl)methyl | H | (S) X—CH—Y | 3-aminopropyl | Aminomethyl |
| H | H | Br | H | H | 1 | Ph | (S) (4-ethoxyphenyl)methyl | H | (S) X—CH—Y | (2,2,2-trifluoroethylthiomethyl | Aminomethyl |
| H | H | Cl | H | H | 1 | Ph | (S) (4-ethoxyphenyl)methyl | H | (S) X—CH—Y | 2-cyclohexylethyl-amiomethyl | Aminomethyl |
| H | H | Br | H | H | 1 | Ph | (S) (3,4-dimethoxyphenyl)methyl | H | (S) X—CH—Y | 2-aminoethyl | Aminomethyl |
| H | H | Cl | H | H | 1 | Ph | (S) (3,4-dimethoxyphenyl)methyl | H | (S) X—CH—Y | 2-aminoethyl | Aminomethyl |
| H | H | Cl | H | H | 2 | Ph | (S) (4-trifluoromethlphenyl)methyl | H | (S) X—CH—Y | 2-dimethylaminoethyl | Aminomethyl |
| H | Cl | Cl | H | H | 1 | Ph | (S) (4-trifluoromethlphenyl)methyl | H | (S) X—CH—Y | 2-dimethylaminoethyl | Aminomethyl |
| H | H | OCF3 | H | H | 1 | Ph | (S) (4-trifluoromethlphenyl)methyl | H | (S) X—CH—Y | 2-dimethylaminoethyl | Aminomethyl |
| H | H | Cl | H | H | 1 | Ph | (S) (4-trifluoromethlphenyl)methyl | H | (S) X—CH—Y | 2-dimethylaminoethyl | Aminomethyl |
| H | H | Me | H | H | 1 | Ph | (S) (4-trifluoromethlphenyl)methyl | H | (S) X—CH—Y | 2-dimethylaminoethyl | Aminomethyl |
| H | H | OCF3 | H | H | 1 | Ph | (S) (4-t-butylphenyl)methyl | H | (S) X—CH—Y | 2-dimethylaminoethyl | Aminomethyl |
| H | H | Br | H | H | 1 | Ph | (S) (4-t-butylphenyl)methyl | H | (S) X—CH—Y | 2-dimethylaminoethyl | Aminomethyl |
| H | H | Cl | H | H | 1 | Ph | (S) (4-t-butylphenyl)methyl | H | (S) X—CH—Y | 2-dimethylaminoethyl | Aminomethyl |
| H | H | Me | H | H | 1 | Ph | (S) (4-t-butylphenyl)methyl | H | (S) X—CH—Y | 2-dimethylaminoethyl | Aminomethyl |
| H | Cl | Cl | H | H | 1 | Ph | (S) (4-methoxyphenyl)methyl | H | (S) X—CH—Y | 2-dimethylaminoethyl | Aminomethyl |
| H | H | Br | H | H | 1 | Ph | (S) (4-methoxyphenyl)methyl | H | (S) X—CH—Y | 2-dimethylaminoethyl | Aminomethyl |
| H | Cl | Cl | H | H | 1 | Ph | (S) (4-ethoxyphenyl)methyl | H | (S) X—CH—Y | 2-dimethylaminoethyl | Aminomethyl |
| H | H | Me | H | H | 1 | Ph | (S) (4-ethoxyphenyl)methyl | H | (S) X—CH—Y | 2-dimethylaminoethyl | Aminomethyl |
| H | H | Cl | H | H | 2 | Ph | (S) (4-methoxyphenyl)methyl | H | (S) X—CH—Y | 2-dimethylaminoethyl | Aminomethyl |
| H | Cl | Cl | H | H | 1 | Ph | (S) (4-methoxyphenyl)methyl | H | (S) X—CH—Y | 2-dimethylaminoethyl | Aminomethyl |
| H | H | OCF3 | H | H | 1 | Ph | (S) (4-methoxyphenyl)methyl | H | (S) X—CH—Y | 2-dimethylaminoethyl | Aminomethyl |
| H | H | Cl | H | H | 1 | Ph | (S) (4-((3-pyridyl)methylamino)phenyl)methyl | | | | |

Another assay useful for identifying or characterizing MC receptor ligands measures signaling of MC receptors. MC receptors are G protein-coupled receptors that couple to adenylate cyclase and produce cAMP. Therefore, measuring cAMP production in a cell expressing a MC receptor and treated with a MC receptor ligand can be used to assess the function of the MC receptor ligand in activating a MC receptor. One method for measuring cAMP production in cells expressing a MC receptor ligand and treated with a triamine derivative of the invention is described in Example V. A variety of triamine derivatives that can activate MC receptors are shown in Tables 4 and 5.

The invention also relates to pharmaceutical compositions comprising a MC receptor ligand such as a triamine derivative and a pharmaceutically acceptable carrier. The term "composition", as in pharmaceutical composition, is intended to encompass a product comprising at least one active ingredient, and at least one inert ingredient making up the carrier, as well as any product which results, directly or indirectly, from combination of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the MC receptor ligand or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the MC receptor ligand and on the particular physico-chemical characteristics of the specific MC receptor ligand.

The effective dosage of active ingredient employed may vary depending on the particular compound employed, the mode of administration, the condition being treated and the severity of the condition being treated Such dosage may be ascertained readily by a person skilled in the art.

The invention further relates to methods of administering a pharmaceutical composition comprising an MC receptor ligand such as a triamine derivative to a subject in order to restrain pathologically elevated cytokine activity in the subject, to treat inflammation or to treat obesity. For example, a triamine derivative can be administered to a subject as a treatment for inflammation, pain, obesity, cachexia, sexual dysfunction or syndrome X. As used herein, "syndrome X" is a set of conditions that result from or are associated with being overweight; such set of conditions can include diabetes, high blood pressure, atherosclerosis, stroke and heart disease.

The invention also relates to methods of administering a pharmaceutical composition comprising an MC receptor ligand such as a triamine derivative to a subject in order to enhance a cytokine activity that restrains pathologically elevated cytokine activity in a subject. For example, IL-10 is known to decrease the activity of certain pathologically elevated cytokines such as TNF-α, IL-1, IL-6 and IL-8 (Platzer et al., *International Immunol.* 7:517–523 (1995)). A normal range of IL-10 activity present in a specific tissue can be determined by sampling a statistically significant number of normal, healthy subjects in the population. A triamine derivative is administered to increase IL-10 activity above the normal range in order to restrain pathologically elevated cytokine activity. In particular, IL-10 cytokine activity is increased at least about one standard deviation above the normal, and can be two standard deviations or greater above the normal range.

A pharmaceutical composition comprising an MC receptor ligand such as a triamine derivative can be administered to a subject having pathologically elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An MC receptor ligand also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vols. I to III, 2nd ed., CRC Press, Boca Raton, Fla. (1993), which is incorporated herein by reference). Liposomes, for example, which consist of phospholipids or other lipids, are nontoxic, physiologically acceptable and metabolizable carriers that are relatively simple to make and administer.

Since cytokine expression can be localized or systemic, one skilled in the art would select a particular route and method of administration of a triamine derivative based on the source and distribution of cytokines in a subject. For example, in a subject suffering from a systemic condition such as bacterial endotoxin-induced sepsis, a pharmaceutical composition comprising a triamine derivative can be administered intravenously, orally or by another method that distributes the compound systemically. However, in a subject suffering from a pathology caused by localized cytokine expression such as acute respiratory distress syndrome, a triamine derivative can be suspended or dissolved in the appropriate pharmaceutically acceptable carrier and administered directly into the lungs using a nasal spray or other inhalation device.

In order to restrain the biological activity of a cytokine, for example, a triamine derivative must be administered in an effective dose, which is about 0.0001 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a triamine derivative required to obtain an effective dose in a subject depends on many factors including the age and general health of the subject as well as the route of administration and the number of treatments to be administered. In view of these factors, the skilled artisan would adjust the particular dose so as to obtain an effective dose for altering the activity of a MC receptor.

Triamine derivative compounds of the present invention may be used in combination with other drugs that are used in the treatment, prevention, suppression or amelioration of the diseases or conditions for which such compounds are useful. Such other drugs may be administered, by a route and in an amount commonly used therefor, contemporaneously or sequentially with a triamine derivative compound of the present invention. When such a triamine derivative compound is used contemporaneously with one or more other drugs, a pharmaceutical compositions of the present invention include those that also contain one or more other active ingredients in addition to a triamine derivative compound of the present invention. Examples of other active ingredients that may be combined with a triamine derivative compound of the present invention, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) α-glucosidase inhibitors (such as acarbose);

(e) cholesterol lowering agents such as (i) HMG-CoA reductase inhibitors (lovastatin, simbastatin and pravastatin, fluvastatin, atorvastatin, and other statins), (ii) sequestrants (cholestyramine, colestipos and a dialkylaminoalkyl derivatives of a cross-linked dextran), (ii) nicotinyl alcohol nicotinic acid or a salt thereof, (iii) proliferator-activator receptor α agonists such as fenofibric acid derivatives (gemfibrozil, clofibrat, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E and (vii) thyromimetics;

(f) PPARδ agonists such as those disclosed in WO97/28149;

(g) anti-obesity compounds such as fenfluramine, dexfenfluramine, phentermine, sibutramine, orlistat, or β3 adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579;

(j) PPARγ antagonists such as described in WO 97/10813;

(k) serotonin reuptake inhibitors such as fluoxetine and sertraline;

(l) growth hormone secretagogues such as MK-0677;

(m) agents useful in the treatment of male or female sexual dysfunction such as phosphodiester V inhibitors such as sildenafil, and α-2 adrenergic receptor antagonists; and (n) CCK agonists useful in the reduction of feeding such as SR146131, or the CCK agonists described in U.S. Pat. Nos. 5,859,007; 5,795,887; 5,731,340; 5,656,648; 5,889,182; 5,739,129; 5,508,432; 5,646,140; or 5,534,530.

The following examples are intended to illustrate but not limit the invention.

EXAMPLE I

This example provides methods for the synthesis of combinatorial libraries of the present invention.

Method 1

General Protocol

Step 1. Peptide Synthesis

Solid phase syntheses were carried out using the "tea-bag" methodology in which the resin is contained within polypropylene mesh packets. 100 mg p-methylbenzhydrylamine (MBHA) resin (1.3 meq/g, 100–200 mesh) was neutralized by three 5 mL washes with 5% diisopropylethylamine (DIEA) in dichloromethane (DCM). Excess DIEA was removed by three 5 mL DCM washes. The first amino acid was coupled by adding the resin packet to a solution of the N-a-tBoc protected amino acid (0.2M, 6×) and hydroxybenzotriazole (HOBt), 6×) in dimethyl formamide (DMF), followed by the addition of 0.2M diisopropylcarbodiimide (DIC, 6×) in DCM (see Step 1 of FIG. 1).

The first amino acid can be non-cyclic, resulting in a triamine of the invention where $R_7$ is present and $R_8$ is the formula X—CH—Y, as discussed above. When the non-cylic amino acid is N-alkylated, it results in $R_7$ being an alkyl.

Alternatively, a cyclic amino acid can be used, resulting in $R_7$ being absent and $R_8$ and the adjacent nitrogen of the above depicted formula forming a heterocycle or substituted heterocycle, as discussed above. Commercially available cyclic amino acids such as, for example, proline, hydroxyproline, thioproline or tetrahydroisoquinoline carboxylate can be used. In addition, both cyclic and non-cyclic amino acids can be made and are known to those skilled in the art.

Non-commercial amino acids can be prepared off resin from commercially available amino acids and used in this synthesis. For example the available N-BOC-O-allyl tyrosine can be hydrogenated by following the example by Fraile et al., *Tetrahedron Asymmetry*, 7:2263–2276 (1996), to produce the N-BOC-O-propyl tyrosine, which can be incorporated into the solid phase synthesis. Cyclic derivatives can also be prepared off resin and incorporated in the syntheis. For example, 4-substituted proline derivatives can be prepared following the examples provided by Williams et al., *J Org Chem*, 59: 3616–3625 (1994); Hudlicky, M., *J Fluorine Chem*, 60:193–210 (1993); and Tanaka et al., *Tetrahedron: Asymmetry*, 9: 71–77 (1998). For examples of methods for thiazolidine S,S dioxide amino acids see Mata, E. G., *Tetrahedron Lett*, 38:6335–6338 (1997); and Patek et al., *Tetrahedron Lett*, 36:2227–2230 (1995).

The coupling reaction was allowed to proceed for 2 h. The reaction solution was removed and the resin was washed once with 5 mL DMF, and once with 5 mL DCM. The N-a-tBoc protecting group was removed by washing the packet twice for 30 minutes with trifluoroacetic acid (TFA) in DCM. Excess TFA was removed by washing the packet twice with isopropanol, and twice with 5 mL DCM (see Step 2 of FIG. 1).

The resin-bound TFA salt was then neutralized, washed, and a second amino acid added in a manner identical to the first (see Step 3 of FIG. 1). Following removal of the second N-a-tBoc protecting group (see Step 4 of FIG. 1), the resulting dipeptide was then N-acylated by adding the resin packet to a solution of the carboxylic acid (0.2M, 6×) and HOBt (6×)(see Step 5 of FIG. 1). DCI (0.2M in DCM, 6×) was then added and the coupling reaction allowed to proceed for 2 h at room temperature. The resin was then washed once with 5 mL DMF and once with 5 mL DCM.

As shown at Step 5 of FIG. 1, phenylacetic acid derivatives were coupled to make compounds of the invention. However, cyclohexylacetic acid derivatives were also used to make compounds of the invention, resulting in a cyclohexyl ring in the formula of the invention.

Step 2. Exhaustive Reduction

The exhaustive reduction of the three backbone functionalities of the N-acylated dipeptide (as well as any reducible side chain functionalities) was carried out in 50 mL glass conical tubes under nitrogen (see Step 6 of FIG. 1). To each tube was added the resin packet (0.13 meq resin, 100 mg of starting resin, 0.24 meq carbonyl) and boric acid (234 mg, 15×). Trimethylborate (0.416 mL. 15×) was added, followed by the slow addition of 10.8 mL borane-THF complex (1M, 45×). Following cessation of hydrogen evolution, the capped tubes were heated at 65° C. for 72 h in a heating block. Following decantation of the reaction solution (quenched by the slow addition to isopropanol), the resin packet was washed three times with 5 mL methanol, once with 5 mL tetrahydrofuran and twice with 5 mL piperidine. The amine-borane complex was then disproportionated by overnight treatment with 10 mL piperidine (400×) at 65° C. Following decantation of the resulting piperidine-borane solution, the resin packet was washed twice with 5 mL DCM and twice with methanol. The resin was then dried under high vacuum.

Alternatively, the reduction was carried out with 10 mL 1M borane methylsulfide complex in dioxane at reflux for 24 hours. The steps for decantation, washing, piperidine treatment and washing remain the same.

Step 3: Resin Cleavage

The triamines were cleaved from resin by treatment with anhydrous HF, in the presence of 5% anisole, at 0° C. for 9 h (see Step 7 of FIG. 1). The desired products were obtained following extraction from acetonitrile/water (1/1, 2×5 mL) and lyophilization.

Method 2

Protocol for Synthesis of Group X of R8 Dimethylamine-triamine

Solid phase syntheses were carried out using the "tea-bag" methodology in which the resin is contained within polypropylene mesh packets. 100 mg MBHA resin (1.3 meq/g, 100–200 mesh) was neutralized by three 5 mL washes with 5% DIEA in DCM. Excess DIEA was removed by three 5 mL DCM washes.

Figure 2:
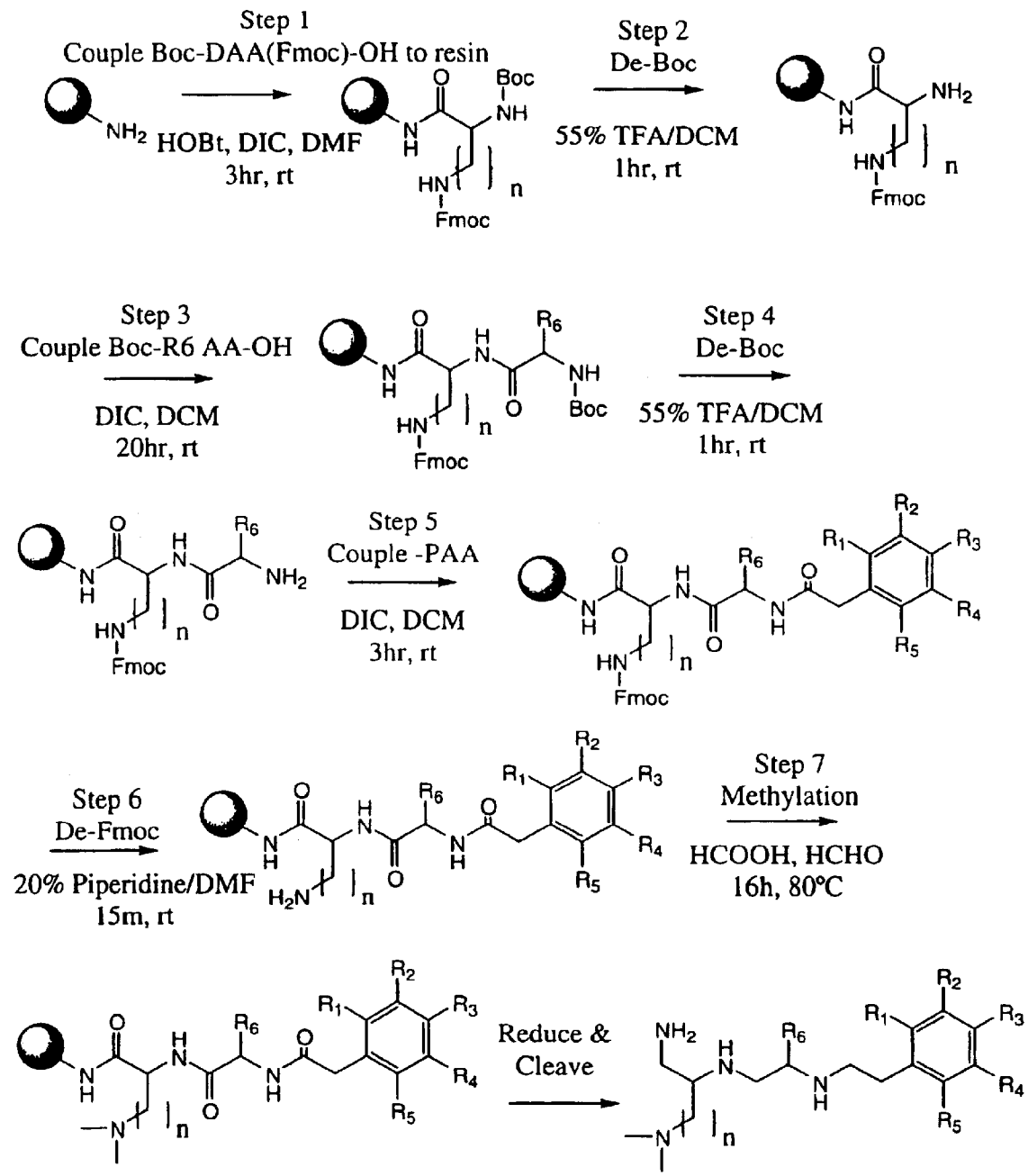
FIG. 2 shows a more specific reaction scheme for synthesis of triamine derivatives, wherein the $R_7$ and $R_8$ groups are further delineated.

Step 1: Coupling α-Boc-Diamino Acid-amino-terminal-Fmoc-OH to Resin (See Step 1 of FIG. 2).

The resin packet was added to a solution of α-Boc-diamino(Fmoc)-OH (0.2M, 6×) and HOBt (0.2M, 6×) in DMF, followed by the addition of DIC (0.2M, 6×) in DCM. The coupling reaction was allowed to proceed for 2 h. The reaction solution was removed and the resin was washed once with 5 mL DMF, and once with 5 mL DCM.

Step 2: Removal of Boc Group (See Step 2 of FIG. 2).

The N-a-tBoc protecting group was removed by washing the packet twice for 30 minutes with 55%TFA/DCM. Excess TFA was removed by washing the packet twice with 5 mL IPA, twice with 5 mL DCM, twice with 5 mL 5%DIEA/DCM and twice with 5 mL DCM.

Step 3: Addition of Boc-Tyr(OEt)-OH (See Step 3 of FIG. 2).

The resin packet was added to a solution of Boc-Lys(OEt)-OH (0.1M, 6×) and DIC (0.1M, 6×) in DCM. The coupling reaction was allowed to proceed for 20 h. The reaction solution was removed and the resin was washed once with 5 mL DMF, and once with 5 mL DCM. The switch to DCM and exclusion of HOBt was to avoid any Fmoc deprotection.

Step 4: Removal of Boc Group (See Step 4 of FIG. 2).

The N-a-tBoc protecting group was removed by washing the packet twice for 30 minutes with 55% TFA/DCM. Excess TFA was removed by washing the packet twice with 5 mL IPA, twice with 5 mL DCM, twice with 5 mL 5%DIEA/DCM and twice with 5 mL DCM.

Step 5: Addition of 4-chlorophenylacetic Acid (See Step 5 of FIG. 2).

The resin packet was added to a solution of 4-chlorophenylacetic acid (0.1M, 6×) and DIC (0.1M, 6×) in DCM. The coupling reaction was allowed to proceed for 3 h. The reaction solution was removed and the resin was washed once with 5 mL DMF, and once with 5 mL DCM.

Step 6: Removal of Fmoc Group (See Step 6 of FIG. 2).

The N-b-Fmoc protecting group was removed by washing the packet for 30 minutes with 20% piperidine/DMF. The packet was washed three times with 5 mL DMF, three times with 5 mL DCM, and once with 5 mL MeOH.

Step 7: Methylation (See Step 7 of FIG. 2).

The resin packet was added to a mixture of formaldehyde (10 mL; 37%aq) and formic acid (5 mL) and heated at 80° C. for 20 hours. After cooling to room temp the packet was washed twice with 5 mL methanol, twice with 5 mL DCM and once with methanol.

In an alternate procedure, the resin packet was added to a mixture of formaldehyde (10 mL) and formic acid (2.5 mL) and heated at 80° C. for 2 hours. A further portion of formic acid (2.5 mL) was added and the mixture heated for a further 18 hours.

Step 8: Reduction (See Last Step of FIG. 2).

The reduction was carried out in 50 mL glass conical tubes under nitrogen. To each tube was added the resin packet (0.13 meq resin, 100 mg of starting resin, 0.24 meq carbonyl) and boric acid (234 mg, 15×). Trimethylborate (0.416 mL, 15×) was added, followed by the slow addition of 10.8 mL borane-THF complex (1M, 45×). Following cessation of hydrogen evolution, the capped tubes were heated at 65° C. for 72 h in a heating block. Following decantation of the reaction solution (quenched by the slow addition to isopropanol), the resin packet was washed three times with 5 mL methanol, once with 5 mL THF and twice with 5 mL piperidine. The amine-borane complex was then disproportionated by overnight treatment with 10 mL piperidine (400×) at 65° C. Following decantation of the resulting piperidine-borane solution, the resin packet was washed twice with 5 mL DCM and twice with methanol. The resin was then dried under high vacuum.

Alternatively, the reduction was carried out with 10 mL 1M borane methylsulfide complex in dioxane at reflux for 24 hours. The steps for decantation, washing, piperidine treatment and washing remain the same.

Step 9: Cleavage (See Last Step of FIG. 2).

The triamines were cleaved from resin by treatment, in the presence of 5% anisole, with anhydrous gas HF at room temperature or anhydrous liquid HF at 0° C. for 9 h. The desired products were obtained following extraction from acetonitrile/water (1/1, 2×5 mL) and lyophilization.

Method 3

Protocol for Synthesis of Group X of R8 Providing Monosubstituted Alkylaminoalkyl Following method 2, as described above, except modifying step 7, as described below.

Step 7: Acylation Providing Group X

The resin packet was added to a solution of a carboxylic acid (0.2M, 6×) and HOBt (0.2M, 6×) in DMF, followed by the addition of DIC (0.2M, 6×) in DCM. The coupling reaction was allowed to proceed for 2 h. The reaction solution was removed and the resin was washed once with 5 mL DMF, and once with 5 mL DCM.

Step 7: Sulfonation Providing Group X

Alternatively, the resin packet was added to a solution of a sulfonyl chloride (0.2M, 6×), base (N-methyl imidazole or N-methyl morpholine (0.2M)) in DMF. The coupling reaction was allowed to proceed for 2 h. The reaction solution was removed and the resin was washed once with 5 mL DMF, and once with 5 mL DCM.

Method 4

Protocol for Synthesis of Group X of R8 Providing Dialkylaminoalkyl

Solid phase syntheses were carried out using the "tea-bag" methodology in which the resin is contained within polypropylene mesh packets. 150 mg MBHA resin (1.3 meq/g, 100–200 mesh) was neutralized by three 5 mL washes with 5% DIEA in DCM. Excess DIEA was removed by three 5 mL DCM washes.

Figure 3:
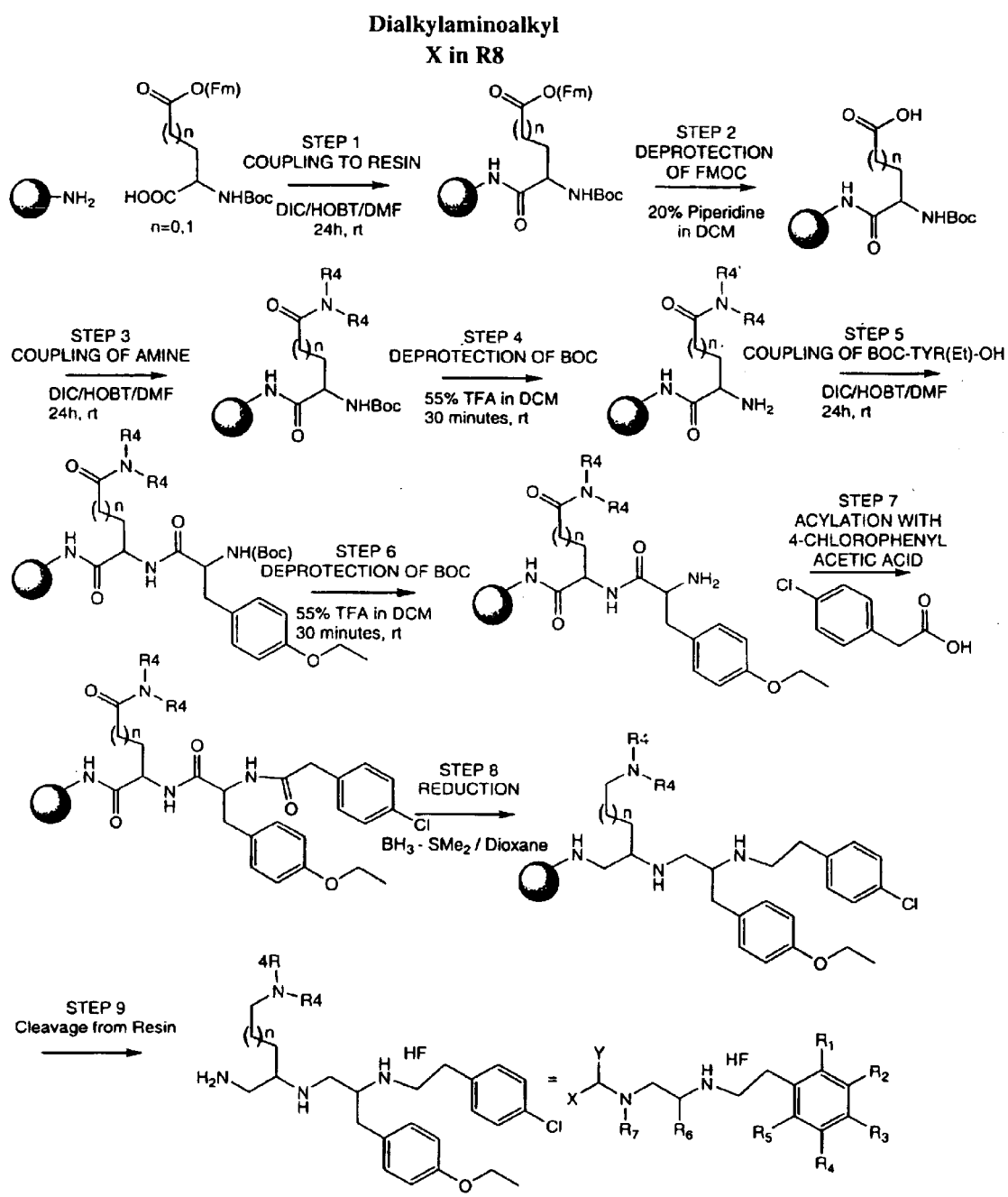
FIG. 3 shows another more specific reaction scheme for synthesis of triamine derivatives, wherein the $R_7$ and $R_8$ groups are further delineated.

Step 1: Couple Boc-aspartic Acid(β-Fmoc)-OH to Resin (See Step 1 of FIG. 3).

The resin packet was added to a solution of Boc-Asp(Fmoc)-OH (0.1M, 3×) and HOBt (0.1M, 3×) in DMF, followed by the addition of DIC to make 0.1M. The a coupling reaction was allowed to proceed for 24 hr. The reaction solution was removed and the resin was washed three times with 5 mL DMF, and three times with 5 mL DCM.

Step 2: Removal of Fmoc Group (See Step 2 of FIG. 3).

The β-carboxy-Fmoc protecting group was removed by washing the packet for 2 hrs with 20% piperidine/DCM. The packet was washed three times with 1% acetic acid in DCM, then three times with 5 mL DCM.

Step 3: Addition of Secondary Amine to the β-carboxy Group (See Step 3 of FIG. 3).

The Boc-Asp on resin was treated with HOBt (0.1M, 5×) and the secondary amine(0.1M, 5×) in DMF, followed by the addition of DIC (0.1M, 5×), and the reaction allowed to progress overnight. The packet was washed three times with 5 mL DMF, three times with 5 mL DCM.

Step 4: Removal of Boc Group (See Step 4 of FIG. 3).

The N-α-tBoc protecting group was removed by washing the packet for 30 minutes with 55%TFA/DCM. Excess TFA was removed by washing the packet twice with 5 mL DCM, twice with 5 mL 5%DIEA/DCM and twice with 5 mL DCM.

Step 5: Addition of Boc-Tyr(Et)-OH (See Step 5 of FIG. 3).

The resin packet was added to a solution of Boc-Try(Et)-OH (0.1M, 3×) and HOBt (0.1M, 3×) in DMF, followed by the addition of DIC (0.1M, 3×). The coupling reaction was allowed to proceed for 20 h. The reaction solution was removed and the resin was washed three times with 5 mL DMF, and three times with 5 mL DCM.

Step 6: Removal of Boc Group (See Step 6 of FIG. 3).

The N-a-tBoc protecting group was removed by washing the packet for 30 minutes with 55% TFA/DCM. Excess TFA was removed by washing the packet twice with 5 mL DCM, twice with 5 mL 5%DIEA/DCM and twice with 5 mL DCM.

Step 7: Addition of 4-chlorophenylacetic Acid (See Step 7 of FIG. 3).

The resin packet was added to a solution of 4-chlorophenylacetic acid (0.1M, 3×), and HOBT(0.1M, 3×) followed by DIC (0.1M, 6×). The coupling reaction was allowed to proceed overnight. The reaction solution was removed and the resin was washed three times with 5 mL DMF, and three times with 5 mL DCM.

Step8: Reduction (See Step 8 of FIG. 3).

Resin in tea bags were suspended in anhydrous dioxane (40 mL/mmole resin) under nitrogen, and BH3/Me2S(45 equiv. (final concentration ~1.0M) was added. The mixture was heated to reflux for 24 hours, then cooled to room temperature. The solution was poured into methanol, and the tea bags were washed with THF and then treated with methanol for 10 minutes.

The resin packets where then washed three times with 5 mL methanol, once with 5 mL THF and twice with 5 mL piperidine. The amine-borane complex was then disproportionated by overnight treatment with 10 mL piperidine (400×) at 65° C. Following decantation of the resulting piperidine-borane solution, the resin packet was washed twice with 5 mL DCM and twice with methanol. The resin was then dried under high vacuum.

Step9: Cleavage (See Step 9 of FIG. 3).

The triamines were cleaved from resin by treatment with anhydrous gas HF at 20° C.; or liquid HF, in the presence of 5% anisole, at 0° C. for 9 h. The desired products were obtained following extraction from acetonitrile/water (1/1, 2×5 mL) and lyophilization.

Based on these methods of synthesis, the following libraries and single compounds listed in Table 10 below were made, as designated by their R1 to R3 starting materials. Note that the R3 carobxylic acid starting material corresponds to the phenyl ring (and R1 to R5 phenyl substituents) of the claimed invention; the side chain of the R2 amino acid starting material corresponds to R6 of the claimed invention; and the side chain of the R1 amino acid starting material corresponds to R8 of the claimed invention (see equivalence at the bottom of FIG. 1). Where R4 is listed (i.e., where it is not blank or hydrogen), it is a further modification of the R1 amino acid side chain and, therefore, contributes to R8 of the claimed invention (see, for example, step 7 of FIG. 2 and step 3 of FIG. 3).

| | | | | | | |
|---|---|---|---|---|---|---|
| | | | 6635 | | | |
| 32 | Boc-ASP (OFm)-OH | Boc-TYR (Et)—OH | 4-bromophenylacetic acid | cyclopropylamine | 503 | 38.3 |
| 33 | Boc-ASP (OFm)-OH | Boc-TYR (Et)—OH | 4-bromophenylacetic acid | tetrahydrofurfurylamine | 547 | 49.6 |
| 34 | Boc-ASP (OFm)-OH | Boc-TYR (Et)—OH | 4-bromophenylacetic acid | N-methylcyclohexylamine | 559 | 47.9 |
| 35 | Boc-ASP (OFm)-OH | Boc-TYR (Et)—OH | 4-bromophenylacetic acid | 3-methoxypropylamine | 535 | 37.9 |
| 36 | Boc-ASP (OFm)-OH | Boc-TYR (Et)—OH | 4-bromophenylacetic acid | 4-hydroxypiperidine | 547 | 46.3 |
| 37 | Boc-ASP (OFm)-OH | Boc-TYR (Et)—OH | 4-bromophenylacetic acid | 2-amino-2-methyl-1-propanol | 535 | 40.2 |
| 38 | Boc-ASP (OFm)-OH | Boc-TYR (Et)—OH | 4-bromophenylacetic acid | 2-(methylamino)ethanol | 521 | 41 |
| 39 | Boc-ASP (OFm)-OH | Boc-TYR (Pr)—OH | 4-bromophenylacetic acid | morpholine | 547 | 53 |
| 40 | Boc-ASP (OFm)-OH | Boc-TYR (Pr)—OH | 4-bromophenylacetic acid | cyclopropylamine | 517 | 38.7 |
| 41 | Boc-ASP (OFm)-OH | Boc-TYR (Pr)—OH | 4-bromophenylacetic acid | tetrahydrofurfurylamine | 561 | 46.6 |
| 42 | Boc-ASP (OFm)-OH | Boc-TYR (Pr)—OH | 4-bromophenylacetic acid | N-methylcyclohexylamine | 573 | 44.9 |
| 43 | Boc-ASP (OFm)-OH | Boc-TYR (Pr)—OH | 4-bromophenylacetic acid | 3-methoxypropylamine | 549 | 40.2 |
| 44 | Boc-ASP (OFm)-OH | Boc-TYR (Pr)—OH | 4-bromophenylacetic acid | 4-hydroxypiperidine | 561 | 43.6 |
| 45 | Boc-ASP (OFm)-OH | Boc-TYR (Pr)—OH | 4-bromophenylacetic acid | 2-amino-2-methyl-1-propanol | 549 | 38.3 |
| 46 | Boc-ASP (OFm)-OH | Boc-TYR (Pr)—OH | 4-bromophenylacetic acid | 2-(methylamin)ethanol | 535 | 44.1 |

-continued

6635

| | R1 | R2 | R3 | R4 | MH+ | % |
|---|---|---|---|---|---|---|
| 47 | Boc-LYS (Fmoc)-OH | Boc-TYR (Et)—OH | 4-bromophenylacetic acid | Acetic acid | 519 | 95.6 |
| 48 | Boc-LYS (Fmoc)-OH | Boc-TYR (Pr)—OH | 4-bromophenylacetic acid | Acetic acid | 533 | 89.4 |
| 49 | Boc-LYS (Fmoc)-OH | Boc-TYR (Et)—OH | 4-bromophenylacetic acid | 2-(2-methoxyethoxy)acetic acid | 593 | 89.5 |
| 50 | Boc-LYS (Fmoc)-OH | Boc-TYR (Pr)—OH | 4-bromophenylacetic acid | 2-(2-methoxyethoxy)acetic acid | 607 | 77.5 |
| 51 | Boc-ORN (Fmoc)-OH | Boc-TYR (Et)—OH | 4-bromophenylacetic acid | Acetic acid | 505 | 82.2 |
| 52 | Boc-ORN (Fmoc)-OH | Boc-TYR (Pr)—OH | 4-bromophenylacetic acid | Acetic acid | 519 | 80.8 |
| 53 | Boc-ORN (Fmoc)-OH | Boc-TYR (Et)—OH | 4-bromophenylacetic acid | 2-(2-methoxyethoxy)acetic acid | 579 | 98.9 |
| 54 | Boc-ORN (Fmoc)-OH | Boc-TYR (Pr)—OH | 4-bromophenylacetic acid | 2-(2-methoxyethoxy)acetic acid | 593 | 87.4 |
| 53 | Boc-ORN (Fmoc)-OH | Boc-TYR (Et)—OH | 4-bromophenylacetic acid | 2-(2-methoxyethoxy)acetic acid | 579 | 98.9 |

6600 TRG6600

| Cmp | R1 | R2 | R3 | MH+ |
|---|---|---|---|---|
| 1 | Fmoc-L-Arg (Tos) | Fmoc-L-p-I-phenylalanine | Phenylacetic acid | 523 |
| 2 | Fmoc-L-Arg (Tos) | Fmoc-L-p-I-phenylalanine | 4-Ethoxyphenylacetic acid | 567 |
| 3 | Fmoc-L-Arg (Tos) | Fmoc-L-p-I-phenylalanine | 4-Chlorophenylacetic acid | 558 |
| 4 | Fmoc-L-Arg (Tos) | Fmoc-L-p-I-phenylalanine | 4-(Trifluoromethyl)-phenylacetic acid | 591 |
| 5 | Fmoc-L-Arg (Tos) | Fmoc-L-p-I-phenylalanine | 3,4-(Methylenedioxy)-phenylacetic acid | 567 |
| 7 | Fmoc-L-Arg (Tos) | Fmoc-L-Tyrosine (OEt) | 4-Chlorophenylacetic acid | 476 |
| 8 | Fmoc-L-Arg (Tos) | Fmoc-L-Tyrosine (OEt) | 4-(Trifluoromethyl)-phenylacetic acid | 509 |
| 9 | Fmoc-L-Arg (Tos) | Fmoc-L-Tyrosine (OEt) | 4-Nitrophenylacetic acid | 486 |
| 10 | Fmoc-L-Arg (Tos) | Fmoc-L-Tyrosine (OEt) | 3,5-Difluorophenylacetic acid | 477 |
| 13 | Fmoc-L-Arg (Tos) | Fmoc-L-Tyrosine (OEt) | 2-Naphthylacetic acid | 491 |
| 15 | Fmoc-L-Arg (Tos) | Fmoc-L-Tyrosine (OEt) | Cyclohexane-carboxylic acid | 433 |
| 19 | Fmoc-D-Arg (Tos) | Fmoc-D-Tyrosine (OEt) | 4-Ethoxyphenylacetic acid | 485 |
| 22 | Fmoc-D-Arg (Tos) | Fmoc-D-Tyrosine (OEt) | Cyclohexane-carboxylic acid | 433 |
| 23 | Fmoc-D-Arg (Tos) | Fmoc-D-p-I-phenylalanine | Phenylacetic acid | 523 |

-continued

6600 TRG6600

| Cmp | R1 | R2 | R3 | MH+ | |
|---|---|---|---|---|---|
| 24 | Fmoc-D-Arg (Tos) | Fmoc-D-p-I-phenylalanine | 3-Fluorophenylacetic acid | 541 | 7.4 |
| 26 | Fmoc-D-Arg (Tos) | Fmoc-D-p-I-phenylalanine | Cyclohexylacetic acid | 529 | 5.5 |
| 28 | Fmoc-D-Arg (Tos) | Fmoc-D-Tyrosine (OEt) | 4-Fluorophenylacetic acid | 459 | 2.6 |
| 29 | Fmoc-D-Arg (Tos) | Fmoc-L-p-I-phenylalanine | 4-Fluorophenylacetic acid | 541 | 6.6 |
| 30 | Fmoc-D-Arg (Tos) | Fmoc-D-p-I-phenylalanine | 4-Fluorophenylacetic acidp | 541 | 9.8 |

6601

| 6601 # | R1 Amino Acid | R2 Amino Acid | R3 Carboxylic acid | MW | Amt mg |
|---|---|---|---|---|---|
| 6 | Fmoc-L-Arg (Tos) | Fmoc-L-p-I-Phe | 3-Fluorophenylacetic acid | 541 | 54.9 |
| 7 | Fmoc-L-Arg (Tos) | Fmoc-L-p-I-Phe | 4-Biphenylacetic acid | 599 | 63.5 |
| 8 | Fmoc-L-Arg (Tos) | Fmoc-L-p-I-Phe | 3,4-Dimethoxyphenylacetic acid | 583 | 52 |
| 10 | Fmoc-L-Arg (Tos) | Fmoc-L-p-I-Phe | 3,5-Difluorophenylacetic acid | 559 | 58.2 |
| 15 | Fmoc-L-Arg (Tos) | Fmoc-L-p-I-Phe | Cyclohexylacetic acid | 529 | 62.3 |

-continued

6601

| 6601 # | R1 Amino Acid | R2 Amino Acid | R3 Carboxylic acid | MW | Amt mg |
|---|---|---|---|---|---|
| 30 | Fmoc-D-Arg (Tos) | Fmoc-D-Tyr (OEt) | Phenylacetic acid | 441 | 27.2 |
| 31 | Fmoc-D-Arg (Tos) | Fmoc-D-Tyr (OEt) | 3-Fluorophenylacetic acid | 459 | 28.5 |
| 32 | Fmoc-D-Arg (Tos) | Fmoc-D-Tyr (OEt) | 4-Biphenylacetic acid | 517 | 28.4 |
| 33 | Fmoc-D-Arg (Tos) | Fmoc-D-Tyr (OEt) | 4-Chlorophenylacetic acid | 476 | 27.1 |
| 34 | Fmoc-D-Arg (Tos) | Fmoc-D-Tyr (OEt) | 4-(Trifluoromethyl)-phenylacetic acid | 509 | 29.6 |
| 35 | Fmoc-D-Arg (Tos) | Fmoc-D-Tyr (OEt) | 3,4-Dimethoxyphenylacetic acid | 501 | 30.8 |

-continued

6601

| 6601 # | R1 Amino Acid | R2 Amino Acid | R3 Carboxylic acid | MW | Amt mg |
|---|---|---|---|---|---|
| 37 | Fmoc-D-Arg (Tos) | Fmoc-D-Tyr (OEt) | 3,5-Difluorophenylacetic | 477 | 31.7 |
| 55 | Fmoc-D-Arg (Tos) | Fmoc-D-p-I-Phe | 4-Biphenylacetic acid | 599 | 12 |
| 56 | Fmoc-D-Arg (Tos) | Fmoc-D-p-I-Phe | 4-Ethoxyphenylacetic acid | 567 | 10.8 |
| 57 | Fmoc-D-Arg (Tos) | Fmoc-D-p-I-Phe | 4-Chlorophenylacetic acid | 558 | 12.6 |
| 58 | Fmoc-D-Arg (Tos) | Fmoc-D-p-I-Phe | 4-(Trifluoromethyl)-phenylacetic acid | 591 | 17.4 |
| 59 | Fmoc-D-Arg (Tos) | Fmoc-D-p-I-Phe | 3,4-Dimethoxyphenylacetic acid | 583 | 12.6 |
| 60 | Fmoc-D-Arg (Tos) | Fmoc-D-p-I-Phe | 3,5-Difluorophenylacetic | 559 | 9.7 |

6602

| ### # | R1 Amino Acid | R2 Amino Acid | R3 Carboxylic acid | MW | Amt mg |
|---|---|---|---|---|---|
| 1 | Boc-L-Arg (Tos) | Boc-L-Phenylglycine | 4-FPhCH$_2$CO$_2$H | 400 | 22 |
| 2 | Boc-L-Arg (Tos) | Boc-L-Phenylalanine | 4-FPhCH$_2$CO$_2$H | 414 | 26 |
| 3 | Boc-L-Arg (Tos) | Boc-L-Homophenylalanine | 4-FPhCH$_2$CO$_2$H | 428 | 16 |
| 4 | Boc-L-Arg (Tos) | Boc-L-p-Fluorophenylalanine | 4-FPhCH$_2$CO$_2$H | 432 | 28 |
| 5 | Boc-L-Arg (Tos) | Boc-L-p-Chlorophenylalanine | 4-FPhCH$_2$CO$_2$H | 448 | 28 |
| 6 | Boc-L-Arg (Tos) | Boc-L-p-Cyanophenylalanine | 4-FPhCH$_2$CO$_2$H | 439 | 21 |
| 7 | Boc-L-Arg (Tos) | Boc-L-p-Biphenylalanine | 4-FPhCH$_2$CO$_2$H | 490 | 38 |
| 8 | Boc-L-Arg (Tos) | Boc-L-3,4-Dichlorophenylalanine | 4-FPhCH$_2$CO$_2$H | 483 | 31 |
| 9 | Boc-L-Arg (Tos) | Boc-L-3-Pyridylalanine | 4-FPhCH$_2$CO$_2$H | 415 | 27 |
| 10 | Boc-L-Arg (Tos) | Boc-L-4-Pyridylalanine | 4-FPhCH$_2$CO$_2$H | 415 | 41 |
| 11 | Boc-L-Arg (Tos) | Boc-L-Cyclohexylalanine | 4-FPhCH$_2$CO$_2$H | 420 | 26 |
| 12 | Boc-L-Arg (Tos) | Boc-L-Valine | 4-FPhCH$_2$CO$_2$H | 366 | 27 |
| 13 | Boc-L-Arg (Tos) | Boc-L-Tyrosine | 4-FPhCH$_2$CO$_2$H | 430 | 37 |
| 14 | Boc-L-Arg (Tos) | Boc-L-Tyrptophan | 4-FPhCH$_2$CO$_2$H | 453 | 41 |
| 15 | Boc-L-Arg (Tos) | Boc-L-Histidine (Trt) | 4-FPhCH$_2$CO$_2$H | 403 | 28 |

-continued

6602

| ### # | R1 Amino Acid | R2 Amino Acid | R3 Carboxylic acid | MW | Amt mg |
|---|---|---|---|---|---|
| 16 | Boc-L-Arg (Tos) | Boc-L-Lysine (Z) | 4-FPhCH$_2$CO$_2$H | 394 | 22 |
| 17 | Boc-L-Arg (Tos) | Boc-L-Aminobutyric acid | 4-FPhCH$_2$CO$_2$H | 352 | 13 |
| 18 | Boc-L-Arg (Tos) | Boc-L-3-(2naphthyl)alanine | 4-FPhCH$_2$CO$_2$H | 464 | 24 |
| 19 | Boc-L-Arg (Tos) | Boc-L-Aspartic acid | 4-FPhCH$_2$CO$_2$H | 382 | 15 |
| 20 | Boc-L-Arg (Tos) | Boc-L-Ornithine (Fmoc) | 4-FPhCH$_2$CO$_2$H | 380 | 22 |
| 22 | Boc-L-Arg (Tos) | Boc-D-Phenylalanine | 4-FPhCH$_2$CO$_2$H | 414 | 26 |
| 23 | Boc-L-Arg (Tos) | Boc-D-Homophenylalanine | 4-FPhCH$_2$CO$_2$H | 428 | 28 |
| 24 | Boc-L-Arg (Tos) | Boc-D-p-Fluorophenylalanine | 4-FPhCH$_2$CO$_2$H | 432 | 23 |
| 25 | Boc-L-Arg (Tos) | Boc-D-p-Chlorophenylalanine | 4-FPhCH$_2$CO$_2$H | 448 | 30 |
| 26 | Boc-L-Arg (Tos) | Boc-D-p-Bromophenylalanine | 4-FPhCH$_2$CO$_2$H | 493 | 31 |
| 27 | Boc-L-Arg (Tos) | Boc-D-p-Iodophenylalanine | 4-FPhCH$_2$CO$_2$H | 540 | 26 |
| 28 | Boc-L-Arg (Tos) | Fmoc-D-p-Nitrophenylalaine | 4-FPhCH$_2$CO$_2$H | 459 | 38 |
| 29 | Boc-L-Arg (Tos) | Fmoc-D-p-Biphenylalanine | 4-FPhCH$_2$CO$_2$H | 490 | 31 |
| 30 | Boc-L-Arg (Tos) | Fmoc-D-3,4-Difluorophenylalanine | 4-FPhCH$_2$CO$_2$H | 450 | 21 |
| 31 | Boc-L-Arg (Tos) | Fmoc-D-3-(2naphthyl)alanine | 4-FPhCH$_2$CO$_2$H | 464 | 39 |
| 32 | Boc-L-Arg (Tos) | Boc-D-2-Naphthylalanine | 4-FPhCH$_2$CO$_2$H | 464 | 28 |
| 33 | Boc-L-Arg (Tos) | Boc-D-Valine | 4-FPhCH$_2$CO$_2$H | 366 | 22 |
| 34 | Boc-L-Arg (Tos) | Fmoc-L-Leucine | 4-FPhCH$_2$CO$_2$H | 380 | 29 |
| 35 | Boc-L-Arg (Tos) | Boc-D-Tyrsine (OEt) | 4-FPhCH$_2$CO$_2$H | 458 | 35 |
| 36 | Boc-L-Arg (Tos) | Fmoc-D-Histidine (Trt) | 4-FPhCH$_2$CO$_2$H | 403 | 57 |
| 37 | Boc-D-Arg (Tos) | Boc-L-Phenylglycine | 4-FPhCH$_2$CO$_2$H | 400 | 28 |
| 38 | Boc-D-Arg (Tos) | Boc-L-Phenylalanine | 4-FPhCH$_2$CO$_2$H | 414 | 25 |
| 39 | Boc-D-Arg (Tos) | Boc-L-Homophenylalanine | 4-FPhCH$_2$CO$_2$H | 428 | 24 |
| 40 | Boc-D-Arg (Tos) | Boc-L-p-Fluorophenylalanine | 4-FPhCH$_2$CO$_2$H | 432 | 27 |
| 41 | Boc-D-Arg (Tos) | Boc-L-p-Chlorophenylalanine | 4-FPhCH$_2$CO$_2$H | 448 | 34 |
| 42 | Boc-D-Arg (Tos) | Boc-L-p-Iodophenylalanine | 4-FPhCH$_2$CO$_2$H | 540 | 31 |
| 43 | Boc-D-Arg (Tos) | Boc-L-p-Cyanophenylalanine | 4-FPhCH$_2$CO$_2$H | 439 | 33 |
| 44 | Boc-D-Arg (Tos) | Boc-L-p-Biphenylalanine | 4-FPhCH$_2$CO$_2$H | 490 | 17 |
| 45 | Boc-D-Arg (Tos) | Boc-L-3,4-Dichlorophenylalanine | 4-FPhCH$_2$CO$_2$H | 483 | 17 |
| 46 | Boc-D-Arg (Tos) | Boc-L-3-Pyridylalanine | 4-FPhCH$_2$CO$_2$H | 415 | 25 |
| 47 | Boc-D-Arg (Tos) | Boc-L-4-Pyridylalanine | 4-FPhCH$_2$CO$_2$H | 415 | 31 |
| 48 | Boc-D-Arg (Tos) | Boc-L-Cyclohexylalanine | 4-FPhCH$_2$CO$_2$H | 420 | 14 |
| 49 | Boc-D-Arg (Tos) | Boc-L-2-Naphthylalanine | 4-FPhCH$_2$CO$_2$H | 464 | 26 |
| 50 | Boc-D-Arg (Tos) | Boc-L-3-(2naphthyl)alanine | 4-FPhCH$_2$CO$_2$H | 464 | 29 |
| 51 | Boc-D-Arg (Tos) | Boc-L-Valine | 4-FPhCH$_2$CO$_2$H | 366 | 22 |
| 52 | Boc-D-Arg (Tos) | Fmoc-L-Leucine | 4-FPhCH$_2$CO$_2$H | 380 | 32 |
| 53 | Boc-D-Arg | Boc-L-Tryptophan | 4-FPhCH$_2$CO$_2$H | 453 | 27 |

-continued

6602

| ### # | R1 Amino Acid | R2 Amino Acid | R3 Carboxylic acid | MW | Amt mg |
|---|---|---|---|---|---|
| 54 | Boc-D-Arg (Tos) | Boc-L-Tyrosine | 4-FPhCH$_2$CO$_2$H | 430 | 36 |
| 55 | Boc-D-Arg (Tos) | Boc-L-Histidine (Trt) | 4-FPhCH$_2$CO$_2$H | 403 | 15 |
| 56 | Boc-D-Arg (Tos) | Boc-L-Aspartic acid | 4-FPhCH$_2$CO$_2$H | 382 | 26 |
| 57 | Boc-D-Arg (Tos) | Boc-L-Lysine (Z) | 4-FPhCH$_2$CO$_2$H | 394 | 33 |
| 58 | Boc-D-Arg (Tos) | Boc-L-Ornithine (Fmoc) | 4-FPhCH$_2$CO$_2$H | 380 | 24 |
| 59 | Boc-D-Arg (Tos) | Boc-L-Aminobutyric acid | 4-FPhCH$_2$CO$_2$H | 352 | 15 |
| 60 | Boc-D-Arg (Tos) | Boc-D-Phenylglycine | 4-FPhCH$_2$CO$_2$H | 400 | 24 |
| 61 | Boc-D-Arg (Tos) | Boc-D-Phenylalanine | 4-FPhCH$_2$CO$_2$H | 414 | 14 |
| 62 | Boc-D-Arg (Tos) | Boc-D-Homophenylalanine | 4-FPhCH$_2$CO$_2$H | 428 | 22 |
| 63 | Boc-D-Arg (Tos) | Boc-D-p Fluorophenylalanine | 4-FPhCH$_2$CO$_2$H | 432 | 30 |
| 64 | Boc-D-Arg (Tos) | Boc-D-p-Chlorophenylalanine | 4-FPhCH$_2$CO$_2$H | 448 | 38 |
| 65 | Boc-D-Arg (Tos) | Boc-D-p-Bromophenylalanine | 4-FPhCH$_2$CO$_2$H | 493 | 28 |
| 66 | Boc-D-Arg (Tos) | Boc-D-p-Cyanophenylalanine | 4-FPhCH$_2$CO$_2$H | 439 | 25 |
| 67 | Boc-D-Arg (Tos) | Fmoc-D-p-Biphenylalanine | 4-FPhCH$_2$CO$_2$H | 490 | 29 |
| 68 | Boc-D-Arg (Tos) | Fmoc-D-3,4-Difluorophenylalanine | 4-FPhCH$_2$CO$_2$H | 450 | 28 |
| 69 | Boc-D-Arg (Tos) | Fmoc-D-Cyclohexylalanine | 4-FPhCH$_2$CO$_2$H | 420 | 28 |
| 70 | Boc-D-Arg (Tos) | Fmoc-D-3-(2naphthyl)alanine | 4-FPhCH$_2$CO$_2$H | 464 | 26 |
| 71 | Boc-D-Arg (Tos) | Boc-D-2-Naphthylalanine | 4-FPhCH$_2$CO$_2$H | 464 | 35 |
| 72 | Boc-D-Arg (Tos) | Boc-D-Valine | 4-FPhCH$_2$CO$_2$H | 366 | 32 |
| 73 | Boc-D-Arg (Tos) | Fmoc-D-Histidine (Trt) | 4-FPhCH$_2$CO$_2$H | 403 | 33 |

6603

| 6603 # | R1 Amino Acid | R2 Amino Acid | R3 Carboxylic acid | MW | Amt (mg) |
|---|---|---|---|---|---|
| 1 | N-a-Boc-N-g-Fmoc-L-Diaminobutyric acid | Fmoc-L-Tyr (OEt) | 4-ClPhCh$_2$CO$_2$H | 419 | 54 |
| 2 | N-a-Boc-N-g-Fmoc-L-Diaminobutyric acid | Fmoc-L-Tyr (OEt) | 4-ClPhCh$_2$CO$_2$H | 433 | 47 |
| 3 | Fmoc-L-Arg (Me) 2-OH | Fmoc-L-Tyr (OEt) | 4-ClPhCh$_2$CO$_2$H | 447 | 42 |
| 4 | Fmoc-L-HomoArg (Pmc)-OH | Fmoc-L-Tyr (OEt) | 4-ClPhCh$_2$CO$_2$H | 447 | 38 |
| 5 | Boc-L-Ser-OH | Fmoc-L-Tyr (OEt) | 4-ClPhCh$_2$CO$_2$H | 406 | 35 |
| 6 | Boc-L-40 Nitrophenylalanine | Fmoc-L-Tyr (OEt) | 4-ClPhCh$_2$CO$_2$H | 511 | 36 |
| 7 | Boc-L-3-Cyanophenylalanine | Fmoc-L-Tyr (OEt) | 4-ClPhCh$_2$CO$_2$H | 495 | 44 |
| 8 | Boc-L-4-Cyanophenylalanine | Fmoc-L-Tyr (OEt) | 4-ClPhCh$_2$CO$_2$H | 495 | 45 |
| 9 | Boc-L-3-Pyridylalanine | Fmoc-L-Tyr (OEt) | 4-ClPhCh$_2$CO$_2$H | 467 | 51 |
| 10 | Boc-L-4-Pyridylalanine | Fmoc-L-Tyr (OEt) | 4-ClPhCh$_2$CO$_2$H | 467 | 58 |

-continued

6603

| 6603 # | R1 Amino Acid | R2 Amino Acid | R3 Carboxylic acid | MW | Amt (mg) |
|---|---|---|---|---|---|
| 11 | N-a-Boc-N-g-Fmoc-L-Diaminobutyric acid | Fmoc-L-Tyr (OEt) | 4-ClPhCh$_2$CO$_2$H | 501 | 57 |
| 12 | N-a-Boc-N-g-Fmoc-L-Diaminobutyric acid | Fmoc-L-Tyr (OEt) | 4-ClPhCh$_2$CO$_2$H | 515 | 55 |
| 13 | Fmoc-L-Arg (Me) 2-OH | Fmoc-L-Tyr (OEt) | 4-ClPhCh$_2$CO$_2$H | 529 | 56 |
| 14 | Fmoc-L-HomoArg (Pmc)-OH | Fmoc-L-Tyr (OEt) | 4-ClPhCh$_2$CO$_2$H | 529 | 60 |
| 15 | Boc-L-Ser-OH | Fmoc-L-Tyr (OEt) | 4-ClPhCh$_2$CO$_2$H | 488 | 43 |
| 16 | Fmoc-L-His (Trt)-OH | Fmoc-L-Tyr (OEt) | 4-ClPhCh$_2$CO$_2$H | 538 | 65 |
| 17 | Boc-L-3-Cyanophenylalanine | Fmoc-L-Tyr (OEt) | 4-ClPhCh$_2$CO$_2$H | 577 | 56 |
| 18 | Boc-L-4-Cyanophenylalanine | Fmoc-L-Tyr (OEt) | 4-ClPhCh$_2$CO$_2$H | 577 | 57 |
| 19 | Boc-L-3-Pyridylalanine | Fmoc-L-Tyr (OEt) | 4-ClPhCh$_2$CO$_2$H | 549 | 54 |
| 20 | Boc-L-4-Pyridylalanine | Fmoc-L-Tyr (OEt) | 4-ClPhCh$_2$CO$_2$H | 549 | 69 |

6612

| Cmpd | R1 | R2 | R3 | R4 | MW | Yield |
|---|---|---|---|---|---|---|
| 1 | Boc-L-Tic (OH)—OH | Boc-L-Tye (Oet) | 4-Cl-phenylacetic acid | | 493 | 69.2 |
| 2 | Boc-L-Thienylalanine | Boc-L-Tyr (Oet) | 4-Cl-phenylacetic acid | | 471 | 35.2 |
| 3 | Boc-L-Norleucine | Boc-L-Tyr (Oet) | 4-Cl-phenylacetic acid | | 431 | 38.5 |
| 6 | Boc-Dab (Fmoc) | Boc-L-Tyr (OEt)—OH | 4-Cl-Phenylacetic acid | Acetic anhydride | 446 | 60.1 |
| 7 | Boc-Dab (Fmoc) | Boc-L-Tyr (OEt)—OH | 4-Cl-Phenylacetic acid | Formaldehyde | 446 | 58.2 |
| 8 | Boc-Orn (Fmoc) | Boc-L-Tyr (OEt)—OH | 4-Cl-Phenylacetic acid | Formaldehyde | 460 | 65.7 |
| 9 | Boc-Lys (Fmoc) | Boc-L-Tyr (OEt)—OH | 4-Cl-Phenylacetic acid | Formaldehyde | 474 | 51.5 |
| 10 | Boc-Lys (Fmoc) | Boc-L-Tyr (OEt)—OH | 4-Cl-Phenylacetic acid | Formaldehyde | 516 | 13.1 |
| 11 | Fmoc-Dap (Boc) | Boc-L-Tyr (OEt)—OH | 4-Cl-Phenylacetic acid | H | 404 | 63.2 |
| 12 | Fmoc-Dap (Boc) | Boc-L-Tyr (OEt)—OH | 4-Cl-Phenylacetic acid | Fmoc | 418 | 38.6 |
| 13 | Fmoc-Orn (Boc) | Boc-L-Tyr (OEt)—OH | 4-Cl-Phenylacetic acid | Fmoc | 446 | 57.4 |
| 15 | Boc-Thr (Bzl) | Boc-L-Tyr (OEt)—OH | 4-Cl-Phenylacetic acid | | 419 | 55.5 |
| 16 | Boc-Asp (Bzl) | Boc-L-Tyr (OEt)—OH | 4-Cl-Phenylacetic acid | | 419 | 54.7 |
| 17 | Boc-Glu (Bzl) | Boc-L-Tyr (OEt)—OH | 4-Cl-Phenylacetic acid | | 433 | 46.7 |

-continued

6612

| Cmpd | R1 | R2 | R3 | R4 | MW | Yield |
|---|---|---|---|---|---|---|
| 18 | Boc-Hyp (Bzl) | Boc-L-Tyr (OEt)—OH | 4-Cl-Phenylacetic acid | | 431 | 62.7 |
| 19 | Boc-Val | Boc-L-Tyr (OEt)—OH | 4-Cl-Phenylacetic acid | | 417 | 32.6 |
| 20 | Boc-tBuGly | Boc-L-Tyr (OEt)—OH | 4-Cl-Phenylacetic acid | | 431 | 36.3 |
| 21 | Boc-Ser (Me) | Boc-L-Tyr (OEt)—OH | 4-Cl-Phenylacetic acid | | 419 | 48.6 |
| 22 | Boc-2-Pyrala | Boc-L-Tyr (OEt)—OH | 4-Cl-Phenylacetic acid | | 466 | 58.4 |
| 23 | Boc-Met (O) 2 | Boc-L-Tyr (OEt)—OH | 4-Cl-Phenylacetic acid | | 481 | 62.4 |
| 24 | Boc-Cys (MeOBzl) | Boc-L-Tyr (OEt)—OH | 4-Cl-Phenylacetic acid | | 421 | 54 |
| 25 | Boc-Met (O) | Boc-L-Tyr (OEt)—OH | 4-Cl-Phenylacetic acid | | 449 | 55 |
| 26 | Boc—Pen (MeOBzl) | Boc-L-Tyr (OEt)—OH | 4-Cl-Phenylacetic acid | | 449 | 56.9 |
| 27 | Boc-aAbu | Boc-L-Tyr (OEt)—OH | 4-Cl-Phenylacetic acid | | 403 | 36.4 |
| 28 | Boc-Lys (TFA) | Boc-L-Tyr (OEt)—OH | 4-Cl-Phenylacetic acid | | 528 | 60.6 |
| 29 | Boc-Phe | Boc-L-Tyr (OEt)—OH | 4-Cl-Phenylacetic acid | | 465 | 50.1 |
| 30 | Boc-Thiopro | Boc-L-Tyr (OEt)—OH | 4-Cl-Phenylacetic acid | | 433 | 42.3 |
| 31 | Fmoc-Dab (Boc) | Boc-L-Tyr (OEt)—OH | 4-Cl-Phenylacetic acid | H | 418 | 48.2 |
| 32 | Fmoc-Dab (Boc) | Boc-L-Tyr (OEt)—OH | 4-Cl-Phenylacetic acid | Fmoc | 432 | 43.3 |
| 33 | Fmoc-Orn (Boc) | Boc-L-Tyr (OEt)—OH | 4-Cl-Phenylacetic acid | H | 432 | 31.0 |
| 34 | Fmoc-Lys (Boc) | Boc-L-Tyr (OEt)—OH | 4-Cl-Phenylacetic acid | H | 446 | 20.2 |
| 35 | Boc-Dap (Fmoc) | Boc-L-Tyr (OEt)—OH | 4-Cl-Phenylacetic acid | H | 404 | 50.6 |
| 36 | Boc-Dap (Fmoc) | Boc-L-Tyr (OEt)—OH | 4-Cl-Phenylacetic acid | Fmoc | 418 | 45.3 |
| 37 | Boc-Dap (Fmoc) | Boc-L-Tyr (OEt)—OH | 4-Cl-Phenylacetic acid | Formaldehyde | 432 | 20.8 |
| 38 | Boc-Dap (Fmoc) | Boc-L-Tyr (OEt)—OH | 4-Cl-Phenylacetic acid | Acetic anhydride | 432 | 45.0 |

6614

| Cmpd | R1: Diamino acid | R2: Amino acid | R3: Carboxylic acid | R4: Carboxylic acid | MW | Mg |
|---|---|---|---|---|---|---|
| 1 | N-a-Boc-N-b-Fmoc-Dap | Boc-L-Tyr (OEt) | p-Cl-phenylacetic acid | Me | 419 | 67 |
| 2 | N-a-Boc-N-b-Fmoc-Dap | Boc-L-Tyr (OEt) | p-Cl-phenylacetic acid | H | 405 | 67 |
| 3 | N-a-Boc-N-b-Fmoc-Dap | Boc-L-Tyr (OEt) | p-Cl-phenylacetic acid | Acetic acid | 433 | 66 |
| 4 | N-a-Boc-N-b-Fmoc-Dap | Boc-L-Tyr (OEt) | p-Cl-phenylacetic acid | Butanoic acid | 461 | 64 |
| 5 | N-a-Boc-N-b-Fmoc-Dap | Boc-L-Tyr (OEt) | p-Cl-phenylacetic acid | Pivalic acid | 475 | 47 |
| 6 | N-a-Boc-N-b-Fmoc-Dap | Boc-L-Tyr (OEt) | p-Cl-phenylacetic acid | Benzoic acid | 495 | 73 |
| 7 | N-a-Boc-N-b-Fmoc-Dap | Boc-L-Tyr (OEt) | p-Cl-phenylacetic acid | Phenylacetic acid | 509 | 51 |
| 8 | N-a-Boc-N-b-Fmoc-Dap | Boc-L-Tyr (OEt) | p-Cl-phenylacetic acid | Hydrocinnamic acid | 523 | 51 |
| 9 | N-a-Boc-N-b-Fmoc-Dap | Boc-L-Tyr (OEt) | p-Cl-phenylacetic acid | Cyclohexane carboxylic acid | 501 | 69 |
| 10 | N-a-Boc-N-b-Fmoc-Dap | Boc-L-Tyr (OEt) | p-Cl-phenylacetic acid | Cyclohexyl acetic acid | 515 | 65 |
| 11 | N-a-Boc-N-b-Fmoc-Dap | Boc-L-Tyr (OEt) | p-Cl-phenylacetic acid | Isonicotinic acid | 496 | 84 |
| 12 | N-a-Boc-N-b-Fmoc-Dap | Boc-L-Tyr (OEt) | p-Cl-phenylacetic acid | Monomethylsuccinate | 477 | 68 |
| 13 | N-a-Boc-N-b-Fmoc-Dap | Boc-L-Tyr (OEt) | p-Cl-phenylacetic acid | Monomethylglutarate | 491 | 91 |
| 3 | L-Boc-Ornithine (Fmoc)—OH | Boc-L-Tyr (OEt) | p-Cl-phenylacetic acid | Me | 447 | 62 |
| 15 | L-Boc-Ornithine (Fmoc)—OH | Boc-L-Tyr (OEt) | p-Cl-phenylacetic acid | H | 433 | 59 |
| 16 | L-Boc-Ornithine (Fmoc)—OH | Boc-L-Tyr (OEt) | p-Cl-phenylacetic acid | Acetic acid | 461 | 47 |
| 17 | L-Boc-Ornithine (Fmoc)—OH | Boc-L-Tyr (OEt) | p-Cl-phenylacetic acid | Butanoic acid | 489 | 63 |
| 18 | L-Boc-Ornithine (Fmoc)—OH | Boc-L-Tyr (OEt) | p-Cl-phenylacetic acid | Pivalic acid | 503 | 76 |
| 19 | L-Boc-Ornithine (Fmoc)—OH | Boc-L-Tyr (OEt) | p-Cl-phenylacetic acid | Benzoic acid | 523 | 74 |
| 20 | L-Boc-Ornithine (Fmoc)—OH | Boc-L-Tyr (OEt) | p-Cl-phenylacetic acid | Phenylacetic acid | 537 | 43 |
| 21 | L-Boc-Ornithine (Fmoc)—OH | Boc-L-Tyr (OEt) | p-Cl-phenylacetic acid | Hydrocinnamic acid | 551 | 73 |
| 22 | L-Boc-Ornithine (Fmoc)—OH | Boc-L-Tyr (OEt) | p-Cl-phenylacetic acid | Cyclohexane carboxylic acid | 529 | 63 |
| 23 | L-Boc-Ornithine (Fmoc)—OH | Boc-L-Tyr (OEt) | p-Cl-phenylacetic acid | Cyclohexyl acetic acid | 543 | 84 |
| 24 | L-Boc-Ornithine (Fmoc)—OH | Boc-L-Tyr (OEt) | p-Cl-phenylacetic acid | Isonicotinic acid | 524 | 73 |

-continued

6614

| Cmpd | R1: Diamino acid | R2: Amino acid | R3: Carboxylic acid | R4: Carboxylic acid | MW | Mg |
|---|---|---|---|---|---|---|
| 25 | L-Boc-Ornithine (Fmoc)—OH | Boc-L-Tyr (OEt) | p-Cl-phenylacetic acid | Methoxyacetic acid | 491 | 58 |
| 26 | L-Boc-Ornithine (Fmoc)—OH | Boc-L-Tyr (OEt) | p-Cl-phenylacetic acid | 3-Methoxypropionic acid | 505 | 67 |
| 27 | L-Boc-Ornithine (Fmoc)—OH | Boc-L-Tyr (OEt) | p-Cl-phenylacetic acid | Monomethylsuccinate | 505 | 71 |
| 28 | L-Boc-Ornithine (Fmoc)—OH | Boc-L-Tyr (OEt) | p-Cl-phenylacetic acid | Monomethylglutarate | 519 | 64 |
| 29 | L-Boc-Ornithine (Fmoc)—OH | Boc-L-Tyr (OEt) | p-Cl-phenylacetic acid | Phenoxyacetic acid | 553 | 71 |
| 30 | L-Boc-Lysine (Fmoc)—OH | Boc-L-Tyr (OEt) | p-Cl-phenylacetic acid | Me | 461 | 70 |
| 4 | L-Boc-Lysine (Fmoc)—OH | Boc-L-Tyr (OEt) | p-Cl-phenylacetic acid | H | 447 | 55 |
| 32 | L-Boc-Lysine (Fmoc)—OH | Boc-L-Tyr (OEt) | p-Cl-phenylacetic acid | Acetic acid | 475 | 49 |
| 33 | L-Boc-Lysine (Fmoc)—OH | Boc-L-Tyr (OEt) | p-Cl-phenylacetic acid | Butanoic acid | 503 | 60 |
| 34 | L-Boc-Lysine (Fmoc)—OH | Boc-L-Tyr (OEt) | p-Cl-phenylacetic acid | Pivalic acid | 517 | 69 |
| 35 | L-Boc-Lysine (Fmoc)—OH | Boc-L-Tyr (OEt) | p-Cl-phenylacetic acid | Benzoic acid | 537 | 77 |
| 36 | L-Boc-Lysine (Fmoc)—OH | Boc-L-Tyr (OEt) | p-Cl-phenylacetic acid | Phenylacetic acid | 551 | 69 |
| 37 | L-Boc-Lysine (Fmoc)—OH | Boc-L-Tyr (OEt) | p-Cl-phenylacetic acid | Hydrocinnamic acid | 565 | 53 |
| 38 | L-Boc-Lysine (Fmoc)—OH | Boc-L-Tyr (OEt) | p-Cl-phenylacetic acid | Cyclohexane carboxylic acid | 543 | 73 |
| 39 | L-Boc-Lysine (Fmoc)—OH | Boc-L-Tyr (OEt) | p-Cl-phenylacetic acid | Cyclohexyl acetic acid | 557 | 76 |
| 40 | L-Boc-Lysine (Fmoc)—OH | Boc-L-Tyr (OEt) | p-Cl-phenylacetic acid | Isonicotinic acid | 538 | 53 |
| 41 | L-Boc-Lysine (Fmoc)—OH | Boc-L-Tyr (OEt) | p-Cl-phenylacetic acid | Methoxyacetic acid | 505 | 57 |
| 42 | L-Boc-Lysine (Fmoc)—OH | Boc-L-Tyr (OEt) | p-Cl-phenylacetic acid | 3-Methoxypropionic acid | 519 | 48 |
| 43 | L-Boc-Lysine (Fmoc)—OH | Boc-L-Tyr (OEt) | p-Cl-phenylacetic acid | Monomethylsuccinate | 519 | 60 |
| 44 | L-Boc-Lysine (Fmoc)—OH | Boc-L-Tyr (OEt) | p-Cl-phenylacetic acid | Monomethylglutarate | 533 | 63 |
| 45 | L-Boc-Lysine (Fmoc)—OH | Boc-L-Tyr (OEt) | p-Cl-phenylacetic acid | Phenoxyacetic acid | 567 | 57 |
| 46 | L-Boc-Lysine (Fmoc)—OH | Boc-L-Tyr (OEt) | p-Cl-phenylacetic acid | 2-(2-methoxyethoxy) acetic acid | 549 | 55 |

6615 R-groups

| Cmpd | R1 | R2 | R3 | MW | Yield | ApPur |
|---|---|---|---|---|---|---|
| 1 | Boc-Ser(Bzl)-OH | Boc-Tyr(Et)—OH | 4-FC₆H₄CH₂CO₂H | 390 | 48 | 80 |
| 2 | Boc-Ser(Bzl)-OH | Boc-D-Tyr(Et)—OH | 4-FC₆H₄CH₂CO₂H | 390 | 49 | 90 |
| 3 | Boc-D-Ser(Bzl)-OH | Boc-Tyr(Et)—OH | 4-FC₆H₄CH₂CO₂H | 390 | 46 | 90 |
| 4 | Boc-D-Ser(Bzl)-OH | Boc-D-Tyr(Et)—OH | 4-FC₆H₄CH₂CO₂H | 390 | 48 | 85 |
| 5 | Boc-3-PyAla | Boc-Tyr(Et)—OH | 4-FC₆H₄CH₂CO₂H | 451 | 64 | 95 |
| 6 | Boc-3-PyAla | Boc-D-Tyr(Et)—OH | 4-FC₆H₄CH₂CO₂H | 451 | 67 | 95 |
| 7 | Boc-D-3-PyAla | Boc-Tyr(Et)—OH | 4-FC₆H₄CH₂CO₂H | 451 | 64 | 95 |
| 8 | Boc-D-3-RyAla | Boc-D-Tyr(Et)—OH | 4-FC₆H₄CH₂CO₂H | 451 | 59 | 95 |
| 9 | Boc-Orn(Fmoc)-OH | Boc-Tyr(Et)—OH | 4-FC₆H₄CH₂CO₂H | 431 | 52 | 70 |
| 10 | Boc-Orn(Fmoc)-OH | Boc-D-Tyr(Et)—OH | 4-FC₆H₄CH₂CO₂H | 431 | 50 | 75 |
| 11 | Boc-D-Orn(Fmoc)-OH | Boc-Tyr(Et)—OH | 4-FC₆H₄CH₂CO₂H | 431 | 69 | 80 |
| 12 | Boc-D-Orn(Fmoc)-OH | Boc-D-Tyr(Et)—OH | 4-FC₆H₄CH₂CO₂H | 431 | 46 | 75 |

6617 Tyrosine ethers by Mitsunobu

| Cmpd | R1 | R2 | R3 | R4 | MW | Yield |
|---|---|---|---|---|---|---|
| 1 | Boc-L-Arg (Tos) | Boc-L-Tyr | 4-FPhCH₂CO₂H | ethanol | 459 | 4.4 |
| 2 | Boc-L-Arg (Tos) | Boc-L-Tyr | 4-FPhCH₂CO₂H | propanol | 473 | 21.2 |
| 3 | Boc-L-Arg (Tos) | Boc-L-Tyr | 4-FPhCH₂CO₂H | 1-piperidine ethanol | 542 | 81.1 |
| 4 | Boc-L-Arg (Tos) | Boc-L-Tyr | 4-FPhCH₂CO₂H | 3,3-dimethyl-1-butanol | 515 | 13.8 |
| 5 | Boc-L-Arg (Tos) | Boc-L-Tyr | 4-FPhCH₂CO₂H | isoamyl alcohol | 501 | 23.4 |
| 6 | Boc-L-Arg (Tos) | Boc-L-Tyr | 4-FPhCH₂CO₂H | N,N-dimethylethanol amine | 502 | 20.8 |

Tyrosine ethers from acylated tyrosine dipeptide on resin via Fukuyama Mitsunobu alkylation of the tyrosine phenol with the R4 alcohol's

6620 TRG6620

| Cmpd | R1 | R2 | R3 | MW | mg |
|---|---|---|---|---|---|
| 1 | BOC-L-Orn (FMOC)* | BOC-L-Tyr (OEt) | cyclohexylacetic acid | 418 | 56 |
| 5 | BOC-L-Orn (FMOC)* | BOC-L-Tyr (OEt) | 4-(Trifluoromethyl) phenylacetic acid | 481 | 63 |
| 6 | BOC-L-Orn (FMOC)* | BOC-L-Tyr (OEt) | 4-Ethoxyphenylacetic acid | 457 | 60 |
| 7 | BOC-L-Orn (FMOC)* | Boc-L-Homophenyl alanine | cyclohexylacetic acid | 389 | 54 |
| 11 | BOC-L-Orn (FMOC)* | Boc-L-Homophenyl alanine | 4-(Trifluoromethyl) phenylacetic acid | 450 | 60 |
| 12 | BOC-L-Orn (FMOC)* | Boc-L-Homophenyl alanine | 4-Ethoxyphenylacetic | 426 | 58 |
| 13 | BOC-L-Orn (FMOC)* | Boc-L-Tryptophan | cyclohexylacetic acid | 413 | 54 |
| 17 | BOC-L-Orn (FMOC)* | Boc-L-Tryptophan | 4-(Trifluoromethyl) phenylacetic acid | 475 | 60 |
| 18 | BOC-L-Orn (FMOC)* | Boc-L-Tryptophan | 4-Ethoxyphenylacetic | 451 | 56 |
| 19 | BOC-L-Orn (FMOC)* | Boc-L-4 Chlorophenylalanine | cyclohexylacetic acid | 408 | 55 |
| 23 | BOC-L-Orn (FMOC)* | Boc-L-4 Chlorophenylalanine | 4-(Trifluoromethyl) phenylacetic acid | 470 | 63 |
| 24 | BOC-L-Orn (FMOC)* | Boc-L-4 Chlorophenylalanine | 4-Ethoxyphenylacetic acid | 446 | 59 |

-continued

6620
TRG6620

| Cmpd | R1 | R2 | R3 | MW | mg |
|---|---|---|---|---|---|
| 14 | BOC-L-Arg (Tos) | BOC-L-Tyr (OEt) | cyclohexylacetic acid | 447 | 55 |
| 8 | BOC-L-Arg (Tos) | BOC-L-Tyr (OEt) | 4-(Trifluoromethyl) phenylacetic acid | 509 | 63 |
| 30 | BOC-L-Arg (Tos) | BOC-L-Tyr (OEt) | 4-Ethoxyphenylacetic acid | 485 | 59 |
| 31 | BOC-L-Arg (Tos) | Boc-L-Homophenyl alanine | cyclohexylacetic acid | 416 | 58 |
| 35 | BOC-L-Arg (Tos) | Boc-L-Homophenyl alanine | 4-(Trifluoromethyl) phenylacetic acid | 478 | 59 |
| 36 | BOC-L-Arg (Tos) | Boc-L-Homophenyl alanine | 4-Ethoxyphenylacetic acid | 454 | 63 |
| 37 | BOC-L-Arg (Tos) | Boc-L-Tryptophan | cyclohexylacetic acid | 442 | 56 |
| 41 | BOC-L-Arg (Tos) | Boc-L-Tryptophan | 4-(Trifluoromethyl) phenylacetic acid | 504 | 66 |
| 42 | BOC-L-Arg (Tos) | Boc-L-Tryptophan | 4-Ethoxyphenylacetic acid | 480 | 12 |
| 43 | BOC-L-Arg (Tos) | Boc-L-4-Chlorophenylalanine | cyclohexylacetic acid | 437 | 60 |
| 47 | BOC-L-Arg (Tos) | Boc-L-4-Chlorophenylalanine | 4-(Trifluoromethyl) phenylacetic acid | 499 | 68 |
| 48 | BOC-L-Arg (Tos) | Boc-L-4-Chlorophenylalanine | 4-Ethoxyphenylacetic acid | 475 | 67 |
| 49 | BOC-L-Lysine (FMOC) | BOC-L-Tyr (OEt) | cyclohexylacetic acid | 419 | 54 |
| 53 | BOC-L-Lysine (FMOC) | BOC-L-Tyr (OEt) | 4-(Trifluoromethyl) phenylacetic acid | 481 | 59 |
| 54 | BOC-L-Lysine (FMOC) | BOC-L-Tyr (OEt) | 4-Ethoxyphenylacetic acid | 457 | 57 |
| 55 | BOC-L-Lysine (FMOC) | Boc-L-Homophenyl alanine | cyclohexylacetic acid | 389 | 48 |
| 59 | BOC-L-Lysine (FMOC) | Boc-L-Homophenyl alanine | 4-(Trifluoromethyl) phenylacetic acid | 451 | 51 |
| 60 | BOC-L-Lysine (FMOC) | Boc-L-Homophenyl alanine | 4-Ethoxyphenylacetic acid | 427 | 48 |
| 61 | BOC-L-Lysine (FMOC) | Boc-L-Tryptophan | cyclohexylacetic acid | 414 | 48 |
| 65 | BOC-L-Lysine (FMOC) | Boc-L-Tryptophan | 4-(Trifluoromethyl) phenylacetic acid | 476 | 53 |
| 66 | BOC-L-Lysine (FMOC) | Boc-L-Tryptophan | 4-Ethoxyphenylacetic acid | 452 | 52 |
| 67 | BOC-L-Lysine (FMOC) | Boc-L-4-Chlorophenylalanine | cyclohexylacetic acid | 409 | 56 |
| 71 | BOC-L-Lysine (FMOC) | Boc-L-4-Chlorophenylalanine | 4-(Trifluoromethyl) phenylacetic acid | 471 | 62 |
| 72 | BOC-L-Lysine (FMOC) | Boc-L-4-Chlorophenylalanine | 4-Ethoxyphenylacetic acid | 447 | 60 |
| 73 | BOC-L-3-Cyanophe | BOC-L-Tyr (OEt) | cyclohexylacetic acid | 467 | 72 |
| 77 | BOC-L-3-Cyanophe | BOC-L-Tyr (OEt) | 4-(Trifluoromethyl) phenylacetic acid | 529 | 56 |
| 78 | BOC-L-3-Cyanophe | BOC-L-Tyr (OEt) | 4-Ethoxyphenylacetic acid | 505 | 57 |
| 79 | BOC-L-3-Cyanophe | Boc-L-Homophenyl alanine | cyclohexylacetic acid | 437 | 61 |
| 83 | BOC-L-3-Cyanophe | Boc-L-Homophenyl alanine | 4-(Trifluoromethyl) phenylacetic acid | 499 | 68 |
| 84 | BOC-L-3-Cyanophe | Boc-L-Homophenyl alanine | 4-Ethoxyphenylacetic acid | 475 | 62 |
| 85 | BOC-L-3-Cyanophe | Boc-L-Tryptophan | cyclohexylacetic acid | 462 | 66 |

-continued

6620
TRG6620

| Cmpd | R1 | R2 | R3 | MW | mg |
|---|---|---|---|---|---|
| 89 | BOC-L-3-Cyanophe | Boc-L-Tryptophan | 4-(Trifluoromethyl)phenylacetic acid | 524 | 49 |
| 90 | BOC-L-3-Cyanophe | Boc-L-Tryptophan | 4-Ethoxyphenylacetic acid | 500 | 55 |
| 91 | BOC-L-3-Cyanophe | Boc-L-4-Chlorophenylalanine | cyclohexylacetic acid | 457 | 74 |
| 95 | BOC-L-3-Cyanophe | Boc-L-4-Chlorophenylalanine | 4-(Trifluoromethyl)phenylacetic acid | 519 | 75 |
| 96 | BOC-L-3-Cyanophe | Boc-L-4-Chlorophenylalanine | 4-Ethoxyphenylacetic acid | 495 | 67 |
| 97 | BOC-L-3-Pyridylalanine | BOC-L-Tyr (OEt) | cyclohexylacetic acid | 439 | 53 |
| 101 | BOC-L-3-Pyridylalanine | BOC-L-Tyr (OEt) | 4-(Trifluoromethyl)phenylacetic acid | 501 | 73 |
| 102 | BOC-L-3-Pyridylalanine | BOC-L-Tyr (OEt) | 4-Ethoxyphenylacetic acid | 477 | 48 |
| 103 | BOC-L-3-Pyridylalanine | Boc-L-Homophenyl alanine | cyclohexylacetic acid | 409 | 68 |
| 107 | BOC-L-3-Pyridylalanine | Boc-L-Homophenyl alanine | 4-(Trifluoromethyl)phenylacetic acid | 471 | 53 |
| 108 | BOC-L-3-Pyridylalanine | Boc-L-Homophenyl alanine | 4-Ethoxyphenylacetic acid | 447 | 56 |
| 109 | BOC-L-3-Pyridylalanine | Boc-L-Tryptophan | cyclohexylacetic acid | 434 | 45 |
| 113 | BOC-L-3-Pyridylalanine | Boc-L-Tryptophan | 4-(Trifluoromethyl)phenylacetic acid | 496 | 73 |
| 114 | BOC-L-3-Pyridylalanine | Boc-L-Tryptophan | 4-Ethoxyphenylacetic acid | 472 | 56 |
| 115 | BOC-L-3-Pyridylalanine | Boc-L-4-Chlorophenylalanine | cyclohexylacetic acid | 429 | 31 |
| 119 | BOC-L-3-Pyridylalanine | Boc-L-4-Chlorophenylalanine | 4-(Trifluoromethyl)phenylacetic acid | 491 | 65 |
| 120 | BOC-L-3-Pyridylalanine | Boc-L-4-Chlorophenylalanine | 4-Ethoxyphenylacetic acid | 467 | 58 |

*The FMOC group on Ornithine was reduced to N-methyl on all Ornithine containing compounds (6620–1 through 6620–24)

| Cmpd | R1 | R2 | R3 | MW | Yield | % Pur |
|---|---|---|---|---|---|---|
| 1 | Boc-L-Tic(OH) | Boc-L-Tyr(OEt) | 4-ClPhCH$_2$CO$_2$H | 478 | 31 | 90 |
| 2 | Boc-Pro-OH | Boc-L-Tyr(OEt) | 4-ClPhCH$_2$CO$_2$H | 416 | 35 | 90 |
| 3 | Boc-HoPro-OH | Boc-L-Tyr(OEt) | 4-ClPhCH$_2$CO$_2$H | 430 | 21 | 75 |
| 4 | Boc-N-Methyl-Tyr(Bzl)-OH | Boc-L-Tyr(OEt) | 4-ClPhCH$_2$CO$_2$H | 496 | 22 | 65 |
| 5 | Boc-L-Tic(OH) | Boc-4,4-Biphenylalanine | 4-ClPhCH$_2$CO$_2$H | 510 | 27 | 90 |
| 6 | Boc-L-Tic(OH)-OH | Boc-4,4-Biphenylalanine | 4-ClPhCH$_2$CO$_2$H | 526 | 46 | 95 |
| 7 | Boc-Pro-OH | Boc-4,4-Biphenylalanine | 4-ClPhCH$_2$CO$_2$H | 448 | 35 | 90 |
| 8 | Boc-HoPro-OH | Boc-4,4-Biphenylalanine | 4-ClPhCH$_2$CO$_2$H | 462 | 27 | 70 |
| 9 | Boc-Hyp(Bzl)-OH | Boc-4,4-Biphenylalanine | 4-ClPhCH$_2$CO$_2$H | 464 | 43 | 60 |
| 10 | Boc-Phe-OH | Boc-4,4-Biphenylalanine | 4-ClPhCH$_2$CO$_2$H | 498 | 28 | 85 |
| 11 | Boc-N-Methyl-Tyr(Bzl)-OH | Boc-4,4-Biphenylalanine | 4-ClPhCH$_2$CO$_2$H | 528 | 44 | 55 |
| 12 | Boc-L-Tic(OH) | Boc-Glycine | 4-ClPhCH$_2$CO$_2$H | 344 | 25 | 90 |
| 13 | Boc-L-Tic(OH)-OH | Boc-Glycine | 4-ClPhCH$_2$CO$_2$H | 360 | 41 | 90 |

-continued

| Cmpd | R1 | R2 | R3 | MW | Yield | % Pur |
|---|---|---|---|---|---|---|
| 14 | Boc-Pro-OH | Boc-Glycine | 4-ClPhCH$_2$CO$_2$H | 282 | 22 | 90 |
| 15 | Boc-HoPro-OH | Boc-Glycine | 4-ClPhCH$_2$CO$_2$H | 296 | 30 | 80 |
| 16 | Boc-Hyp(Bzl)-OH | Boc-Glycine | 4-ClPhCH$_2$CO$_2$H | 298 | 32 | 85 |
| 17 | Boc-Phe-OH | Boc-Glycine | 4-ClPhCH$_2$CO$_2$H | 332 | 31 | 90 |
| 18 | Boc-Tyr(Bzl)-OH | Boc-Glycine | 4-ClPhCH$_2$CO$_2$H | 348 | 40 | 55 |
| 19 | Boc-N-Methyl-Tyr(Bzl)-OH | Boc-Glycine | 4-ClPhCH$_2$CO$_2$H | 362 | 47 | 60 |
| 20 | Boc-L-Tic(OH) | Boc-2-Naphthylalanine | 4-ClPhCH$_2$CO$_2$H | 484 | 46 | 90 |
| 21 | Boc-L-Tic(OH)-OH | Boc-2-Naphthylalanine | 4-ClPhCH$_2$CO$_2$H | 500 | 61 | 90 |
| 22 | Boc-Pro-OH | Boc-2-Naphthylalanine | 4-ClPhCH$_2$CO$_2$H | 422 | 30 | 85 |
| 23 | Boc-HoPro-OH | Boc-2-Naphthylalanine | 4-ClPhCH$_2$CO$_2$H | 436 | 35 | 80 |
| 24 | Boc-Hyp(Bzl)-OH | Boc-2-Naphthylalanine | 4-ClPhCH$_2$CO$_2$H | 438 | 45 | 70 |
| 25 | Boc-Phe-OH | Boc-2-Naphthylalanine | 4-ClPhCH$_2$CO$_2$H | 472 | 57 | 85 |
| 26 | Boc-Tyr(Bzl)-OH | Boc-2-Naphthylalanine | 4-ClPhCH$_2$CO$_2$H | 488 | 68 | 55 |
| 27 | Boc-N-Methyl-Tyr(Bzl)-OH | Boc-2-Naphthylalanine | 4-ClPhCH$_2$CO$_2$H | 502 | 28 | 55 |

-continued

| Cpd | R1: Amino acid | R2: Amino acid | R3: Carboxylic acid | MW | Yield |
|---|---|---|---|---|---|
| 2 | Boc-Ser(OBzl) | Boc-Tyr(OEt) | 3,4-Di-Cl-phenylacetic acid | 440 | 26 |
| 3 | Boc-Ser(OBzl) | Boc-Tyr(OEt) | 3-Cl-phenylacetic acid | 406 | 19 |
| 5 | Boc-Ser(OBzl) | Boc-Tyr(OEt) | 4-Cl-phenylacetic acid | 406 | 24 |
| 6 | Boc-Ser(OBzl) | Boc-Tyr(OEt) | 4-Br-phenylacetic acid | 450 | 19 |
| 7 | Boc-Ser(OBzl) | Boc-Tyr(OEt) | p-Tolylacetic acid | 385 | 19 |
| 9 | Boc-Ser(OBzl) | Boc-4-CF3-Phe | 3,4-Di-Cl-phenylacetic acid | 464 | 35 |
| 10 | Boc-Ser(OBzl) | Boc-4-CF3-Phe | 3-Cl-phenylacetic acid | 430 | 27 |
| 12 | Boc-Ser(OBzl) | Boc-4-CF3-Phe | 4-Cl-phenylacetic acid | 430 | 24 |
| 13 | Boc-Ser(OBzl) | Boc-4-CF3-Phe | 4-Br-phenylacetic acid | 474 | 31 |
| 14 | Boc-Ser(OBzl) | Boc-4-CF3-Phe | p-Tolylacetic acid | 409 | 23 |
| 16 | Boc-Ser(OBzl) | Boc-3,4-Di-OMe-Phe | 3,4-Di-Cl-phenylacetic acid | 456 | 23 |
| 17 | Boc-Ser(OBzl) | Boc-3,4-Di-OMe-Phe | 3-Cl-phenylacetic acid | 422 | 25 |
| 19 | Boc-Ser(OBzl) | Boc-3,4-Di-OMe-Phe | 4-Cl-phenylacetic acid | 422 | 27 |
| 20 | Boc-Ser(OBzl) | Boc-3,4-Di-OMe-Phe | 4-Br-phenylacetic acid | 466 | 15 |
| 21 | Boc-Ser(OBzl) | Boc-3,4-Di-OMe-Phe | p-Tolylacetic acid | 401 | 29 |
| 23 | Boc-Ser(OBzl) | Boc-4-tBu-Phe | 3,4-Di-Cl-phenylacetic acid | 452 | 26 |
| 24 | Boc-Ser(OBzl) | Boc-4-tBu-Phe | 3-Cl-phenylacetic acid | 418 | 30 |
| 26 | Boc-Ser(OBzl) | Boc-4-tBu-Phe | 4-Cl-phenylacetic acid | 418 | 28 |
| 27 | Boc-Ser(OBzl) | Boc-4-tBu-Phe | 4-Br-phenylacetic acid | 462 | 21 |
| 28 | Boc-Ser(OBzl) | Boc-4-tBu-Phe | p-Tolylacetic acid | 397 | 36 |
| 30 | Boc-Ser(OBzl) | Boc-N-Me-Tyr(Me) | 3,4-Di-Cl-phenylacetic acid | 440 | 29 |
| 31 | Boc-Ser(OBzl) | Boc-N-Me-Tyr(Me) | 3-Cl-phenylacetic acid | 406 | 29 |
| 33 | Boc-Ser(OBzl) | Boc-N-Me-Tyr(Me) | 4-Cl-phenylacetic acid | 406 | 28 |
| 34 | Boc-Ser(OBzl) | Boc-N-Me-Tyr(Me) | 4-Br-phenylacetic acid | 450 | 20 |
| 35 | Boc-Ser(OBzl) | Boc-N-Me-Tyr(Me) | p-Tolylacetic acid | 385 | 27 |
| 37 | Boc-Met(O)2 | Boc-Tyr(OEt) | 3,4-Di-Cl-phenylacetic acid | 516 | 51 |
| 38 | Boc-Met(O)2 | Boc-Tyr(OEt) | 3-Cl-phenylacetic acid | 482 | 54 |
| 40 | Boc-Met(O)2 | Boc-Tyr(OEt) | 4-Cl-phenylacetic acid | 482 | 52 |
| 41 | Boc-Met(O)2 | Boc-Tyr(OEt) | 4-Br-phenylacetic acid | 526 | 43 |
| 42 | Boc-Met(O)2 | Boc-Tyr(OEt) | p-Tolylacetic acid | 461 | 45 |
| 44 | Boc-Met(O)2 | Boc-4-CF3-Phe | 3,4-Di-Cl-phenylacetic acid | 540 | 47 |
| 45 | Boc-Met(O)2 | Boc-4-CF3-Phe | 3-Cl-phenylacetic acid | 506 | 52 |
| 47 | Boc-Met(O)2 | Boc-4-CF3-Phe | 4-Cl-phenylacetic acid | 506 | 46 |
| 48 | Boc-Met(O)2 | Boc-4-CF3-Phe | 4-Br-phenylacetic acid | 550 | 55 |
| 49 | Boc-Met(O)2 | Boc-4-CF3-Phe | p-Tolylacetic acid | 485 | 41 |
| 51 | Boc-Met(O)2 | Boc-3,4-Di-OMe-Phe | 3,4-Di-Cl-phenylacetic acid | 532 | 63 |
| 52 | Boc-Met(O)2 | Boc-3,4-Di-OMe-Phe | 3-Cl-phenylacetic acid | 498 | 42 |
| 54 | Boc-Met(O)2 | Boc-3,4-Di-OMe-Phe | 4-Cl-phenylacetic acid | 498 | 51 |
| 55 | Boc-Met(O)2 | Boc-3,4-Di-OMe-Phe | 4-Br-phenylacetic acid | 542 | 53 |
| 56 | Boc-Met(O)2 | Boc-3,4-Di-OMe-Phe | p-Tolylacetic acid | 477 | 50 |
| 58 | Boc-Met(O)2 | Boc-4-tBu-Phe | 3,4-Di-Cl-phenylacetic acid | 528 | 63 |
| 59 | Boc-Met(O)2 | Boc-4-tBu-Phe | 3-Cl-phenylacetic acid | 494 | 58 |

-continued

| Cpd | R1: Amino acid | R2: Amino acid | R3: Carboxylic acid | MW | Yield |
|---|---|---|---|---|---|
| 61 | Boc-Met(O)2 | Boc-4-tBu-Phe | 4-Cl-phenylacetic acid | 494 | 65 |
| 62 | Boc-Met(O)2 | Boc-4-tBu-Phe | 4-Br-phenylacetic acid | 538 | 61 |
| 64 | Boc-Hyp | Boc-3,4-Di-OMe-Phe | 3-Cl-phenylacetic acid | 448 | 23 |
| 66 | Boc-Hyp | Boc-3,4-Di-OMe-Phe | 4-Cl-phenylacetic acid | 448 | 24 |
| 67 | Boc-Hyp | Boc-3,4-Di-OMe-Phe | 4-Br-phenylacetic acid | 492 | 29 |
| 68 | Boc-Hyp | Boc-3,4-Di-OMe-Phe | p-Tolylacetic acid | 427 | 21 |
| 70 | Boc-Hyp | Boc-4-tBu-Phe | 3,4-Di-Cl-phenylacetic acid | 478 | 43 |
| 71 | Boc-Hyp | Boc-4-tBu-Phe | 3-Cl-phenylacetic acid | 444 | 30 |
| 73 | Boc-Hyp | Boc-4-tBu-Phe | 4-Cl-phenylacetic acid | 444 | 28 |
| 74 | Boc-Hyp | Boc-4-tBu-Phe | 4-Br-phenylacetic acid | 488 | 31 |
| 75 | Boc-Hyp | Boc-4-tBu-Phe | p-Tolylacetic acid | 423 | 28 |
| 77 | Boc-Hyp | Boc-N-Me-Tyr(Me) | 3,4-Di-Cl-phenylacetic acid | 466 | 20 |
| 78 | Boc-Hyp | Boc-N-Me-Tyr(Me) | 3-Cl-phenylacetic acid | 432 | 18 |
| 80 | Boc-Hyp | Boc-N-Me-Tyr(Me) | 4-Cl-phenylacetic acid | 432 | 22 |
| 81 | Boc-Hyp | Boc-N-Me-Tyr(Me) | 4-Br-phenylacetic acid | 476 | 25 |
| 82 | Boc-Hyp | Boc-N-Me-Tyr(Me) | p-Tolylacetic acid | 411 | 20 |
| 84 | Boc-Hyp | Boc-Tyr(OEt) | 3,4-Di-Cl-phenylacetic acid | 466 | 35 |
| 85 | Boc-Hyp | Boc-Tyr(OEt) | 3-Cl-phenylacetic acid | 432 | 19 |
| 87 | Boc-Hyp | Boc-Tyr(OEt) | 4-Cl-phenylacetic acid | 432 | 24 |
| 88 | Boc-Hyp | Boc-Tyr(OEt) | 4-Br-phenylacetic acid | 476 | 16 |
| 89 | Boc-Hyp | Boc-Tyr(OEt) | p-Tolylacetic acid | 411 | 20 |
| 90 | Boc-Hyp | Boc-3,4-Di-OMe-Ph | 3,4-Di-Cl-phenylacetic acid | 482 | 31 |
| 91 | Boc-Met(O)2 | Boc-4-tBu-Phe | p-Tolylacetic acid | 473 | 57 |
| 93 | Boc-Met(O)2 | Boc-N-Me-Tyr(Me) | 3,4-Di-Cl-phenylacetic acid | 516 | 49 |
| 94 | Boc-Met(O)2 | Boc-N-Me-Tyr(Me) | 3-Cl-phenylacetic acid | 482 | 38 |
| 96 | Boc-Met(O)2 | Boc-N-Me-Tyr(Me) | 4-Cl-phenylacetic acid | 482 | 47 |
| 97 | Boc-Met(O)2 | Boc-N-Me-Tyr(Me) | 4-Br-phenylacetic acid | 526 | 41 |
| 98 | Boc-Met(O)2 | Boc-N-Me-Tyr(Me) | p-Tolylacetic acid | 461 | 44 |
| 99 | Boc-3-PyrAla | Boc-Tyr(OPr) | 4-Cl-phenylacetic acid | 481 | 36 |
| 100 | Boc-3-PyrAla | Boc-Tyr(OPr) | 4-Br-phenylacetic acid | 525 | 44 |
| 101 | Boc-Ser(OBzl) | Boc-Tyr(OPr) | 4-Cl-phenylacetic acid | 420 | 29 |
| 102 | Boc-Ser(OBzl) | Boc-Tyr(OPr) | 4-Br-phenylacetic acid | 464 | 21 |
| 103 | Boc-Hyp | Boc-Tyr(OPr) | 4-Cl-phenylacetic acid | 446 | 28 |
| 104 | Boc-Hyp | Boc-Tyr(OPr) | 4-Br-phenylacetic acid | 490 | 34 |
| 105 | Boc-Ser(Me) | Boc-Tyr(OPr) | 4-Cl-phenylacetic acid | 434 | 26 |
| 106 | Boc-Ser(Me) | Boc-Tyr(OPr) | 4-Br-phenylacetic acid | 478 | 23 |
| 107 | Boc-Met(O)2 | Boc-Tyr(OPr) | 4-Cl-phenylacetic acid | 496 | 39 |
| 108 | Boc-Met(O)2 | Boc-Tyr(OPr) | 4-Br-phenylacetic acid | 540 | 44 |

| Cpd | R1: Amino acid | R2: Amino acid | R3: Carboxylic acid | MW | Yield |
|---|---|---|---|---|---|
| 1 | BOC-L-Ser(Me)-OH | BOC-1-Naphthy-Ala | 4-ClPhCH$_2$CO$_2$H | 426 | 18 |
| 2 | BOC-L-Ser(Me)-OH | BOC-2-Naphthy-Ala | 4-ClPhCH$_2$CO$_2$H | 426 | 17 |
| 3 | BOC-L-Ser(Me)-OH | BOC-Ala(3,3-diphenyl)-OH | 4-ClPhCH$_2$CO$_2$H | 452 | 21 |
| 4 | BOC-L-Ser(Me)-OH | BOC-L-3,4-Dichloro-Phe | 4-ClPhCH$_2$CO$_2$H | 445 | 18 |
| 5 | BOC-L-Ser(Me)-OH | BOC-L-4,4'-Biphenylalanine | 4-ClPhCH$_2$CO$_2$H | 452 | 13 |
| 6 | BOC-L-Ser(Me)-OH | BOC-L-4-Bromophenylalanine | 4-ClPhCH$_2$CO$_2$H | 455 | 15 |
| 7 | BOC-L-Ser(Me)-OH | BOC-L-4-Chlorophenylalanine | 4-ClPhCH$_2$CO$_2$H | 411 | 17 |
| 8 | BOC-L-Ser(Me)-OH | BOC-L-homo-SER(Me)-OH | 4-ClPhCH$_2$CO$_2$H | 344 | 14 |
| 9 | BOC-L-Ser(Me)-OH | BOC-L-Phe-OH | 4-ClPhCH$_2$CO$_2$H | 376 | 15 |
| 11 | BOC-L-Ser(Me)-OH | Fmoc-L-homo-Tyr(Me)-OH | 4-ClPhCH$_2$CO$_2$H | 420 | 10 |
| 12 | BOC-L-Ser(Me)-OH | Fmoc-L-m-Tyr(Me) | 4-ClPhCH$_2$CO$_2$H | 406 | 16 |
| 13 | BOC-L-Ser(Me)-OH | Fmoc-L-o-Tyr(Me) | 4-ClPhCH$_2$CO$_2$H | 406 | 17 |

-continued

| Cpd | R1: Amino acid | R2: Amino acid | R3: Carboxylic acid | MW | Yield |
|---|---|---|---|---|---|
| 14 | BOC-L-Ser(Me)-OH | Fmoc-L-Phe(4-Et) | 4-ClPhCH$_2$CO$_2$H | 404 | 17 |
| 15 | BOC-L-Ser(Me)-OH | Fmoc-L-Phe(4-iPr) | 4-ClPhCH$_2$CO$_2$H | 418 | 17 |
| 16 | BOC-L-Met(O)2-OH | BOC-1-Naphthy-Ala | 4-ClPhCH$_2$CO$_2$H | 488 | 31 |
| 17 | BOC-L-Met(O)2-OH | BOC-2-Naphthy-Ala | 4-ClPhCH$_2$CO$_2$H | 488 | 32 |
| 18 | BOC-L-Met(O)2-OH | BOC-Ala(3,3-diphenyl)-OH | 4-ClPhCH$_2$CO$_2$H | 514 | 31 |
| 19 | BOC-L-Met(O)2-OH | BOC-L-3,4-Dichloro-Phe | 4-ClPhCH$_2$CO$_2$H | 507 | 32 |
| 20 | BOC-L-Met(O)2-OH | BOC-L-4,4'-Biphenylalanine | 4-ClPhCH$_2$CO$_2$H | 514 | 32 |
| 21 | BOC-L-Met(O)2-OH | BOC-L-4-Bromophenylalanine | 4-ClPhCH$_2$CO$_2$H | 517 | 30 |
| 22 | BOC-L-Met(O)2-OH | BOC-L-4-Chlorophenylalanine | 4-ClPhCH$_2$CO$_2$H | 473 | 30 |
| 23 | BOC-L-Met(O)2-OH | BOC-L-homo-SER(Me)-OH | 4-ClPhCH$_2$CO$_2$H | 406 | 26 |
| 24 | BOC-L-Met(O)2-OH | BOC-L-Phe-OH | 4-ClPhCH$_2$CO$_2$H | 438 | 26 |
| 26 | BOC-L-Met(O)2-OH | Fmoc-L-homo-Tyr(Me)-OH | 4-ClPhCH$_2$CO$_2$H | 482 | 12 |
| 27 | BOC-L-Met(O)2-OH | Fmoc-L-m-Tyr(Me) | 4-ClPhCH$_2$CO$_2$H | 468 | 29 |
| 28 | BOC-L-Met(O)2-OH | Fmoc-L-o-Tyr(Me) | 4-ClPhCH$_2$CO$_2$H | 468 | 29 |
| 29 | BOC-L-Met(O)2-OH | Fmoc-L-Phe(4-Et) | 4-ClPhCH$_2$CO$_2$H | 466 | 28 |
| 30 | BOC-L-Met(O)2-OH | Fmoc-L-Phe(4-iPr) | 4-ClPhCH$_2$CO$_2$H | 480 | 32 |
| 31 | BOC-L-3-Pyridylala | BOC-1-Naphthy-Ala | 4-ClPhCH$_2$CO$_2$H | 473 | 88 |
| 32 | BOC-L-3-Pyridylala | BOC-2-Naphthy-Ala | 4-ClPhCH$_2$CO$_2$H | 473 | 74 |
| 33 | BOC-L-3-Pyridylala | BOC-Ala(3,3-diphenyl)-OH | 4-ClPhCH$_2$CO$_2$H | 499 | 80 |
| 34 | BOC-L-3-Pyridylala | BOC-L-3,4-Dichloro-Phe | 4-ClPhCH$_2$CO$_2$H | 492 | 54 |
| 35 | BOC-L-3-Pyridylala | BOC-L-4,4'-Biphenylalanine | 4-ClPhCH$_2$CO$_2$H | 499 | 82 |
| 36 | BOC-L-3-Pyridylala | BOC-L-4-Bromophenylalanine | 4-ClPhCH$_2$CO$_2$H | 502 | 68 |
| 37 | BOC-L-3-Pyridylala | BOC-L-4-Chlorophenylalanine | 4-ClPhCH$_2$CO$_2$H | 458 | 66 |
| 38 | BOC-L-3-Pyridylala | BOC-L-homo-SER(Me)-OH | 4-ClPhCH$_2$CO$_2$H | 391 | 68 |
| 39 | BOC-L-3-Pyridylala | BOC-L-Phe-OH | 4-ClPhCH$_2$CO$_2$H | 423 | 67 |
| 41 | BOC-L-3-Pyridylala | Fmoc-L-homo-Tyr(Me)-OH | 4-ClPhCH$_2$CO$_2$H | 467 | 68 |
| 42 | BOC-L-3-Pyridylala | Fmoc-L-m-Tyr(Me) | 4-ClPhCH$_2$CO$_2$H | 453 | 72 |
| 43 | BOC-L-3-Pyridylala | Fmoc-L-o-Tyr(Me) | 4-ClPhCH$_2$CO$_2$H | 453 | 64 |
| 44 | BOC-L-3-Pyridylala | Fmoc-L-Phe(4-Et) | 4-ClPhCH$_2$CO$_2$H | 451 | 66 |
| 45 | BOC-L-3-Pyridylala | Fmoc-L-Phe(4-iPr) | 4-ClPhCH$_2$CO$_2$H | 465 | 74 |
| 46 | BOC-L-Tic(OH)-OH | BOC-1-Naphthy-Ala | 4-ClPhCH$_2$CO$_2$H | 500 | 32 |
| 21 | BOC-L-Tic(OH)-OH | BOC-2-Naphthy-Ala | 4-ClPhCH$_2$CO$_2$H | 500 | 31 |
| 48 | BOC-L-Tic(OH)-OH | BOC-Ala(3,3-diphenyl)-OH | 4-ClPhCH$_2$CO$_2$H | 526 | 36 |
| 49 | BOC-L-Tic(OH)-OH | BOC-L-3,4-Dichloro-Phe | 4-ClPhCH$_2$CO$_2$H | 519 | 42 |
| 6 | BOC-L-Tic(OH)-OH | BOC-L-4,4'-Biphenylalanine | 4-ClPhCH$_2$CO$_2$H | 526 | 86 |
| 51 | BOC-L-Tic(OH)-OH | BOC-L-4-Bromophenylalanine | 4-ClPhCH$_2$CO$_2$H | 529 | 39 |
| 52 | BOC-L-Tic(OH)-OH | BOC-L-4-Chlorophenylalanine | 4-ClPhCH$_2$CO$_2$H | 485 | 33 |
| 53 | BOC-L-Tic(OH)-OH | BOC-L-homo-SER(Me)-OH | 4-ClPhCH$_2$CO$_2$H | 418 | 25 |

-continued

| Cpd | R1: Amino acid | R2: Amino acid | R3: Carboxylic acid | MW | Yield |
|---|---|---|---|---|---|
| 54 | BOC-L-Tic(OH)-OH | BOC-L-Phe-OH | 4-ClPhCH$_2$CO$_2$H | 450 | 32 |
| 55 | BOC-L-Tic(OH)-OH | Fmoc-L-homo-Tyr(Me)-OH | 4-ClPhCH$_2$CO$_2$H | 494 | 35 |
| 56 | BOC-L-Tic(OH)-OH | Fmoc-L-m-Tyr(Me) | 4-ClPhCH$_2$CO$_2$H | 480 | 36 |
| 57 | BOC-L-Tic(OH)-OH | Fmoc-L-o-Tyr(Me) | 4-ClPhCH$_2$CO$_2$H | 480 | 39 |
| 58 | BOC-L-Tic(OH)-OH | Fmoc-L-Phe(4-Et) | 4-ClPhCH$_2$CO$_2$H | 478 | 50 |
| 59 | BOC-L-Tic(OH)-OH | Fmoc-L-Phe(4-iPr) | 4-ClPhCH$_2$CO$_2$H | 492 | 32 |
| 60 | BOC-L-Ser(OBzl) | BOC-1-Naphthy-Ala | 4-ClPhCH$_2$CO$_2$H | 412 | 56 |
| 61 | BOC-L-Ser(OBzl) | BOC-2-Naphthy-Ala | 4-ClPhCH$_2$CO$_2$H | 412 | 64 |
| 62 | BOC-L-Ser(OBzl) | BOC-Ala(3,3-diphenyl)-OH | 4-ClPhCH$_2$CO$_2$H | 438 | 61 |
| 63 | BOC-L-Ser(OBzl) | BOC-L-3,4-Dichloro-Phe | 4-ClPhCH$_2$CO$_2$H | 431 | 53 |
| 64 | BOC-L-Ser(OBzl) | BOC-L-4,4'-Biphenylalanine | 4-ClPhCH$_2$CO$_2$H | 438 | 59 |
| 65 | BOC-L-Ser(OBzl) | BOC-L-4-Bromophenylalanine | 4-ClPhCH$_2$CO$_2$H | 441 | 62 |
| 66 | BOC-L-Ser(OBzl) | BOC-L-4-Chlorophenylalanine | 4-ClPhCH$_2$CO$_2$H | 397 | 53 |
| 67 | BOC-L-Ser(OBzl) | BOC-L-homo-SER(Me)-OH | 4-ClPhCH$_2$CO$_2$H | 330 | 49 |
| 68 | BOC-L-Ser(OBzl) | BOC-L-Phe-OH | 4-ClPhCH$_2$CO$_2$H | 362 | 56 |
| 70 | BOC-L-Ser(OBzl) | Fmoc-L-homo-Tyr(Me)-OH | 4-ClPhCH$_2$CO$_2$H | 406 | 55 |
| 71 | BOC-L-Ser(OBzl) | Fmoc-L-m-Tyr(Me) | 4-ClPhCH$_2$CO$_2$H | 392 | 42 |
| 72 | BOC-L-Ser(OBzl) | Fmoc-L-o-Tyr(Me) | 4-ClPhCH$_2$CO$_2$H | 392 | 56 |
| 73 | BOC-L-Ser(OBzl) | Fmoc-L-Phe(4-Et) | 4-ClPhCH$_2$CO$_2$H | 390 | 49 |
| 74 | BOC-L-Ser(OBzl) | Fmoc-L-Phe(4-iPr) | 4-ClPhCH$_2$CO$_2$H | 404 | 47 |
| 76 | BOC-L-Hyp-OH | BOC-1-Naphthy-Ala | 4-ClPhCH$_2$CO$_2$H | 438 | 23 |
| 77 | BOC-L-Hyp-OH | BOC-2-Naphthy-Ala | 4-ClPhCH$_2$CO$_2$H | 438 | 27 |
| 78 | BOC-L-Hyp-OH | BOC-Ala(3,3-diphenyl)-OH | 4-ClPhCH$_2$CO$_2$H | 464 | 27 |
| 79 | BOC-L-Hyp-OH | BOC-L-3,4-Dichloro-Phe | 4-ClPhCH$_2$CO$_2$H | 457 | 30 |
| 80 | BOC-L-Hyp-OH | BOC-L-4,4'-Biphenylalanine | 4-ClPhCH$_2$CO$_2$H | 464 | 35 |
| 81 | BOC-L-Hyp-OH | BOC-L-4-Bromophenylalanine | 4-ClPhCH$_2$CO$_2$H | 467 | 33 |
| 82 | BOC-L-Hyp-OH | BOC-L-4-Chlorophenylalanine | 4-ClPhCH$_2$CO$_2$H | 423 | 24 |
| 83 | BOC-L-Hyp-OH | BOC-L-homo-SER(Me)-OH | 4-ClPhCH$_2$CO$_2$H | 356 | 28 |
| 84 | BOC-L-Hyp-OH | BOC-L-Phe-OH | 4-ClPhCH$_2$CO$_2$H | 388 | 31 |
| 86 | BOC-L-Hyp-OH | Fmoc-L-homo-Tyr(Me)-OH | 4-ClPhCH$_2$CO$_2$H | 432 | 27 |
| 87 | BOC-L-Hyp-OH | Fmoc-L-m-Tyr(Me) | 4-ClPhCH$_2$CO$_2$H | 418 | 31 |
| 88 | BOC-L-Hyp-OH | Fmoc-L-o-Tyr(Me) | 4-ClPhCH$_2$CO$_2$H | 418 | 31 |
| 89 | BOC-L-Hyp-OH | Fmoc-L-Phe(4-Et) | 4-ClPhCH$_2$CO$_2$H | 416 | 35 |
| 90 | BOC-L-Hyp-OH | Fmoc-L-Phe(4-iPr) | 4-ClPhCH$_2$CO$_2$H | 430 | 16 |
| 91 | BOC-L-Dimethyl-Orn | BOC-2-Naphthy-Ala | 4-ClPhCH$_2$CO$_2$H | 467 | 2 |
| 92 | BOC-L-Dimethyl-Orn | BOC-2-Naphthy-Ala | 4-ClPhCH$_2$CO$_2$H | 511 | 2 |

-continued

| Cpd | R1: Amino acid | R2: Amino acid | R3: Carboxylic acid | MW | Yield |
|---|---|---|---|---|---|
| 93 | BOC-L-Dimethyl-Orn | BOC-L-3,4-Dichloro-Phe | 4-ClPhCH$_2$CO$_2$H | 486 | 3 |
| 94 | BOC-L-Dimethyl-Orn | BOC-L-3,4-Dichloro-Phe | 4-ClPhCH$_2$CO$_2$H | 529 | 0 |
| 95 | BOC-L-Dimethyl-Orn | BOC-L-4,4'-Biphenylalanine | 4-ClPhCH$_2$CO$_2$H | 493 | 0 |
| 96 | BOC-L-Dimethyl-Orn | BOC-L-4,4'-Biphenylalanine | 4-ClPhCH$_2$CO$_2$H | 537 | 2 |
| 97 | BOC-L-Dimethyl-Orn | Fmoc-L-Phe(4-Et) | 4-ClPhCH$_2$CO$_2$H | 445 | 3 |
| 98 | BOC-L-Dimethyl-Orn | Fmoc-L-Phe(4-Et) | 4-ClPhCH$_2$CO$_2$H | 489 | 1 |
| 99 | BOC-L-Dimethyl-Orn | Fmoc-L-Phe(4-iPr) | 4-ClPhCH$_2$CO$_2$H | 503 | 0 |

| Cpd | R1: Amino acid | R2: Amino acid | R3: Carboxylic acid | MW | Yield |
|---|---|---|---|---|---|
| 1 | BOC-L-3-Pyridylala | Boc-Tyr(Et)-OH | 2,4-di-Chloro-phenylacetic acid | 501 | 72 |
| 2 | BOC-L-3-Pyridylala | Boc-Tyr(Et)-OH | 2-Cl-phenylacetic acid | 467 | 82 |
| 3 | BOC-L-3-Pyridylala | Boc-Tyr(Et)-OH | 3-(trifluoromethyl)phenylacetic acid | 500 | 68 |
| 4 | BOC-L-3-Pyridylala | Boc-Tyr(Et)-OH | 3,4-di-Methoxy-phenylacetic acid | 492 | 74 |
| 5 | BOC-L-3-Pyridylala | Boc-Tyr(Et)-OH | 3,5-di-(trifluoromethyl)phenylacetic acid | 568 | 60 |
| 6 | BOC-L-3-Pyridylala | Boc-Tyr(Et)-OH | 3,5-di-fluoropenl-acetic acid | 468 | 73 |
| 7 | BOC-L-3-Pyridylala | Boc-Tyr(Et)-OH | 3-Ethoxy-4-Hydroxyphenyl-acetic acid | 492 | 73 |
| 8 | BOC-L-3-Pyridylala | Boc-Tyr(Et)-OH | 3-Methoxy-phenylacetic acid | 462 | 65 |
| 9 | BOC-L-3-Pyridylala | Boc-Tyr(Et)-OH | 4-(dimethylamino)phenyl-acetic acid | 475 | 67 |
| 10 | BOC-L-3-Pyridylala | Boc-Tyr(Et)-OH | 4-(methylthio)-phenylacetic acid | 478 | 67 |
| 12 | BOC-L-3-Pyridylala | Boc-Tyr(Et)-OH | 4-biphenyl-acetic acid | 508 | 70 |
| 13 | BOC-L-3-Pyridylala | Boc-Tyr(Et)-OH | 4-Bromophenyl-acetic acid | 511 | 71 |
| 14 | BOC-L-3-Pyridylala | Boc-Tyr(Et)-OH | 4-Fluorophenyl-acetic acid | 450 | 56 |
| 15 | BOC-L-3-Pyridylala | Boc-Tyr(Et)-OH | 4-Methoxy-phenylacetic acid | 462 | 60 |
| 16 | BOC-L-3-Pyridylala | Boc-Tyr(Et)-OH | phenylacetic acid | 432 | 64 |
| 18 | BOC-L-Tic(OH)-OH | Boc-Tyr(Et)-OH | 2,4-di-Chloro-phenylacetic acid | 528 | 43 |
| 19 | BOC-L-Tic(OH)-OH | Boc-Tyr(Et)-OH | 2-Cl-phenyl-acetic acid | 494 | 42 |
| 20 | BOC-L-Tic(OH)-OH | Boc-Tyr(Et)-OH | 3-(trifluoromethyl)phenyl-acetic acid | 527 | 48 |
| 21 | BOC-L-Tic(OH)-OH | Boc-Tyr(Et)-OH | 3,4-di-Methoxy-phenylacetic acid | 519 | 34 |
| 22 | BOC-L-Tic(OH)-OH | Boc-Tyr(Et)-OH | 3,5-di-(trifluoromethyl)phenyl-acetic acid | 595 | 63 |
| 23 | BOC-L-Tic(OH)-OH | Boc-Tyr(Et)-OH | 3,5-di-fluoropenl-acetic acid | 495 | 37 |
| 24 | BOC-L-Tic(OH)-OH | Boc-Tyr(Et)-OH | 3-Ethoxy-4-Hydroxyphenyl-acetic acid | 519 | 45 |
| 25 | BOC-L-Tic(OH)-OH | Boc-Tyr(Et)-OH | 3-Methoxy-phenylacetic acid | 489 | 40 |
| 26 | BOC-L-Tic(OH)-OH | Boc-Tyr(Et)-OH | 4-(dimethylamino)phenyl-acetic acid | 502 | 45 |
| 27 | BOC-L-Tic(OH)-OH | Boc-Tyr(Et)-OH | 4-(methylthio)-phenylacetic acid | 505 | 47 |
| 28 | BOC-L-Tic(OH)-OH | Boc-Tyr(Et)-OH | 4-(trifluoromethyl)phenyl-acetic acid | 527 | 40 |
| 29 | BOC-L-Tic(OH)-OH | Boc-Tyr(Et)-OH | 4-biphenyl-acetic acid | 535 | 41 |
| 30 | BOC-L-Tic(OH)-OH | Boc-Tyr(Et)-OH | 4-Bromophenyl-acetic acid | 538 | 57 |
| 31 | BOC-L-Tic(OH)-OH | Boc-Tyr(Et)-OH | 4-Fluorophenyl-acetic acid | 477 | 37 |
| 32 | BOC-L-Tic(OH)-OH | Boc-Tyr(Et)-OH | 4-Methoxy-phenylacetic acid | 489 | 29 |
| 33 | BOC-L-Tic(OH)-OH | Boc-Tyr(Et)-OH | phenylacetic acid | 459 | 34 |
| 35 | BOC-L-Ser(OBzl) | Boc-Tyr(Et)-OH | 2,4-di-Chloro-phenylacetic acid | 440 | 58 |
| 36 | BOC-L-Ser(OBzl) | Boc-Tyr(Et)-OH | 2-Cl-phenyl-acetic acid | 406 | 58 |
| 37 | BOC-L-Ser(OBzl) | Boc-Tyr(Et)-OH | 3-(trifluoromethyl)phenyl-acetic acid | 439 | 66 |
| 38 | BOC-L-Ser(OBzl) | Boc-Tyr(Et)-OH | 3,4-di-Methoxy-phenylacetic acid | 431 | 66 |
| 39 | BOC-L-Ser(OBzl) | Boc-Tyr(Et)-OH | 3,5-di-(trifluoromethyl)phenyl-acetic acid | 507 | 59 |
| 40 | BOC-L-Ser(OBzl) | Boc-Tyr(Et)-OH | 3,5-di-fluoropenl-acetic acid | 407 | 66 |
| 41 | BOC-L-Ser(OBzl) | Boc-Tyr(Et)-OH | 3-Ethoxy-4-Hydroxyphenyl-acetic acid | 431 | 62 |

-continued

| Cpd | R1: Amino acid | R2: Amino acid | R3: Carboxylic acid | MW | Yield |
|---|---|---|---|---|---|
| 42 | BOC-L-Ser(OBzl) | Boc-Tyr(Et)-OH | 3-Methoxy-phenylacetic acid | 401 | 60 |
| 43 | BOC-L-Ser(OBzl) | Boc-Tyr(Et)-OH | 4-(dimethyl-amino)phenyl-acetic acid | 414 | 61 |
| 44 | BOC-L-Ser(OBzl) | Boc-Tyr(Et)-OH | 4-(methylthio)-phenylacetic acid | 417 | 59 |
| 45 | BOC-L-Ser(OBzl) | Boc-Tyr(Et)-OH | 4-(trifluoro-methyl)phenyl-acetic acid | 439 | 64 |
| 46 | BOC-L-Ser(OBzl) | Boc-Tyr(Et)-OH | 4-biphenylacetic acid | 447 | 66 |
| 47 | BOC-L-Ser(OBzl) | Boc-Tyr(Et)-OH | 4-Bromophenyl-acetic acid | 450 | 57 |
| 49 | BOC-L-Ser(OBzl) | Boc-Tyr(Et)-OH | 4-Methoxy-phenylacetic acid | 401 | 65 |
| 50 | BOC-L-Ser(OBzl) | Boc-Tyr(Et)-OH | phenylacetic acid | 371 | 63 |
| 52 | BOC-L-Ser(Me)-OH | Boc-Tyr(Et)-OH | 2,4-di-Chloro-phenylacetic acid | 454 | 26 |
| 53 | BOC-L-Ser(Me)-OH | Boc-Tyr(Et)-OH | 2-Cl-phenyl-acetic acid | 420 | 23 |
| 54 | BOC-L-Ser(Me)-OH | Boc-Tyr(Et)-OH | 3-(trifluoro-methyl)phenyl-acetic acid | 453 | 27 |
| 55 | BOC-L-Ser(Me)-OH | Boc-Tyr(Et)-OH | 3,4-di-Methoxy-phenylacetic acid | 445 | 25 |
| 56 | BOC-L-Ser(Me)-OH | Boc-Tyr(Et)-OH | 3,5-di-(trifluoro-methyl)phenyl-acetic acid | 521 | 25 |
| 57 | BOC-L-Ser(Me)-OH | Boc-Tyr(Et)-OH | 3,5-di-fluoropenl-acetic acid | 421 | 30 |
| 58 | BOC-L-Ser(Me)-OH | Boc-Tyr(Et)-OH | 3-Ethoxy-4-Hydroxyphenyl-acetic acid | 445 | 23 |
| 59 | BOC-L-Ser(Me)-OH | Boc-Tyr(Et)-OH | 3-Methoxy-phenylacetic acid | 415 | 22 |
| 60 | BOC-L-Ser(Me)-OH | Boc-Tyr(Et)-OH | 4-(dimethyl-amino)phenyl-acetic acid | 428 | 27 |
| 61 | BOC-L-Ser(Me)-OH | Boc-Tyr(Et)-OH | 4-(methylthio)-phenylacetic acid | 431 | 31 |
| 62 | BOC-L-Ser(Me)-OH | Boc-Tyr(Et)-OH | 4-(trifluoro-methyl)phenyl-acetic acid | 453 | 25 |
| 63 | BOC-L-Ser(Me)-OH | Boc-Tyr(Et)-OH | 4-biphenylacetic acid | 461 | 26 |
| 64 | BOC-L-Ser(Me)-OH | Boc-Tyr(Et)-OH | 4-Bromophenyl-acetic acid | 464 | 25 |
| 65 | BOC-L-Ser(Me)-OH | Boc-Tyr(Et)-OH | 4-Fluorophenyl-acetic acid | 403 | 19 |
| 66 | BOC-L-Ser(Me)-OH | Boc-Tyr(Et)-OH | 4-Methoxy-phenylacetic acid | 415 | 20 |
| 67 | BOC-L-Ser(Me)-OH | Boc-Tyr(Et)-OH | phenylacetic acid | 385 | 21 |
| 69 | BOC-L-Met(O)2-OH | Boc-Tyr(Et)-OH | 2,4-di-Chloro-phenylacetic acid | 516 | 31 |
| 70 | BOC-L-Met(O)2-OH | Boc-Tyr(Et)-OH | 2-Cl-phenylacetic acid | 482 | 35 |
| 71 | BOC-L-Met(O)2-OH | Boc-Tyr(Et)-OH | 3-(trifluoro-methyl)phenyl-acetic acid | 515 | 42 |
| 72 | BOC-L-Met(O)2-OH | Boc-Tyr(Et)-OH | 3,4-di-Methoxy-phenylacetic acid | 507 | 33 |
| 73 | BOC-L-Met(O)2-OH | Boc-Tyr(Et)-OH | 3,5-di-(trifluoro-methyl)phenyl-acetic acid | 583 | 38 |
| 74 | BOC-L-Met(O)2-OH | Boc-Tyr(Et)-OH | 3,5-di-fluoropenl-acetic acid | 483 | 27 |
| 75 | BOC-L-Met(O)2-OH | Boc-Tyr(Et)-OH | 3-Ethoxy-4-Hydroxyphenyl-acetic acid | 507 | 46 |
| 76 | BOC-L-Met(O)2-OH | Boc-Tyr(Et)-OH | 3-Methoxy-phenylacetic acid | 477 | 29 |
| 77 | BOC-L-Met(O)2-OH | Boc-Tyr(Et)-OH | 4-(dimethyl-amino)phenyl-acetic acid | 490 | 32 |
| 78 | BOC-L-Met(O)2-OH | Boc-Tyr(Et)-OH | 4-(methylthio)-phenylacetic acid | 493 | 40 |
| 79 | BOC-L-Met(O)2-OH | Boc-Tyr(Et)-OH | 4-(trifluoro-methyl)phenyl-acetic acid | 515 | 31 |
| 80 | BOC-L-Met(O)2-OH | Boc-Tyr(Et)-OH | 4-biphenylacetic acid | 523 | 35 |
| 81 | BOC-L-Met(O)2-OH | Boc-Tyr(Et)-OH | 4-Bromophenyl-acetic acid | 526 | 25 |
| 82 | BOC-L-Met(O)2-OH | Boc-Tyr(Et)-OH | 4-Fluorophenyl-acetic acid | 465 | 30 |
| 83 | BOC-L-Met(O)2-OH | Boc-Tyr(Et)-OH | 4-Methoxy-phenylacetic acid | 477 | 31 |
| 84 | BOC-L-Met(O)2-OH | Boc-Tyr(Et)-OH | phenylacetic acid | 447 | 21 |
| 86 | BOC-L-Hyp-OH | Boc-Tyr(Et)-OH | 2,4-Di-Chloro-phenylacetic acid | 466 | 20 |
| 87 | BOC-L-Hyp-OH | Boc-Tyr(Et)-OH | 2-Cl-phenylacetic acid | 432 | 19 |
| 88 | BOC-L-Hyp-OH | Boc-Tyr(Et)-OH | 3-(Trifluoro-methyl)phenyl-acetic acid | 465 | 17 |
| 89 | BOC-L-Hyp-OH | Boc-Tyr(Et)-OH | 3,4-Di-Methoxy-phenylacetic acid | 457 | 12 |
| 90 | BOC-L-Hyp-OH | Boc-Tyr(Et)-OH | 3,5-Di-(trifluoro-methyl)phenyl-acetic acid | 533 | 18 |
| 91 | BOC-L-Hyp-OH | Boc-Tyr(Et)-OH | 3,5-Di-fluoro-penlacetic acid | 433 | 21 |
| 92 | BOC-L-Hyp-OH | Boc-Tyr(Et)-OH | 3-Ethoxy-4-Hydroxyphenyl-acetic acid | 457 | 17 |
| 93 | BOC-L-Hyp-OH | Boc-Tyr(Et)-OH | 3-Methoxy-phenylacetic acid | 427 | 16 |
| 94 | BOC-L-Hyp-OH | Boc-Tyr(Et)-OH | 4-(Dimethyl-amino)phenyl-acetic acid | 440 | 21 |
| 95 | BOC-L-Hyp-OH | Boc-Tyr(Et)-OH | 4-(Methylthio)-phenylacetic acid | 443 | 18 |
| 96 | BOC-L-Hyp-OH | Boc-Tyr(Et)-OH | 4-Biphenylacetic acid | 473 | 18 |
| 97 | BOC-L-Hyp-OH | Boc-Tyr(Et)-OH | 4-Bromophenyl-acetic acid | 476 | 20 |
| 98 | BOC-L-Hyp-OH | Boc-Tyr(Et)-OH | 4-Fluorophenyl-acetic acid | 415 | 17 |
| 99 | BOC-L-Hyp-OH | Boc-Tyr(Et)-OH | 4-Methoxy-phenylacetic acid | 427 | 17 |
| 100 | BOC-L-Hyp-OH | Boc-Tyr(Et)-OH | Phenylacetic acid | 397 | 17 |
| 102 | BOC-L-Dimethyl-Orn | Boc-Tyr(Et)-OH | 4-Fluorophenyl-acetic acid | 445 | 7 |
| 103 | BOC-L-Dimethyl-Orn | Boc-Tyr(Et)-OH | 4-Fluorophenyl-acetic acid | 489 | 1 |
| 104 | BOC-L-Dimethyl-Orn | Boc-Tyr(Et)-OH | 4-Methoxy-phenylacetic acid | 457 | 4 |
| 105 | BOC-L-Dimethyl-Orn | Boc-Tyr(Et)-OH | 4-Methoxy-phenylacetic acid | 501 | 2 |
| 106 | BOC-L-Dimethyl-Orn | Boc-Tyr(Et)-OH | Phenylacetic acid | 427 | 6 |
| 107 | BOC-L-Dimethyl-Orn | Boc-Tyr(Et)-OH | Phenylacetic acid | 471 | 1 |
| 108 | BOC-L-Dimethyl-Orn | Boc-Tyr(Et)-OH | p-Toluic acid | 441 | 4 |
| 109 | BOC-L-Dimethyl-Orn | Boc-Tyr(Et)-OH | p-Toluic acid | 485 | 1 |

| Cpd | R1: Amino acid | R2: Amino acid | R3: Carboxylic acid | R4: Sulfonyl chloride | MW | Yield |
|---|---|---|---|---|---|---|
| 1 | BOC-DAP(FMOC) | Boc-Tyr(Et)-OH | p-Cl-phenyl-acetic acid | 2-thiophenesulfonyl chloride | 550 | 25.1 |
| 2 | BOC-DAP(FMOC) | Boc-Tyr(Et)-OH | p-Cl-phenyl-acetic acid | 4-methoxybenzene-sulfonyl chloride | 574 | 22.6 |
| 3 | BOC-DAP(FMOC) | Boc-Tyr(Et)-OH | p-Cl-phenyl-acetic acid | benzenesulfonyl chloride | 544 | 28.7 |
| 4 | BOC-DAP(FMOC) | Boc-Tyr(Et)-OH | p-Cl-phenyl-acetic acid | 4-butoxysulfonyl chloride | 616 | 27.0 |
| 5 | BOC-DAP(FMOC) | Boc-Tyr(Et)-OH | p-Cl-phenyl-acetic acid | methanesulfonyl chloride | 482 | 31.0 |
| 6 | BOC-DAP(FMOC) | Boc-Tyr(Et)-OH | p-Cl-phenyl-acetic acid | 2-thiophenesulfonyl chloride | 564 | 23.2 |
| 7 | BOC-DAP(FMOC) | Boc-Tyr(Et)-OH | p-Cl-phenyl-acetic acid | 4-methoxybenzene-sulfonyl chloride | 588 | 30.2 |
| 8 | BOC-DAP(FMOC) | Boc-Tyr(Et)-OH | p-Cl-phenyl-acetic acid | benzenesulfonyl chloride | 558 | 21.5 |
| 9 | BOC-DAP(FMOC) | Boc-Tyr(Et)-OH | p-Cl-phenyl-acetic acid | 4-butoxysulfonyl chloride | 630 | 30.0 |
| 10 | BOC-DAP(FMOC) | Boc-Tyr(Et)-OH | p-Cl-phenyl-acetic acid | methanesulfonyl chloride | 496 | 28.8 |
| 11 | BOC-Orn(FMOC) | Boc-Tyr(Et)-OH | p-Cl-phenyl-acetic acid | 2-thiophenesulfonyl chloride | 578 | 33.1 |
| 12 | BOC-Orn(FMOC) | Boc-Tyr(Et)-OH | p-Cl-phenyl-acetic acid | 4-methoxybenzene-sulfonyl chloride | 602 | 33.9 |
| 13 | BOC-Orn(FMOC) | Boc-Tyr(Et)-OH | p-Cl-phenyl-acetic acid | benzenesulfonyl chloride | 572 | 29.4 |
| 14 | BOC-Orn(FMOC) | Boc-Tyr(Et)-OH | p-Cl-phenyl-acetic acid | 4-butoxyfulfonyl chloride | 644 | 35.8 |
| 15 | BOC-Orn(FMOC) | Boc-Tyr(Et)-OH | p-Cl-phenyl-acetic acid | methanesulfonyl chloride | 510 | 16.5 |

| Cmpd | R1 | R2 | R3 | R4 | MW | Yield |
|---|---|---|---|---|---|---|
| 1 | Boc-Glu(OFm)-OH | Boc-Tyr(Et)-OH | 4-chlorophenyl-acetic acid | morpholine | 502 | 40 |
| 2 | Boc-Glu(OFm)-OH | Boc-Tyr(Et)-OH | 4-chlorophenyl-acetic acid | cyclopropylamine | 472 | 23 |
| 3 | Boc-Glu(OFm)-OH | Boc-Tyr(Et)-OH | 4-chlorophenyl-acetic acid | tetrahydrofurfuryl-amine | 516 | 27 |
| 4 | Boc-Glu(OFm)-OH | Boc-Tyr(Et)-OH | 4-chlorophenyl-acetic acid | 4-hydroxypiperidine | 516 | 35 |
| 5 | Boc-Glu(OFm)-OH | Boc-Tyr(Et)-OH | 4-chlorophenyl-acetic acid | 2-amino-2-methyl-1-propanol | 504 | 30 |
| 6 | Boc-Glu(OFm)-OH | Boc-Tyr(Et)-OH | 4-chlorophenyl-acetic acid | 2-(methylamino)-ethanol | 490 | 27 |
| 7 | Boc-Glu(OFm)-OH | Boc-Tyr(Et)-OH | 4-chlorophenyl-acetic acid | N-methylcyclohexyl amine | 528 | 35 |
| 8 | Boc-Asp(OFm)-OH | Boc-Tyr(Et)-OH | 4-chlorophenyl-acetic acid | morpholine | 488 | 53 |
| 9 | Boc-Asp(OFm)-OH | Boc-Tyr(Et)-OH | 4-chlorophenyl-acetic acid | cyclopropylamine | 458 | 12 |
| 10 | Boc-Asp(OFm)-OH | Boc-Tyr(Et)-OH | 4-chlorophenyl-acetic acid | tetrahydrofurfuryl-amine | 502 | 35 |
| 11 | Boc-Asp(OFm)-OH | Boc-Tyr(Et)-OH | 4-chlorophenyl-acetic acid | 4-hydroxypiperidine | 502 | 14 |
| 12 | Boc-Asp(OFm)-OH | Boc-Tyr(Et)-OH | 4-chlorophenyl-acetic acid | 2-amino-2-methyl-1-propanol | 490 | 28 |

-continued

| Cmpd | R1 | R2 | R3 | R4 | MW | Yield |
|---|---|---|---|---|---|---|
| 13 | Boc-Asp(OFm)-OH | Boc-Tyr(Et)-OH | 4-chlorophenyl-acetic acid | 2-(methylamino)-ethanol | 476 | 30.0 |
| 14 | Boc-Asp(OFm)-OH | Boc-Tyr(Et)-OH | 4-chlorophenyl-acetic acid | N-methylcyclohexyl amine | 514 | 26.0 |
| 15 | Boc-Glu(OFm)-OH | Boc-Tyr(Et)-OH | 4-bromophenyl-acetic acid | morpholine | 547 | 64.3 |
| 16 | Boc-Glu(OFm)-OH | Boc-Tyr(Et)-OH | 4-bromophenyl-acetic acid | cyclopropylamine | 517 | 62.3 |
| 17 | Boc-Glu(OFm)-OH | Boc-Tyr(Et)-OH | 4-bromophenyl-acetic acid | tetrahydrofurfuryl-amine | 561 | 70.7 |
| 18 | Boc-Glu(OFm)-OH | Boc-Tyr(Et)-OH | 4-bromophenyl-acetic acid | N-methylcyclo-hexylamine | 573 | 70.9 |
| 19 | Boc-Glu(OFm)-OH | Boc-Tyr(Et)-OH | 4-bromophenyl-acetic acid | 3-methoxypropyl-amine | 549 | 51.9 |
| 20 | Boc-Glu(OFm)-OH | Boc-Tyr(Et)-OH | 4-bromophenyl-acetic acid | 4-hydroxypiperidine | 561 | 55.4 |
| 21 | Boc-Glu(OFm)-OH | Boc-Tyr(Et)-OH | 4-bromophenyl-acetic acid | 2-amino-2-methyl-1-propanol | 549 | 51.9 |
| 22 | Boc-Glu(OFm)-OH | Boc-Tyr(Et)-OH | 4-bromophenyl-acetic acid | 2-(methylamino)-ethanol | 535 | 51.9 |
| 23 | Boc-Glu(OFm)-OH | Boc-Tyr(Pr)-OH | 4-bromophenyl-acetic acid | morpholine | 561 | 61.9 |
| 24 | Boc-Glu(OFm)-OH | Boc-Tyr(Pr)-OH | 4-bromophenyl-acetic acid | cyclopropylamine | 531 | 64.5 |
| 25 | Boc-Glu(OFm)-OH | Boc-Tyr(Pr)-OH | 4-bromophenyl-acetic acid | tetrahydrofurfuryl-amine | 575 | 42.7 |
| 26 | Boc-Glu(OFm)-OH | Boc-Tyr(Pr)-OH | 4-bromophenyl-acetic acid | N-methylcyclo-hexylamine | 587 | 51 |
| 27 | Boc-Glu(OFm)-OH | Boc-Tyr(Pr)-OH | 4-bromophenyl-acetic acid | 3-methoxypropyl-amine | 563 | 60.8 |
| 28 | Boc-Glu(OFm)-OH | Boc-Tyr(Pr)-OH | 4-bromophenyl-acetic acid | 4-hydroxypiperidine | 575 | 60.6 |
| 29 | Boc-Glu(OFm)-OH | Boc-Tyr(Pr)-OH | 4-bromophenyl-acetic acid | 2-amino-2-methyl-1-propanol | 563 | 54.3 |
| 30 | Boc-Glu(OFm)-OH | Boc-Tyr(Pr)-OH | 4-bromophenyl-acetic acid | 2-(methylamino)-ethanol | 549 | 48.1 |
| 31 | Boc-Asp(OFm)-OH | Boc-Tyr(Et)-OH | 4-bromophenyl-acetic acid | morpholine | 533 | 52.1 |

EXAMPLE II

Melanocortin Receptor Assays

This example describes methods for assaying binding to MC receptors.

A. Cell Culture and Preparation:

HEK-293 cell lines were transfected with the human melanocortin receptors hMC1, hMC3, and hMC4 were obtained from Dr. Ira Gantz, as described in Gantz, I. et al., *Biochem. Biophys. Res. Comm.*, 3:1214-1220 (1994); Gantz et al., *J. Biol. Chem.*, 268:8246-8250 (1993); Gantz et al., *J. Biol. Chem.*, 268:15174-15179 (1993); and Haskell-Leuvano et al., *Biochem. Biophys. Res. Comm.*, 204:1137-1142 (1994).

Vectors for construction of an hMC-5 expressing cell line were also obtained from Dr. Ira Gantz, as described in the above references, and a line of HEK-293 cells expressing hMC-5 was constructed. HEK-293 cell lines were maintained in DMEM containing 25 mM HEPES, sodium pyruvate, 10% Cosmic Calf serum, 100 units/ml penicillin, 100 μg/ml streptomycin, 2 mM glutamine, non-essential amino acids, vitamins and 0.2 mg/ml G418 to maintain selection.

B. Membrane Preparation:

HEK-293 cells stably expressing the MC Receptors were grown to confluency in 175 cm$^2$ flasks. 3 flasks were washed in 30 ml room temperature phosphate buffered saline (Cellgro) per flask, and harvested using a rubber scraper in 5 ml ice-cold PBS per flask. The cells were combined into one test tube, homogenized using a Polytron homogenizer (3 bursts of 10 seconds) and centrifuged at 32,000× g for 20 min at 4° C.

Membranes were washed as follows: the pellet obtained after centrifugation was resuspended in 20 ml ice-cold hypotonic buffer, (20 mM Tris-HCl, 5 mM EDTA, pH 7.7 at 4° C.), dispersed using a 8 strokes in a teflon/glass homogenizer and recentrifuged as decribed above. The final pellet was resuspended in 3 ml ice cold suspension buffer (20 mM HEPES, 10 mM NaCl, 1.26 mM $CaCl_2$, 0.81 mM $MgSO_4$, 0.22 mM $KH_2PO_4$, 10% w/v Sucrose, pH 7.4), giving a protein concentration of approx. 2 mg/ml. Protein concentration was measured by a BCA assay (Pierce), using bovine serum albumin as standard. The crude membrane preparation was aliquoted, flash-frozen in liquid nitrogen and stored at −80° C.

Before use in assays, each membrane preparation was tested and the protein concentration to give 3000 counts of total binding is determined. Typically, 6 μg/ml for MC-1, 1.5 μg/ml for MC-3, 1.5 μg/ml for MC-4, and 1 μg/ml for MC-5 give 3000 counts in the assay.

C. Assays:

Binding assays were performed in a total volume of 250 μl. Triamines and other compounds were dissolved in DMSO and diluted in PBS to give no more than 2.5% DMSO (0.25% final in the assay), and 25 μl of test compound is added to each tube. 50,000 dpm of $^{125}I$ labeled HP 467 (Ac-Nle-Gln-His-(p(I)-D-Phe)-Arg-(D-Trp)-Gly-$NH_2$, with the iodo group radioactively labeled; see WO 99/21571)(in 25 μl) prepared in 50 mM Tris pH 7.4, 2 mg/ml BSA, 10 mM $CaCl_2$, 5 mM $MgCl_2$, 2 mM EDTA were added to each tube. $^{125}I$-HP 467 was custom labeled by Amersham to a specific activity of 2000 Ci/mmol. Membranes were thawed and resuspended in ice-cold suspension buffer without sucrose at the protein concentration determined above, and 200 μl were added to each tube. Assays were incubated for 90 minutes at room temperature.

GF/B filter plates (Packard Instrument Co.) were prepared by soaking for at least one hour in 0.5% v/v polyethyleneimine. Assays were filtered using a Brandel 96-well cell harvester. The filters were washed four times with cold 50 mM Tris, pH 7.4. Filter plates were dehydrated for 2 hours and 35 μl of Microscint (Packard Instrument Co.) added to each well. Filter plates were counted using a Packard Topcount and data analyzed in MDL Screen (MDL Information Systems, Inc.).

All cell culture media and reagents were obtained from GibcoBRL except for Cosmic Calf™ Serum from HyClone. Fine chemicals were obtained form Sigma, and GF/B plates and Microscint were obtained from Packard Instruments.

EXAMPLE III cAMP Assay for Melanocortin Receptor Agonism

This example describes methods for assaying cAMP production from G-protein coupled MC receptors.

HEK 293 cells expressing MCR-1, MCR-3, MCR-4 and MCR-5 were used (see Example II). Cells were plated at 20,000 cells per well in a 96-well plate coated with collagen Biocoat (Becton Dickinson). The next day, cells were pretreated with 75 μl of 0.4 mM 3-isobutyl-1-methylxanthine (IBMX) in low serum medium containing DMEM, 25 mM HEPES, non-essential amino acids, vitamins, 100 units/ml penicillin, 100 μg/ml streptomycin and 0.1% COSMIC CALF SERUM. IBMX is an inhibitor of cAMP phosphodiesterase. The pretreatment was carried out for 10 min at 37° C.

Following pretreatment, 25 μl of diluted triamine derivative was added to the wells, and cells were incubated for 15 min at 37° C. Cells were lysed by adding 25 μl saponin lysis buffer and incubating 2 to 5 min. Plates were covered and stored at −20° C.

cAMP concentration was determined by ELISA. Briefly, 96 well ELISA plates were coated with goat anti-cAMP antibody (BabCo, Berkeley, Calif.) in PBS for 12 to 72 hr at 4° C. 50 μl of sample was mixed with 50 μl of cAMP ELISA buffer containing 1% bovine serum albumin, 10% heat inactivated donor horse serum, 1% normal mouse serum and 0.05% TWEEN-20 in PBS, and the diluted sample was added to the coated ELISA plate. Standards of known concentrations of cAMP were added to separate wells. 25 μl of 16 ng/ml cAMP-conjugated horse radish peroxidase (HRP) (cAMP-HRP) was added to each well, and the plates were incubated hr at room temperature. Plates were washed and the binding of cAMP-HRP was detected with 3,3',5,5'-tetramethylbenzidine (TMB) and hydrogen peroxide using standard immunoassay procedures.

EXAMPLE IV

Melanocortin Receptor Binding Profile of Triamine Derivatives

This example describes MC receptor binding affinity and specificity for various triamine derivatives.

Various triamine derivatives were tested for in vitro binding activity to HEK 293 cells expressing MCR-1, MCR-3, MCR-4 or MCR-5 as described in Example II. Tables 1 to 3 above show the IC50 values, the concentration giving 50% inhibition of binding of $^{125}I$-HP 467, for various triamine derivatives. As shown in Tables 2 and 3, triamine derivatives exhibited a range of affinities to MCR-1 and MCR-5. Some triamine derivatives exhibited specificity of about 10-fold for at least one MC receptor over another MC receptor, for example, TRG 6600 #4 and #8.

Several triamine derivatives exhibited similar affinities between all four MC receptors whereas other triamine derivatives showed specificity for at least one MC receptor over another MC receptor (compare Table 1 with Tables 2 and 3).

These results show that triamine derivatives are MC receptor ligands.

EXAMPLE V

Effect of Triamine derivatives on Melanocortin Receptor Signaling

This example shows the effect of triamine derivatives on MC receptor signaling.

Various triamine derivatives were tested for their ability to activate MC receptor by measuring cAMP as described in Example III. Tables 4 and 5 show the EC50 values, the effective concentration for achieving 50% of maximal cAMP production, for various triamine derivatives administered to HEK 293 cells expressing MCR-1, MCR-3, MCR-4 or MCR-5. The EC50 values shown in Tables 4 and 5 are μM. Table 3 also shows the maximum amount (in pmol) of cAMP produced in response to a given triamine derivative. As shown in Tables 4 and 5, triamine derivatives were able to activate various MC receptors with a range of affinities.

These results show that triamine derivatives are MC receptor ligands that can activate MC receptors, both generally and selectively.

EXAMPLE VI

Reduction of Lipopolysaccharide-Induced Tumor Necrosis Factor Levels in Mice

This example describes the effectiveness of triamine derivatives for decreasing tumor necrosis factor (TNF) levels in lipopolysaccharide (LPS; endotoxin) treated mice.

BALB/c female mice weighing approximately 20 g are placed into a control group and a treated group. Five mg/kg of LPS in 0.9% saline is administered (100 μl to give 100 μg LPS per mouse) by intraperitoneal (IP) injection to all mice. Mice in the treatment group receive either 30, 100, 300 or 600 μg of various triamine derivatives per mouse in a volume of 100 μl of PBS. Control mice receive 100 μl of saline alone. One minute after initial injections all mice receive the LPS injection. As a positive control, 100 μg of HP 228 is injected per mouse.

Blood samples are collected from the orbital sinus of treated and control mice 90 minutes or 105 minutes after LPS administration. The plasma is separated by centrifugation at 3000 ×g for 5 min and stored at −20° C. Samples are thawed and diluted, if TNF-α concentration is greater than 3200 μg/ml, with PBS containing 1% bovine serum albumin, 10% donor horse serum, 1% normal mouse serum, 0.05% TWEEN-20 and 0.05% thimerosal.

A 100 μl sample of plasma is assayed by ELISA for TNF-α. Briefly, ELISA plates are coated with hamster anti-mouse TNF-α antibody (Genzyme; Cambridge Mass.). Samples or known concentrations of TNF-α are added to the coated plates and incubated for 2 hr at 37° C. Plates are washed and subsequently incubated with biotinylated rabbit anti-mouse TNG-α for 1 hr at 37° C. Plates are washed and incubated with streptavidin-HRP for 1 hr at 37° C., and HRP activity is detected with hydrogen peroxide and o-phenylenediamine (OPD) using standard immunoassay procedures. The mean (±SEM) TNF-α level in mice from each group is determined and the percent reduction in TNF-α levels calculated.

EXAMPLE VII

Increasing Levels of IL-10 in Mice

This example describes the effectiveness of triamine derivatives in increasing the levels of IL-10 in mammals.

Triamine derivatives are administered intraperitoneally to mice in doses of 30, 100 or 300 μg/mouse or orally in doses of 300 or 600 μg/mouse. Levels of IL-10 are measured 90 or 105 minutes after administration as indicated. Samples are collected and diluted, when appropriate, as described in Example VI. A 100 μl sample of plasma is assayed by ELISA for IL-10. Briefly, ELISA plates are coated with rat anti-mouse IL-10 monoclonal antibody (Pharmingen; San Diego Calif.). Samples or known concentrations of IL-10 are added to the coated plates and incubated for 2 hr at 37° C. Plates are washed and incubated with biotinylated rat anti-mouse IL-10 (R&D Systems; Minneapolis Minn.) for 1 hr at 37° C. Plates are washed and incubated with streptavidin-HRP 30 min at 37° C., and HRP activity is detected with hydrogen peroxide and TMB using standard immunoassay procedures.

EXAMPLE VIII

Effect of Triamine Derivatives on Arachidonic Acid Induced Dermal Inflammation

This example describes the effect of triamine derivatives on arachidonic acid induced dermal inflammation.

Female BALB/c mice (17–22 g) are used and administered the test triamine derivatives or positive control compounds 30 to 60 min prior to topical application of arachidonic acid. Indomethacin and HP 228 are used as positive controls. Compounds are administered orally (p.o.) or intraperitoneally (i.p.). Initial ear thickness (left and right) is measured using spring loaded micro-calipers. Arachidonic acid is applied to mice anesthetized with a cocktail of ketamine/xylazine (7.0 mg/ml and 0.6 mg/ml, respectively) administered i.p. (300 μl/mouse). Utilizing a micro-pipette, 20 μl of arachidonic acid solution (100 mg/ml ethanol or acetone) is applied to the right ear (10 μl to inner and 10 μl to outer surfaces of both ears for a total of 2 mg arachidonic acid per right ear), and 20 μl of vehicle (ethanol or acetone) is applied to the left ear. Mice are returned to their cages to recover. Mice are again anesthetized 50 min after arachidonic acid application and their ears measured.

Dermal inflammation is determined by subtracting the difference of the vehicle treated left ear ($L_{60}-L_0$) from the difference of the arachidonic acid treated right ear ($R_{60}-R_0$). Ear thickness measurements are averaged for each group, and the responses in the vehicle treated control group (Cr; saline or PBS) are subtracted from the response noted in the triamine derivative treated group (Tr) to give the relative inflammatory response for each treatment group compared to the control group. The percent inhibition is defined by the equation: % inhibition=(Cr−Tr)/(Cr)×100.

EXAMPLE IX

Reduction in Body Weight Due to Administration of Triamine Derivatives

This example demonstrates that administration of an triamine derivative can cause a decrease in the body weight of a subject.

Described below are methods for determining the effects of novel compounds on food intake in rats over a 24-hour period. The MC-4 receptor is believed to be involved in the regulation of food intake and weight gain. Thus, chronic MC-4 antagonism by agouti or AGRP is associated with hyperphagia and obesity (similarly for MC-4 R knockout mice) and rats treated with a potent and prototypic MC-4 agonist, HP228, have demonstrated notable hypophagia and weight loss (IP, ICV). The triamine compound used in this assay has demonstrated in vitro efficacy for binding to and agonizing the human melanocortin-4 (MC-4) receptor.

A. Assay Preparation

1. Materials and Buffers

The triamine compounds was lyophilized and in the form of dry, powdery grains or a sticky substance.

HP228: (Ac-Nle-Gln-His-(D)-Phe-Arg-(D)-Trp-Gly-NH$_2$: (Multiple Peptide Systems, San Diego, Calif.)

Sibutramine: Novartis, Basel, Switzerland, or Meridia (prescription form)

Dulbecco's Phosphate Buffered Saline (PBS): GibcoBRL

Milli-Q Water: Double distilled water from Trega Biosciences, San Diego, Calif.

Polyethylene Glycol 400 (PEG400; 10% v/v for "PEG400" oral formulation) Propylene Glycol (1,2 propane-diol; 30% v/v for "PEG400" oral formulation)

100% EtOH (10% v/v for "PEG400" oral formulation)

Milli-Q water (50% v/v for "PEG400" oral formulation)

2. Compound Preparation a. Control Compounds:

PBS (with up to 5% EtOH v/v) was used as the negative control for all treatments administered IP and ICV and 'PEG400' oral formulation is the standard vehicle for all treatments administered PO.

HP228 was the positive control for all intraperitoneal (IP) and intracerebroventricular (ICV) studies and Sibutramine the positive control for all perioral (PO) studies. HP228 and Sibutramine solutions were made up fresh either on the day of the assay (regular light cycle; 6pm–6am) or the previous afternoon (reverse light cycle; 9am–9pm). HP228 was dissolved in PBS to create a 5 mg/ml (1 ml/kg IP) or 1 mg/ml (10 μg/rat ICV) solution.

Sibutramine, a novel serotinin and noradrenaline re-uptake inhibitor, which is an approved weight loss treatment, was the positive control for all perioral (PO) studies. Sibutramine has been shown to lower body weight in various rodent models (normal, Zucker fatty and diet-induced obesity) by reducing food intake and increasing energy expenditure. Sibutramine was dissolved in the appropriate amount of "PEG400 oral formulation" to yield a 10 mg/kg treatment dose (2 ml/kg @ 5 mg/ml).

The triamine compound (TRG 6600 #3) was dissolved in (up to 5% v/v) EtOH/PBS (IP, ICV) or PEG400 (PO) to yield the appropriate concentration for treatment at a volume of 1 ml/kg (IP), 2 ml/kg (PO) or 10 ml/rat (ICV) and was stored at 4° C. The triamine compound was administered IP (£ 10 mg/kg), PO (£ 60 mg/kg) and ICV (£ 50 mg/rat).

3. Assay Protocol

This protocol is designed for fed, non-obese rats as fasting induces several factors (e.g., leptin, neuropeptide Y, AGRP) that may serve to confound the interpretation of an acute, initial in vivo screen.

Adult, male rats (Sprague-Dawley; 200–225 g upon arrival and 250–300 g at time of study) from Harlan Laboratories (San Diego, Calif.) were acclimated in the study vivarium for at least one week with free access to food and water. Animals that will be experimentally monitored in the reverse light:dark cycle room were acclimated for approximately 9 days and/or until daily feeding has returned to control levels. Animals with an ICV cannula implanted into the lateral ventricles were allowed to recover and acclimate for 4–5 days after surgery and body weight and food consumption was tracked following surgery. Baseline body weight and food consumption measurements for studies with all routes of treatment administration (IP, PO, ICV) were taken for 2 days prior to the start of the study with animals in individual cages. On the study day, body weight measurements were taken and the animals were randomly divided into groups (n=6–8) such that food consumption (from the previous day) was equivalent between all groups.

Four groups (n=6–8) were run at one time: a negative and a positive control and two different novel compounds. Thus, animals were administered a single treatment of the following:

Negative Vehicle Control: EtOH/PBS (1 ml/kg IP; 10 ml/rat ICV)
Negative Vehicle Control: PEG400 Oral Formulation (2 ml/kg PO)
Positive Control: HP228 (5 mg/kg IP; 50 mg/rat ICV)
Positive Control: Sibutramine (10 mg/kg PO)
Triamine derivative compound: 5–10 mg/kg IP; 50 mg/rat ICV; 30–60 mg/kg PO.

Treatments were administered approximately 1 hour before the beginning of the dark cycle (regular 6pm–6am; reverse 9am–9pm) and the animals were returned to their individual cages with ad libitum access to food and water. Food consumption measurements were obtained 2, 4, 6, 18 and 24 hours after treatment (regular light cycle) or 2, 4, 6, 8 and 24 hours after treatment (reverse light cycle) by weighing the cage lid with all remaining food and calculating the difference from baseline (time 0). Measurements during the dark cycle were taken under red light conditions. Treatment solutions were administered ICV at room temperature over approximately 10 seconds by conscious injection of a 10 ml volume.

B. Data Analysis

All data were reported as means±standard error of the mean (SEM) and analyzed by one of the following appropriate statistical methods: one-way analysis of variance (ANOVA) with Student Newman-Keuls test for multiple comparisons, ANOVA for repeated measures, or a Student's t-test where appropriate.

Figure 4:
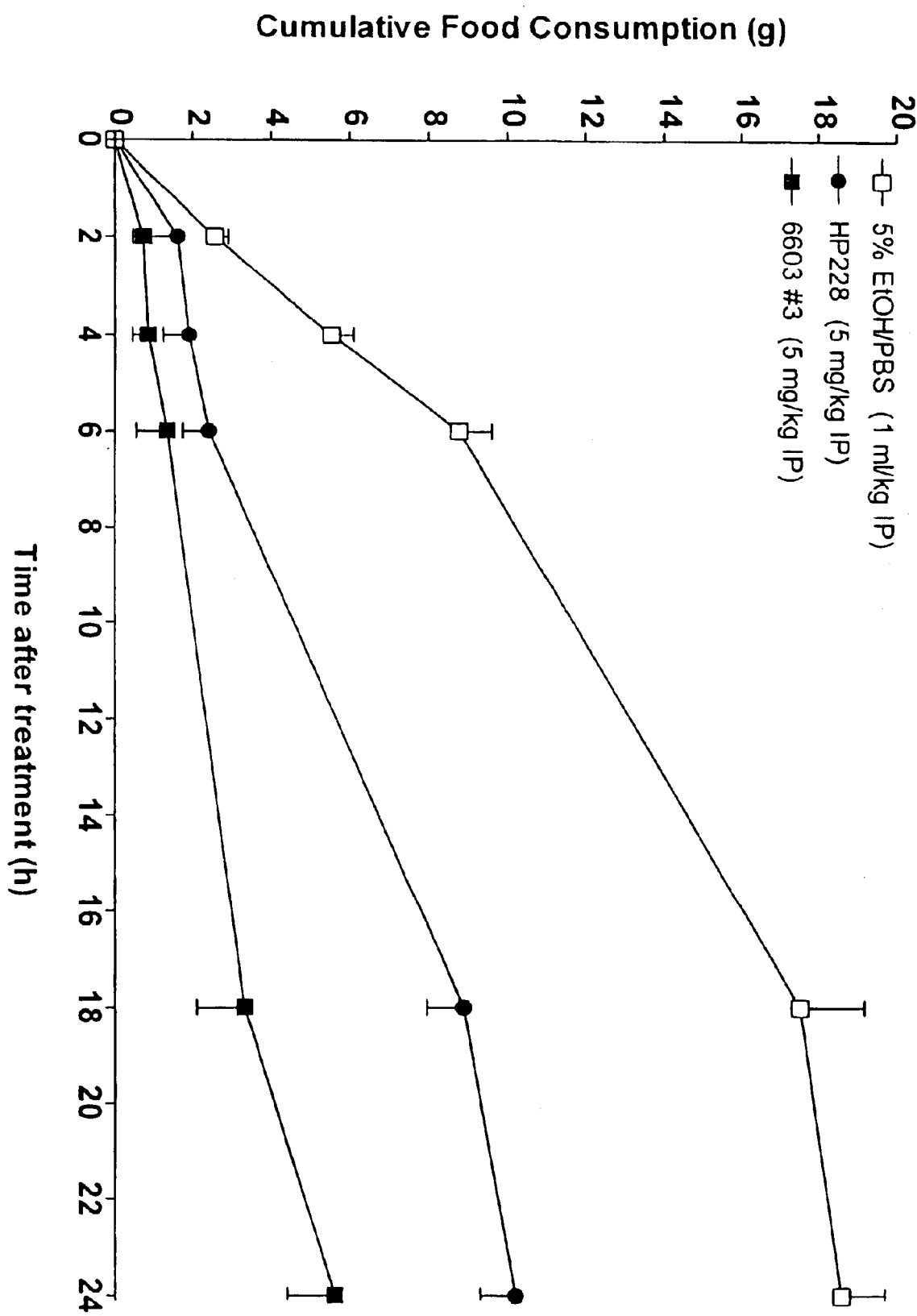
FIG. 4 shows the acute hypophagic effect of a triamine derivative (TRG 6603 #3) administered intraperitoneally (IP) to rats.
Figure 5:
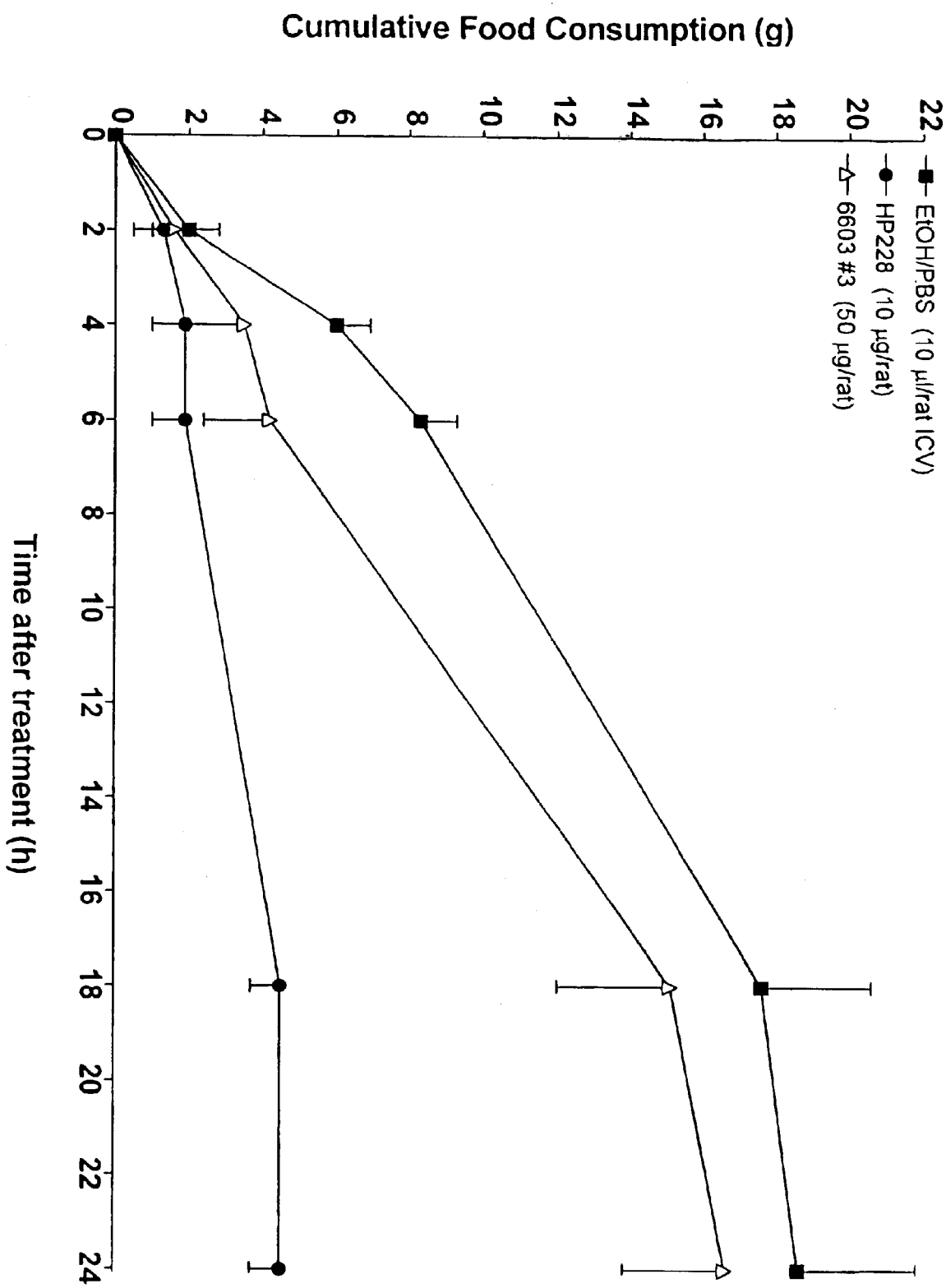
FIG. 5 shows the acute hypophagic effect of a triamine derivative (TRG 6603 #3) administered intracerebroventricularly (ICV) to rats.

Administration of the test triamine compound ICV caused a statistically significant decrease in the food intake of rats at 4 and 6 hours after injection (see FIG. 5). In addition, administration of the test triamine compound IP caused a statistically significant reduction in the food intake of rats over the 24 hour test period (see FIG. 4). These results indicate that a triamine derivative can decrease weight gain and food intake in subjects.

EXAMPLE X

Penile Erection Due to Administration of Triamine Derivative

Assay Method

Adult male rats are housed 2–3 per cage and acclimated to the standard vivarium light cycle (12 hr. light, 12 hr. dark), rat chow and water for a least a week prior to testing. All experiments are performed between 9 a.m. and noon and rats are placed in cylindrical, clear plexiglass chambers during the 60 minute observation period. Mirrors are positioned below and to the sides of the chambers to improve viewing.

Observations begin 10 minutes after an unstraperitoneal injection of either saline or compound. An observer counts the number of grooming motions, stretches, yawns and penile erections (spontaneously occurring, not elicited by genital grooming) and records them every 5 minutes, for a total of 60 minutes. The observer is unaware of the treatment and animals are tested once, with n=6 in each group. HP 228 is used as a positive control for penile erections. Differences between groups are determined by an overall analysis of variance and the Student Neunmann-Keuls post hoc test is used to identify individual differences between groups ($p \leq 0.05$).

As recited in the claims below, amended or unamended as filed or later added, the term "comprising" is open-ended, regardless of where in the claim the term is recited.

All references cited herein are fully incorporated by reference.

Although the invention has been described with reference to the examples provided above, it should be understood that various modifications can be made without departing from the spirit of the invention. Accordingly, the invention is limited only by the following claims.

We claim:

1. A compound of the formula:

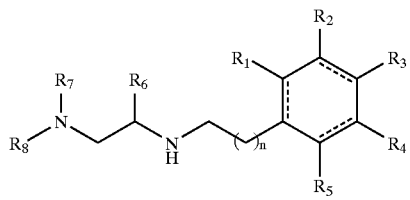

wherein:
the dotted lines indicate that the depicted ring is selected from the group consisting of phenyl and cyclohexyl;
n is 0, 1 or 2;
$R_1$ to $R_5$ are, independently, selected from the group consisting of a hydrogen atom, halo, hydroxy, protected hydroxy, nitro, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_1$ to $C_6$ alkoxy, $C_1$ to $C_6$ substituted alkoxy, phenoxy, substituted phenoxy, $C_1$ to $C_6$ alkylthio, $C_1$ to $C_6$ substituted alkylthio, $C_1$ to $C_6$ alkylsulfonyl, $C_1$ to $C_6$ substituted alkylsulfonyl, phenylthio, substituted phenylthio, phenylsulfonyl, substituted phenylsulfonyl, amino, protected amino, (monosubstituted)amino, protected (monosubstituted) amino and (disubstituted)amino; and when any one of adjacent position pairs $R_1$ and $R_2$, $R_2$ and $R_3$, and $R_3$ and R and $R_4$ and $R_5$ together form a moiety selected from the group consisting of phenyl, substituted phenyl, heterocycle and substituted heterocycle, said moiety fused to the phenyl ring depicted in the above formula such that a bicyclic ring results;

$R_6$ is selected from the group consisting of $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_{11}$ to $C_{16}$ naphthylalkyl and $C_{11}$ to $C_{16}$ substituted naphthylalkyl;

where $R_7$ is absent, $R_8$ together with the attached nitrogen depicted in the above formula form a substituted heterocycle or a substituted cyclic $C_3$ to $C_7$ heteroalkylene, wherein at least one of said substitution is the formula -D-E, wherein D may be absent or present and, if present, is selected from the group consisting of $C_1$ to $C_6$ alkylene and $C_1$ to $C_6$ substituted alkylene; and E is selected from the group consisting of amino, protected amino, (monosubstituted)amino, protected (monosubstituted)amino and (disubstituted) amino group; and where $R_7$ is selected from the group consisting of a hydrogen atom, $C_1$ to $C_6$ alkyl and $C_1$ to $C_6$ substituted alkyl, $R_8$ is the formula X—CH—Y, wherein the attached nitrogen depicted in the above formula is attached to the carbon atom of the formula X—CH—Y, and wherein X is selected from the group consisting of a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl, naphthyl and substituted naphthyl, and Y is the formula —$(CH_2)_n$—Z, wherein n is 1 to 6 and Z is selected from the group consisting of amino, protected amino, (monosubstituted)amino, protected (monosubstituted) amino and (disubstituted)amino;

wherein, when a) the depicted ring is phenyl, and b) $R_1$ to $R_5$ and $R_7$ are each hydrogen and c) $R_8$ is the formula X—CH—Y, where X is benzyl and Y is —$CH_2$-amino, then $R_6$ is not benzyl; or a pharmaceutically-acceptable salt thereof.

2. The compound of claim 1, wherein, when the depicted ring is phenyl, at least one of $R_1$ to $R_5$ is not hydrogen.

3. A The compound of claim 1, wherein, when the depicted ring is phenyl, $R_6$ is not benzyl.

4. The compound of claim 1, wherein the depicted ring is phenyl.

5. The compound of claim 1, wherein the depicted ring is cyclohexyl.

6. The compound of claim 1, wherein n is 1.

7. The compound of claim 1, wherein $R_1$ to $R_5$ are, independently, selected from the group consisting of a hydrogen atom, halo, hydroxy, protected hydroxy, nitro, $C_1$ to $C_6$ alkyl, $C_1$ to $C_6$ substituted alkyl, phenyl, substituted phenyl, $C_1$ to $C_6$ alkylthio, $C_1$ to $C_6$ substituted alkylthio, $C_1$ to $C_6$ alkylsulfonyl, $C_1$ to $C_6$ substituted alkylsulfonyl, $C_1$ to $C_6$ alkoxy, $C_1$ to $C_6$ substituted alkoxy, phenoxy, substituted phenoxy, amino, (monosubstituted)amino and (disubstituted)amino.

8. The compound of claim 1, wherein $R_6$ is selected from the group consisting of $C_1$ to $C_6$ alkyl, $C_1$ to $C_6$ substituted alkyl, $C_7$ to $C_{12}$ phenylalkyl and $C_7$ to $C_{12}$ substituted phenylalkyl.

9. The compound of claim 1, wherein $R_7$ is absent and $R_8$ together with the attached nitrogen depicted in the above formula form a substituted heterocycle or a substituted cyclic $C_3$ to $C_7$ heteroalkylene, wherein at least one of said substitution is the formula -D-E, wherein D is $C_1$ to $C_6$ alkylene and E is selected from the group consisting of amino, (monosubstituted)amino and (disubstituted)amino.

10. The compound of claim 1, wherein $R_7$ is a hydrogen atom and $R_8$ is the formula X—CH—Y, wherein the attached nitrogen depicted in the above formula is attached to the carbon atom of the formula X—CH—Y, and wherein X is selected from the group consisting of a $C_1$ to $C_6$ alkyl, $C_1$ to $C_6$ substituted alkyl, $C_7$ to $C_{12}$ phenylalkyl and $C_7$ to $C_{12}$ substituted phenylalkyl and Y is the formula —$(CH_2)_m$—Z, wherein m is 1 or 2 and Z is selected from the group consisting of amino, (monosubstituted)amino and (disubstituted)amino.

11. The compound of claim 1, wherein $R_1$ to $R_5$ are, independently, selected from the group consisting of a hydrogen atom, halo, hydroxy, protected hydroxy, nitro, $C_1$ to $C_6$ alkyl, $C_1$ to $C_6$ substituted alkyl, phenyl, substituted phenyl, $C_1$ to $C_6$ alkylthio, $C_1$ to $C_6$ substituted alkylthio, $C_1$ to $C_6$ alkylsulfonyl, $C_1$ to $C_6$ substituted alkylsulfonyl, $C_1$ to $C_6$ alkoxy, $C_1$ to $C_6$ substituted alkoxy, phenoxy, substituted phenoxy, amino, (monosubstituted)amino and (disubstituted)amino;

$R_6$ is selected from the group consisting of $C_1$ to $C_6$ alkyl, $C_1$ to $C_6$ substituted alkyl, $C_7$ to $C_{12}$ phenylalkyl and $C_7$ to $C_{12}$ substituted phenylalkyl;

$R_7$ is absent and $R_8$ together with the attached nitrogen depicted in the above formula form a substituted heterocycle or a substituted cyclic $C_3$ to $C_7$ heteroalkylene, wherein at least one of said substitution is the formula -D-E, wherein D is $C_1$ to $C_6$ alkylene and E is selected from the group consisting of amino, (monosubstituted)amino and (disubstituted)amino group; or $R_7$ is a hydrogen atom and $R_8$ is the formula X—CH—Y, wherein the attached nitrogen depicted in the above formula is attached to the carbon atom of the formula X—CH—Y, and wherein X is selected from the group consisting of a $C_1$ to $C_6$ alkyl, $C_1$ to $C_6$ substituted alkyl, $C_7$ to $C_{12}$ phenylalkyl and $C_7$ to $C_{12}$ substituted phenylalkyl and Y is the formula —$(CH_2)_n$—Z, wherein n is 1 to 2 and Z is selected from the group consisting of amino, (monosubstituted)amino and (disubstituted) amino.

12. The compound of claim 1, wherein $R_1$ to $R_5$ are selected, independently, from the group consisting of a hydrogen atom, methyl, isopropyl, hydroxy, ethoxy, methoxy, butoxy, phenoxy, chloro, fluoro, bromo, nitro, trifluoromethyl, phenyl, methylthio, trifluoromethylthio, trifluoromethoxy, methylsulfonyl and dimethylamino.

13. The compound of claim 1, wherein $R_2$ and $R_3$ form a phenyl or substituted phenyl that is fused to the phenyl depicted in the above formula.

14. The compound of claim 1, wherein $R_6$ is selected from the group consisting of a benzyl, 4-(iodophenyl)methyl, 4-(chlorophenyl)methyl, 4-(bromophenyl)methyl, 2-(methoxyphenyl)methyl, 3-(methoxyphenyl)methyl, 4-(ethoxyphenyl)methyl, 4-(propoxyphenyl)methyl, 4-(ethylphenyl)methyl, 4-(isopropylphenyl)methyl, 4-(isobutylphenyl)methyl, 4-(trifluoromethylphenyl)methyl, 3,4-(dimethoxyphenyl)methyl, 4-(t-butylphenyl)methyl, 4-(2-(1-piperidyl)ethoxy)phenylmethyl, 4-((3,3-dimethyl)butoxyphenyl)methyl, 4-((3-methyl)butoxyphenyl)methyl, 4-((2-dimethylamino)ethoxyphenyl)methyl, 2-phenethyl, 2-(4-methoxyphenyl)ethyl, 3-indolylmethyl, 4-(biphenyl)methyl, 1-naphthylmethyl, 2-naphthylmethyl, diphenylmethyl, 3,4-dichlorophenylmethyl and 2-methoxyethyl.

15. The compound of claim 1, wherein $R_7$ is absent and $R_8$ together with the nitrogen depicted in the above formula are selected from the group consisting of 3-(aminomethyl)-7-hydroxyisoquinolyl, 3-(aminomethyl)isoquinolyl, 2-(aminomethyl)pyrrolidyl, trans-2-aminomethyl-4-hydroxypyrrolidyl, 4-aminomethylthiazolidin-3-yl and 2-(aminomethyl)piperidyl.

16. The compound of claim 1, wherein $R_7$ is a hydrogen atom and $R_8$ is the formula X—CH—Y, wherein Y is aminomethyl and X its selected from the group consisting of 3-guanidinopropyl, 2-aminoethyl, 3-(methylamino)propyl, 4-aminobutyl, hydroxymethyl, 4-nitrophenylmethyl, benzyl, 3-(aminomethyl)phenylmethyl, 4-(aminomethyl) phenylmethyl, 4-hydroxyphenylmethyl, 3-pyridylmethyl, 4-pyridylmethyl, 2-thienylmethyl, butyl, 2-(ethylamino)ethyl, 2-(dimethylamino)ethyl, 3-(dimethylamino)propyl, 4-(dimethylamino)butyl, 1-hydroxyethyl, 2-hydroxyethyl, 3-hydroxypropyl, 1-methylethyl, 1,1-dimethylethyl, methoxymethyl, 2-pyridylmethyl, 2-methylsulfonylethyl, thiomethyl, 2-(methylthio)ethyl, 1-methyl-1-thioethyl, ethyl, 4-(2,2,2-trifluoroethylamino)butyl, aminomethyl, methylaminomethyl, dimethylaminomethyl, ethylaminomethyl, butylaminomethyl, 2,2-dimethylpropylaminoethyl, benzylaminoethyl, 2-phenethylaminomethyl, 3-phenylpropylaminomethyl, cyclohexylmethylaminomethyl, 2-cyclohexylethylaminomethyl, 4-hydroxybutylaminomethyl, 5-hydroxypentylaminomethyl, 2-methoxyaminoethylaminomethyl, 3-methoxypropylaminomethyl, 2-phenoxyethylaminomethyl, 2-(2-methoxy)ethoxyethylaminomethyl, 2-thienylsulfonylamidomethyl, 4-(methoxy)phenylsufonylamidomethyl, phenylsulfonylamidomethyl, 4-(butoxy)phenylsulfonylamidomethyl, methylsulfonylamidomethyl, 3-(4-morpholinyl)propyl, 3-cyclopropylaminopropyl, 3-(tetrahydofurfurylamino)propyl, 3-(4-hydroxypiperidinyl)propyl, 3-(1,1-dimethyl-2-hydroxyethylamino)propyl, 3-(N-(2-hydroxyethyl)methylamino)propyl, 3-(N-(cyclohexyl)methylamino)propyl, 2-(4-morpholinyl)ethyl, 2-cyclopropylaminoethyl, 2-(tetrahydrofurfurylamino)ethyl, 2-(4-hydroxypiperidinyl)ethyl, 2-(1,1-dimethyl-2-hydroxyethylamino)ethyl, 2-(N-(2-hydroxyethyl)methylamino)ethyl, 2-(N-(cyclohexyl)methylamino)ethyl, 4-ethylaminobutyl, 4-(2-methoxyethylamino)butyl, 3-ethylaminopropyl, 3-(2-methoxyethylamino)propyl, 3-pyridylmethylaminopropyl, 3-(methylamino)propyl, 3-aminopropyl, 3-(butylamino)propyl, 3-(2,2-dimethylpropylamino)propyl, 3-(phenylmethylamino)propyl, 3-(2-phenylethylamino)propyl, 3-(3-phenylpropylamino)propyl, 3-(2-cyclohexylethylamino)propyl, 3-(3-pridylmethylamino)propyl, 3-(3-methoxypropylamino)propyl, 3-(4-hydroxybutylamino)propyl, 3-(5-hydroxypentylamino)propyl, 3-(2-phenyoxyethylamino)propyl, 3-(methylamino)propyl, 4-aminobutyl, 4-(butylamino)butyl, 4-(2,2-dimethylpropylamino)butyl, 4-(phenylmethylaminom)butyl, 4-(2-phenylethylamino)butyl, 4-(3-phenylpropylamino)butyl, 4-(cyclohexylmethylamino)butyl, 4-(2-cyclohexylethylamino)butyl, 4-(3-pridylmethylamio)butyl, 4-(3-methoxypropylamino)butyl, 4-(4-hydroxybutylamino)butyl, 4-(5-hydroxypentylamino)butyl, 4-(2-phenyoxyethylamino)butyl and 4-((2-(2-methoxy)ethoxy)ethylamino)butyl.

17. The compound of claim 1, wherein $R_1$ to $R_5$ are selected, independently, from the group consisting of a hydrogen atom, methyl, isopropyl, hydroxy, ethoxy, methoxy, butoxy, phenoxy, chloro, fluoro, bromo, nitro, trifluoromethyl, phenyl, methylthio, trifluoromethoxy, methylsulfonyl and dimethylamino, and wherein $R_2$ and $R_3$ form a phenyl that is fused to the phenyl depicted in the above formula;

$R_6$ is selected from the group consisting of 4-(iodophenyl)methyl, 4-(chlorophenyl)methyl, 4-(bromophenyl)methyl, 2-(methoxyphenyl)methyl, 3-(methoxyphenyl)methyl, 4-(ethoxyphenyl)methyl, 4-(propoxyphenyl)methyl, 4-(ethylphenyl)methyl, 4-(isopropylphenyl)methyl, 4-(trifluoromethylphenyl)methyl, 3,4-(dimethoxyphenyl)methyl, 4-(t-butylphenyl)methyl, 4-(2-(1-piperidyl)ethoxy)phenylmethyl, 4-((3,3-dimethyl)butoxyphenyl)methyl, 4-((3-methyl)butoxyphenyl)methyl, 4-((2-dimethylamino)ethoxyphenyl)methyl, 2-phenethyl, 2-(4-methoxyphenyl)ethyl, 3-indolylmethyl, 4-(biphenyl)methyl, 1-naphthylmethyl, 2-naphthylmethyl, diphenylmethyl, 3,4-dichlorophenylmethyl and 2-methoxyethyl; and $R_7$ is absent and $R_8$ together with the nitrogen depicted in the above formula are selected from the group consisting of 3-(aminomethyl)-7-hydroxyisoquinolyl, 3-(aminomethyl)isoquinolyl, 2-(aminomethyl)pyrrolidyl, trans-2-aminomethyl-4-hydroxypyrrolidyl, 4-aminomethylthiazolidin-3-yl and 2-(aminomethyl)piperidyl; or $R_7$ is a hydrogen atom and $R_8$ is the formula X—CH—Y, wherein Y is aminomethyl and X is selected from the group consisting of 3-guanidinopropyl, 2-aminoethyl, 3-(methylamino)propyl, 4-aminobutyl, hydroxymethyl, 4-nitrophenylmethyl, benzyl, 3-(aminomethyl)phenylmethyl, 4-(aminomethyl)phenylmethyl, 4-hydroxyphenylmethyl, 3-pyridylmethyl, 4-pyridylmethyl, 2-thienylmethyl, butyl, 2-(ethylamino)ethyl, 2-(dimethylamino)ethyl, 3-(dimethylamino)propyl, 4-(dimethylamino)butyl, 1-hydroxyethyl, 2-hydroxyethyl, 3-hydroxypropyl, 1-methylethyl, 1,1-dimethylethyl, methoxymethyl, 2-pyridylmethyl, 2-methylsulfonylethyl, thiomethyl, 2-(methylthio)ethyl, 1-methyl-1-thioethyl, ethyl, 4-(2,2,2-trifluoroethylamino)butyl, aminomethyl, methylaminomethyl, dimethylaminomethyl, ethylaminomethyl, butylaminomethyl, 2,2-dimethylpropylaminoethyl, benzylaminoethyl, 2-phenethylaminomethyl, 3-phenylpropylaminomethyl, cyclohexylmethylaminomethyl, 2-cyclohexylethylaminomethyl, 4-hydroxybutylaminomethyl, 5-hydroxypentylaminomethyl, 2-methoxyaminoethylaminomethyl, 3-methoxypropylaminomethyl, 2-phenoxyethylaminomethyl, 2-(2-methoxy)

ethoxyethylaminomethyl, 2-thienylsulfonylaminomethyl, 4-(methoxy)phenylsufonylaminomethyl, phenylsulfonylaminomethyl, 4-(butoxy)phenylsulfonylaminomethyl, methylsulfonylaminomethyl, 3-(4-morpholinyl)propyl, 3-cyclopropylaminopropyl, 3-(tetrahydofurfurylamino)propyl, 3-(4-hydroxypiperidinyl)propyl, 3-(1,1-dimethyl-2-hydroxyethylamino)propyl, 3-(N-(2-hydroxyethyl)methylamino)propyl, 3-(N-(cyclohexyl)methylamino)propyl, 2-(4-morpholinyl)ethyl, 2-cyclopropylaminoethyl, 2-(tetrahydrofurfurylamino)ethyl, 2-(4-hydroxypiperidinyl)ethyl, 2-(1,1-dimethyl-2-hydroxyethylamino)ethyl, 2-(N-(2-hydroxyethyl)methylamino)ethyl, 2-(N-(cyclohexyl)methylamino)ethyl, 4-ethylaminiobutyl, 4-(2-methoxyethylamino)butyl, 3-ethylaminopropyl, 3-(2-methoxyethylamino)propyl, 3-pyridylmethylaminomethyl, 3-(methylamino)propyl, 3-aminopropyl, 3-(butylamino)propyl, 3-(2,2-dimethylpropylamino)propyl, 3-(phenylmethylamino)propyl, 3-(2-phenylethylamino)propyl, 3-(3-phenylpropylamino)propyl, 3-(2-cyclohexylethylamino)propyl, 3-(3-pridylmethylamino)propyl, 3-(3-methoxypropylamino)propyl, 3-(4-hydroxybutylamino)propyl, 3-(5-hydroxypentylamino)propyl, 3-(2-phenyoxyethylamino)propyl, 3-(methylamino)propyl, 4-aminobutyl, 4-(butylamino)butyl, 4-(2,2-dimethylpropylamino)butyl, 4-(phenylmethylaminom)butyl, 4-(2-phenylethylamino)butyl, 4-(3-phenylpropylamino)butyl, 4-(cyclohexylmethylamino)butyl, 4-(2-cyclohexylethylamino)butyl, 4-(3-pridylmethylamio)butyl, 4-(3-methoxypropylamino)butyl, 4-(4-hydroxybutylamino)butyl, 4-(5-hydroxypentylamino)butyl, 4-(2-phenyoxyethylamino)butyl and 4-((2-(2-methoxy)ethoxy)ethylamino)butyl.

18. The compound of claim 1, wherein:
the depicted ring is phenyl;
n is 1;
$R_1$, $R_2$, $R_4$, and $R_5$, are each a hydrogen atom;
$R_3$ is selected from the group consisting of chloro, fluoro and bromo;
$R_6$ is selected from the group consisting of (4-ethoxyphenyl)methyl, (4-propoxyphenyl)methyl, (4-t-butylphenyl)methyl, (4-iodophenyl)methyl and (4-phenylphenyl)methyl;
$R_7$ is a hydrogen atom or absent;
when $R_7$ is a hydrogen atom, $R_8$ is the formula X—CH—Y, wherein Y is aminomethyl and X is selected from the group consisting of 2-hydroxyethyl, 2-(ethylamino)ethyl, 2-(cyclopropylamino)propyl, 2-(3-methoxypropylamino)propyl, 2-(4-hydroxypiperidin-1-yl)propyl, 2-(2-hydroxy-1,1-dimethylethylamino) propyl, 3-aminopropyl, 2-(methylsulfonyl)ethyl, 2-aminoethyl, 2-(4-hydroxypiperidin-1-yl)ethyl, 2-(2-hydroxy-1,1-dimethylethylamino)ethyl, 2-(tetrahydrofurfurylamino)propyl, 3-(3-methoxypropylamino)propyl, 2-((2-hydroxyethyl)methylamino)ethyl, 3-hydroxypropyl, 3-(methylamino)propyl, 3-(ethylamino)propyl, 3-(butylamino)propyl, 3-(2,2,-dimethylpropyl.amino)propyl, 3-(cyclohexylmethylamino)propyl, 3-(3-pyridylmethylamino)propyl, 3-(2-methoxyethylamino)propyl, 3-(3-methoxypropylamino)propyl, 3-(4-hydroxybutylamino)propyl, 3-(5-hydroxypentylamino)propyl, 3-dimethylaminopropyl, (3-aminomethyl)phenylmethyl, 3-(2-phenoxyethylamino)propyl, 4-(ethylamino)butyl, 4-(2-methoxyethylamino)butyl, 4-(3-methoxypropylamino)butyl, 4-(4-hydroxybutylamino)butyl, 4-(5-hydroxypentylamino)butyl, 4-((2-(2-methoxy)ethoxy)ethylamino)butyl, 3-guanidinopropyl, 4-guanidinobutyl, hydroxymethyl and 2-dimethylaminoethyl;
and, when $R_7$ is absent, $R_8$ is trans-2-aminomethyl-4-hydroxypyrrolidyl.

19. A compound of the formula:

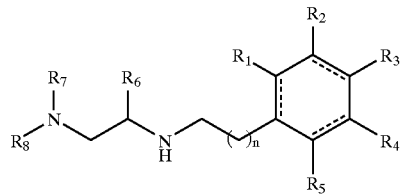

wherein:
the dotted lines indicate that the depicted ring is selected from the group consisting of phenyl and cyclohexyl;
n is 0, 1 or 2;
$R_1$ to $R_5$ are, independently, selected from the group consisting of a hydrogen atom, halo, hydroxy, protected hydroxy, nitro, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, naphthyl, substituted naphthyl, $C_1$ to $C_6$ alkoxy, $C_1$ to $C_6$ substituted alkoxy, phenoxy, substituted phenoxy, $C_1$ to $C_6$ alkylthio, $C_1$ to $C_6$ substituted alkylthio, $C_1$ to $C_6$ alkylsulfonyl, $C_1$ to $C_6$ substituted alkylsulfonyl, phenylthio, substituted phenylthio, phenylsulfonyl, substituted phenylsulfonyl, amino, protected amino, (monosubstituted) amino, protected (monosubstituted) amino and (disubstituted)amino; and when any one of adjacent position pairs $R_1$ and $R_2$, $R_2$ and $R_3$, and $R_3$ and $R_4$ and $R_4$ and $R_5$ together form a moiety selected from the group consisting of phenyl, substituted phenyl, heterocycle and substituted heterocycle, said moiety fused to the phenyl ring depicted in the above formula such that abicyclic ring results;
$R_6$ is selected from the group consisting of a hydrogen atom, $C_1$ to $C_6$ alkyl, $C_1$ to $C_6$ substituted alkyl, $C_7$ to $C_{12}$ phenylalkyl, $C_7$ to $C_{12}$ substituted phenylalkyl, $C_{11}$ to $C_{16}$ naphthylalkyl and $C_{11}$ to $C_{16}$ substituted naphthylalkyl;
where $R_7$ is absent, $R_8$ together with the attached nitrogen depicted in the above formula form a substituted heterocycle or a substituted cyclic $C_3$ to $C_7$ heteroalkylene, wherein at least one of said substitution is the formula -D-E, wherein D may be absent or present and, if present, is selected from the group consisting of $C_1$ to $C_6$ alkylene and $C_1$ to $C_6$ substituted alkylene; and E is selected from the group consisting of amino, protected amino, (monosubstituted)amino, protected (monosubstituted)amino and (disubstituted) amino group; and
where $R_7$ is selected from the group consisting of a hydrogen atom, $C_1$ to $C_6$ alkyl and $C_1$ to $C_6$ substituted alkyl, $R_8$ is the formula X—CH—Y, wherein the attached nitrogen depicted in the above formula is attached to the carbon atom of the formula X—CH—Y, and wherein X is selected from the group consisting of a $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl, naphthyl and substituted naphthyl, and Y is the formula —$(CH_2)_n$—Z, wherein n is 1 to 6 and Z is selected from the group consisting of amino, protected amino, (monosubstituted)amino, protected (monosubstituted)amino and (disubstituted)amino;

wherein, when a) the depicted ring is phenyl, and b) $R_1$ to $R_5$ and $R_7$ are each hydrogen and c) $R_8$ is the formula X—CH—Y, where X is benzyl and Y is —$CH_2$-amino, then $R_6$ is not benzyl; or a pharmaceutically-acceptable salt thereof.

* * * * *